US005968769A

United States Patent [19]
Green et al.

[11] Patent Number: 5,968,769
[45] Date of Patent: *Oct. 19, 1999

[54] **SEQUENCE AND ANALYSIS OF LKP PILIN STRUCTURAL GENES AND THE LKP PILI OPERON OF NONTYPABLE *HAEMOPHILUS INFLUENZAE***

[75] Inventors: Bruce A. Green, Pittsford, N.Y.; Charles C. Brinton, Jr., Export, Pa.

[73] Assignee: American Cyanamid Co. and Bactex, Inc., Madison, N.J.

[ * ] Notice: This patent is subject to a terminal disclaimer.

[21] Appl. No.: 08/477,326

[22] Filed: Jun. 7, 1995

Related U.S. Application Data

[63] Continuation-in-part of application No. 08/277,231, Jul. 19, 1994, Pat. No. 5,643,725.

[51] Int. Cl.⁶ .............................. C12P 21/00; C12N 5/16; C12N 7/01; C12N 15/31
[52] U.S. Cl. ...................... 435/69.1; 435/320.1; 435/325; 536/23.7; 935/9; 935/55; 935/70; 935/72
[58] Field of Search ....................... 435/6, 91.2, 7.1–7.9, 435/69.1, 325, 320.1; 514/2; 536/23.1, 23.7, 24.3–24.32; 935/9, 55, 70, 72

[56] References Cited

U.S. PATENT DOCUMENTS

| | | | |
|---|---|---|---|
| 4,801,690 | 1/1989 | Brinton, Jr. et al. | 530/396 |
| 5,336,490 | 8/1994 | Brinton, Jr. et al. | 424/242.1 |
| 5,399,481 | 3/1995 | McMillan et al. | 435/7.1 |

FOREIGN PATENT DOCUMENTS

93/19090  9/1993  WIPO .

OTHER PUBLICATIONS

Watson, Wendy, J. et al., "Identification of a Gene Essential for Piliation in *Haemophilus influenzae* Type b with Homology to the Pilus Assembly Platform Genes of Gram–Negative Bacteria," *Infection and Immunity* 62(2):468–475 (1994).
van Ham, S. M. et al., "Phase Variation of *H. influenzae* Fimbriae: Transcriptional Control of Two Divergent Genes through a Variable Combined Promoter Region," *Cell* 73:1187–1196 (1993).
van Alphen, L. et al., "Blocking of Fimbria–Mediated Adherence of *Haemophilus influenzae* by Sialyl Gangliosides," *Infection and Immunity* 59(12):4473–4477 (1991).
Strom, M.S. et al., "A Single Bifunctional Enzyme, PilD, Catalyzes Cleavage and N–methylation of Proteins Belonging to the Type IV Pilin Family," *Proc. Natl. Acad. Sci. USA* 90:2404–2408 (1993).
St. Geme, J.W., III et al., "High–Molecular–Weight Proteins of Nontypable *Haemophilus influenzae* Mediate Attachment to Human Epithelial Cells," *Proc. Natl. Acad. Sci. USA* 90:2875–2879 (1993).

Sinha, N.D. et al., "Polymer Support Oligonucleotide Synthesis XVIII$^{1,2}$:Use of β–cyanoethyl–N, N–dialkylamino–/N–morpholino Phosphoramidite of Deoxynucleosides for the Synthesis of DNA Fragments Simplifying Deprotection and Isolation of the Final Product," *Nucleic Acids Research* 12(11):4539–4557 (1984).
Saiki, R.K. et al., "Primer–Directed Enzymatic Amplification of DNA With a Thermostable DNA Polymerase," *Science* 239:487–490 (1988).
Palmer, K.L. and Munson, R.S., Jr. "Construction of Chimaeric Genes for Mapping a Surface–Exposed Epitope on the Pilus of Non–typable *Haemophilus influenzae* Strain M37," *Molecular Microbiology* 6(18):2583–2588 (1992).
Musher, D.M. et al., "Pneumonia and Acute Febrile Tracheobronchitis Due to *Haemophilus influenzae*," *Annals of Internal Medicine* 99:444–450 (1983).
Miller, J.H. "Generalized Transduction; Use of P1 in Strain Construction," *Experiments in Molecular Genetics*, pp. 201–205 Cold Spring Harbor Laboratory, Cold Spring Harbor, NY (1972).
McCaman, M.T. et al., "Genetics and Regulation of Peptidase N in *Escherichia coli* K–12," *Journal of Bacteriology* 152(2):848–854 (1982).
Laemmli, U.K., "Cleavage of Structural Proteins During the Assembly of the Head of Bacteriophage T4," *Nature* 227:680–685 (1970).
Karasic, R.B. et al., "Evaluation of Pilus Vaccines for Prevention of Experimental Ptitis Media Caused by Nontypable *Haemophilus influenzae*," *Pediatr. Infect. Dis. J* 8(1):S062–S065 (1989).
Kar, S. et al., "Cloning and Expression in *Escherichia coli* of LKP Pilus Genes from a Nontypeable *Haemophilus influenzae* Strain," *Infection and Immunity* 58(4):903–908 (1990).

(List continued on next page.)

*Primary Examiner*—W. Gary Jones
*Assistant Examiner*—Debra Shoemaker
*Attorney, Agent, or Firm*—Hamilton, Brook, Smith & Reynolds, P.C.

[57] ABSTRACT

The invention relates to the isolation and cloning of the structural gene, hipP, for the NTHi pili serotype 5 and the LKP operon. The invention relates to DNA molecules capable of hybridizing to the DNA sequences of the *Haemophilus influenzae* genome related to the pili. The invention further relates to a DNA molecule which encodes a pili protein, particularly a tip adhesion protein. The DNA molecules of the invention can be used in a method for assaying a sample, such as a blood sample, for the presence of *Haemophilus influenzae* in the sample. Accordingly, the invention further relates to the use of the DNA molecules as a diagnostic. The invention also relates to a recombinant *Haemophilus influenzae* pili protein, such as a tip adhesion protein. The protein can be employed in a method for immunizing an animal, such as a human, as a therapeutic or diagnostic.

13 Claims, 14 Drawing Sheets

OTHER PUBLICATIONS

Gilsdorf, J.R., "Cloning, Expression, and Sequence Analysis of the *Haemophilus influenzae* Type b Strain M43p+ Pilin Gene," *Infection and Immunity* 58(4):1065–1072 (1990).

Forney, L.J. et al., "Comparison and Analysis of the Nucleotide Sequences of Pilin Genes from *Haemophilus influenzae* Type b Strains Eagan and M43," *Infection and Immunity* 59(6):1991–1996 (1991).

Coleman, T. et al., "Molecular Cloning, Expression, and Sequence of the Pilin Gene from Nontypeable *Haemophilus influenzae* M37," *Infection and Immunity* 59(5):1716–1722 (1991).

Chang, A.C.Y. and Cohen, S.N. "Construction and Characterization of Amplifiable Multicopy DNA Cloning Vehicles Derived from the P15A Cryptic Miniplasmid," *Journal of Bacteriology* 134(3):1141–1156 (1978).

Brinton, C.C., Jr. et al., "Design and Development of Pilus Vaccines for *Haemophilus influenzae* Diseases," *Pediatr. Infect. Dis. J.* 8(1):S54–S61 (1989).

Bluestone, C.D. and Klein, J.O., "Otitis Media With Effusion, Atelectasis, and Eustachian Tube Dysfunction," *Pediatric Otolaryngology* pp. 356–512 (1983).

Haslam, D. et al., "The Amino–Terminal Domain of the P–Pilus Adhesion Determines Receptor Specificity," *Journal of Cellular Biochemistry Supplement* 18A:47, Abstract B112 (1994).

Langermann S. and Wright A., "Molecular Analysis of the *Haemophilus Influenzae* Type b Pilin Gene,", *Molecular Microbiology*, 4(3):221–230 (1990).

van Ham, S.M. et al., "The Fimbrial Gene Cluster of *Haemophilus Influenzae* Type b," *Molecular Microbiology*, 13(4):673–684 (1994).

Lindberg, F. et al., "Gene Products Specifying Adhesion of Uropathogenic *Escherichia Coli* Are Minor Components of Pili," *Proc. Natl. Acad. Sci. USA,* 83:1891–1895 (1986).

Watson, W.J., et al., "Identification of a Gene Essential for Piliation in *Haemophilus Influenzae* Type b With Homology to the Pilus Assembly Platform Genes of Gram–Negative Bacteria," *Database EMBL/GenBank/DDBJ on STRAND, ID=HIIFC, AC=U02932* (1994).

Smith, A.L., "hif B of *H. Influenzae* is a Member of the Chaperone Family," *Database EMBL/GenBank/DDBJ on STRAND, ID=HIHIFB, AC=X66606* (1992).

VanHam, S.M., et al., "Cloning and Expression in *Escherichia Coli* of *Haemophilus Influenzae* Fimbral Genes Establishes Adherence to Oropharyn–Geal Epithelial Cells," *EMBO J.,* 8:3535–3540 (1989).

Green, B.A., et al., "Sequence of LKP Serotype 5 hifA Gene," *Database EMBL/GenBank/DDBJ on STRAND, ID=HII9795, AC=U19795* (1995).

Langerman and Wright, Molecular Microbiology 4: 221–230, Cited in SN 08277231, 1990.

Sambrook et al. In Molecular Cloning: A Laboratory Manual, Cited in SN 08277231, 1989.

```
                    10         20         30         40         50         60         70
                    *          *          *          *          *          *          *
LKP1 h1fA   MEQPIMKKIT TGSLILLAFA TNAADPQVST ETSGKVTFPG KVVENTCKVK TDSRNMSVVL NDVGKNHLKT
LKP4 h1fA   ..........L.......... .......... G.-VQADIN.. .......... .......EH. L.......S.S.
[646]
LKP5 h1fA   ..........L.......... .......... G.VQAADPNP ...K......Y .......... .........A.SQ
[618]

80         90        100        110        120        130        140
                    *          *          *          *          *          *          *
LKP1 h1fA   KKDIAMPTPP TINLENCSTT TTTNNKPVAT KVGAYFYSWK NADENNEYTL KNIKSGNDAA QNVNIQTFDA
LKP4 h1fA 70 .VN....... ..T.Q..DP. .ANGTANK.N ....L..... .V.KE.NF.. ..EQTIA.Y. T......LMES
[646]
LKP5 h1fA 80 .GY....... ..T..G.NAN .G..--..K.N ...V...... N....KE.S.. .S.LT.T.K. D....I.QE
[618]

150        160        170        180        190        200        210
                    *          *          *          *          *          *          *
LKP1 h1fA   NGTDAIRVVG NGTIDFTHSN TNDVATQQTV NKNHISGKAT INGENNVKIH YIARYYATAQ AEAGKVESSV
LKP4 h1fA140 ...K..S... KE.E..M.T. N.G..LN...P .NT.....STQ LT.T.ELP.. F..Q.....NK .T....Q...
[646]
LKP5 h1fA140 ......G.AD KTID......K. NGSTNSDKP- T......SATA L.NQGDIA.. ......O... GM.S...GPT..
[618]

LKP1 h1fA   DFQIAYE*
            *
LKP4 h1fA210 ........
[646]
LKP5 h1fA210 ..P.....
[618]
```

Figure 1

```
AAGCTTGCATGCCTGCAGGTCGACTCTAGAGGATCATTCCATTGTGTTTTATCTTTTAATAAACACCAAGGT
GAGGTAGAAATATTCAGTTCATCAAGCAAGGATTTTTGCGTAAAACGATCGGCTAATAATCCAAATACATGT
TGATTAACGAAGTTTTTATGATTGCTGAGTAATTCAGTCAAAGGCGTTTTTTCCCAGCGTTCAATTTCCGCC
GTGATGATCGCATTTTCAGGTAAGTCAAAAACTGGCGCATTGAAGGCTAAGGGTTCAACATAAATATCTAAA
GGTGCACCAGCGTAACCTAACATTCTGCCGAGTTGTCCGTTGCCGAGAACATAAACGGTTGGGTATAAGGTG
GAGTTTTGCATAATATTTCTCGTTAAATTTACGAAAAAACAACCGCACTTTAAAAGTGCGGTCAGATCTGAA
GATATTTTTATGTGCGTGGATCGGGATTGTCCAGTACAGCACGAGTTTGGCTTTCACGGAAAGATTGCAAGC
GTGAAAGCAATTCTGCATCCCAACCTGCTAGAATTTGGGCTGCTAACAACCCAGCATTTGCCGCGCCTGCAG
AGCCAATCGCTAATGTTCCGACTGGAATCCCTTTTGGCATTTGCACAATTGAATAAAGGCTATCCACACCAC
TTAACATAGAACTTTTTACTGGCACCCCAGCACTGGCACAAGTGTTTGGCTGCGATCATACCAGGTAAAT
GTGCCGCACCGCCTGCACCAGCAATAATTACTTTATAGCCATTTTTTGTGCATTTTCGGCAAATTCGAAAA
GTTTATCAGGCGTACGATGGGCAGAGACGACTTCCACATGATAAGGCACGTTAATTCATCTAAAATCTGAG
TTGCCTCTTGCATAGTAGCCCAATCACTTTTTGACCCCATCACAACGGCAATTTGTGCAGTTTTTGACATGC
TATTTTCTCAATTTTCTAATTAAAAACGTGGTGTAGAATAGCATAGATTACATATATCGAGCAAACGTTTGC
TATTTATGTACGTATTAATGGGGATTATTTTATAATTATTTGATTTTAAATTTTAGTAACTATACTTGATA
CCAAATTAATGGGCGATAGTTTATATGGGACGAACTGAAAAATTATTAGATAAGCTCGCACAATCAAAATCT
ACATTTAATTGGAATGAATTAGTTTCTTTGTTAGCTCAACAAGGTTATGAAAAGCGAGAAATGGCAGGTTCT
CGAGTGAGATTTTATAATAGAACACTCGAACATATGATTTTGTTACACAAGCCTCATCCTGAAAATTATATT
AAAGGCGGTGTTTTAAAGTCAGTGAAAGAATCATTAAAACAGGTAGGTATTCTATGAAGTTATTAAATTATA
AAGGTTATGTTGGCACGATTGAGGCGGATTTAGAAAACAATATATTATTTGGCAAACTTGCTTACATTCGTG
ATTTAGTGACTTACGAAGCAGAGTCATTATCTGAGTTAGAAAAAGAATTTCATCAATCTGTTGATTTATATT
TACAAGATTGTTTGGAATTAGGTAAAGAACCGAATAAGCCTTTTAAAGGTGTATTTAATGTACGAATTGGCG
AGGAATTGCATAGAGAAGCAACGATCATAGCTGGCGATCGTTCTCTTAATGCTTTTGTGACGGAAGCAATTA
AAGAAAAAATTTTTCGTGAAAAACCAAGTTTAAGATAACAAAACGTATTTACATTTTTTTCATCACGTAGG
CTGGGCGTAAGCCCATGTAGAGACACATAAAAAAGATTTGTAGGCTAGGCGTAAGCTCACGTGGATACATAT
AAAAAAGATTTGTAGGGTGGGCGTAAGCCCACGCAGGATATAACAAACACGTGGGCTTAGATTGCATTACAT
TAGGAATTATTCGTAAGCAATTTGGAAATCAACTGAGGATTCTACTTTACCAGCTTCCGCTTGAGCTGTTGC
```
◄ GluTyrAlaIleGlnPheAspValSerSerGluValLysGlyAlaGluAlaGlnAlaThrAla
ATAGTATCTAGCGATATAGTGTAATTTCACATTGTTTTCACCGTTAATTGTAGCTTTTCCTGAAATATGATT
◄ TyrTyrArgAlaIleTyrHisLeuLysValAsnAsnGluGlyAsnIleThrAlaLysGlySerIleHisAsn
TTTATTCACAGTTTGTTGTGTTGCAACGTCATTTGTATTGCTATGCGTAAAATCTGTTGTTCCGTTGCCGAC
◄ LysAsnValThrGlnGlnThrAlaValAspAsnThrAsnSerHisThrPheAspThrThrGlyAsnGlyVal
AACTTCAATTGCATCTGTACCATTAGCATCAAAAGCTGGATATTAACATTCTGTGCAGCATCATTTCCTGA
◄ ValGluIleAlaAspThrGlyAsnAlaAspPheLeuGlnIleAsnValAsnGlnAlaAlaAspAsnGlySer
TTTTGTATTTTTAATGTATATTCATTATTTCATCTGCATTTTCCAAGAATAGAAATAAGCTCCAACTTT
◄ LysThrAsnLysLeuThrTyrGluAsnAsnGluAspAlaAsnLysTrpSerTyrPheTyrAlaGlyValLys
TGTTGCAACAGGCTTATTATTAGTAGTAGTAGTAGAACAATTTTCTAAATTAATTGTAAATGGTGTTGG
◄ ThrAlaValProLysAsnAsnThrThrThrThrThrSerCysAsnGluLeuAsnIleThrPheProThrPro

Figure 2A

```
CATCGCTGTATCTTTTTTAGTTTTTAAATGATTTTTACCCACATCATTTAATACTACGCTCATATTTTTACT
```
◄ MetAlaThrAspLysLysThrLysLeuHisAsnLysGlyValAspAsnLeuValValSerMetAsnLysSer
```
ATCCGTTTTCACTTTACAAGTATTCTCAACAACCTTACCAAAGAAAGTAACTTTACCAGATGTTTCAGTACT
```
◄ AspThrLysValLysCysThrAsnGluValValLysGlyPhePheThrValLysGlySerThrGluThrSer
```
TACTTGAGGATCAGCAGCATTCGTTGCAAATGCCAATAAAATTAAGCTACCAAGAAGTGTTTTTTTCATAAT
```
◄ ValGlnProAspAlaAlaAsnThrAlaPheAlaLeuLeuIleLeuSerGlyLeuLeuThrLysLysMetIle
```
AAATTGCTCCATAAAGAGGTTTGTGCCTTATAAATAAGGCAATAAAGATTAATATAAACCGTTTATTAAAAT
```
◄ PheGlnGluMet
```
GCCAAAGGCTTAATAAACAGCAAACTTTGTTTTCCCAAAAAAAGTAAAAAACTCTTCCATTATATATATATA
TATATATAATTAAAGCCCTTTTTGAAAAATTTCATATTTTTTTGAATTAATTCGCTGTAGGTTGGGTTTTTG
CCCACATGGAGACATATAAAAAAGATTTGTAGGGTGGGCGTAAGCCCACGCGGAACATCATCAAACAACTGT
AATGTTGTATTAGGCACGGTGGGCTTATGCCTCGCCTACGGGGAAATGAATAAGGATAAATATGGGCTTAGC
```
► MetAsnLysAspLysTyrGlyLeuSer
```
CCAGTTTATGGATTTAATTATGTTGAAATGGGGAAAACAATGTTTAAAAAAACACTTTTATTTTTTACCGCA
```
► ProValTyrGlyPheAsnTyrValGluMetGlyLysThrMetPheLysLysThrLeuLeuPhePheThrAla
```
CTATTTTTTGCCGCACTTTGTGCATTTTCAGCCAATGCAGATGTGATTATCACTGGCACCAGAGTGATTTAT
```
► LeuPhePheAlaAlaLeuCysAlaPheSerAlaAsnAlaAspValIleIleThrGlyThrArgValIleTyr
```
CCCGCTGGGCAAAAAAATGTTATCGTGAAGTTAGAAAACAATGATGATTCGGCAGCATTGGTGCAAGCCTGG
```
► ProAlaGlyGlnLysAsnValIleValLysLeuGluAsnAsnAspAspSerAlaAlaLeuValGlnAlaTrp
```
ATTGATAATGGCAATCCAAATGCCGATCCAAAATACACCAAAACCCCTTTTGTGATTACCCCGCCTGTTGCT
```
► IleAspAsnGlyAsnProAsnAlaAspProLysTyrThrLysThrProPheValIleThrProProValAla
```
CGAGTGGAAGCGAAATCAGGGCAAAGTTTGCGGATTACGTTCACAGGCAGCGAGCCTTTACCTGATGATCGC
```
► ArgValGluAlaLysSerGlyGlnSerLeuArgIleThrPheThrGlySerGluProLeuProAspAspArg
```
GAAAGCCTCTTTTATTTTAATTTGTTAGATATTCCGCCGAAACCTGATGCGGCATTTCTGGCAAAACACGGC
```
► GluSerLeuPheTyrPheAsnLeuLeuAspIleProProLysProAspAlaAlaPheLeuAlaLysHisGly
```
AGCTTTATGCAAATTGCCATTCGCTCACGTTTGAAGTTGTTTTATCGCCCTGCGAAACTCTCGATGGATTCT
```
► SerPheMetGlnIleAlaIleArgSerArgLeuLysLeuPheTyrArgProAlaLysLeuSerMetAspSer
```
CGTGATGCAATGAAAAAAGTAGTGTTTAAAGCCACACCTGAAGGGGTGTTGGTGGATAATCAAACCCCTTAT
```
► ArgAspAlaMetLysLysValValPheLysAlaThrProGluGlyValLeuValAspAsnGlnThrProTyr
```
TATATGAACTACATTGGTTTGTTACATCAAAATAAACCTGCGAAAAATGTCAAATGGTTGCCCCTTTTTCT
```
► TyrMetAsnTyrIleGlyLeuLeuHisGlnAsnLysProAlaLysAsnValLysMetValAlaProPheSer
```
CAAGCGGTATTTGAAGCCAAAGGCGTGCGTTCTGGCGATAAATTGAAATGGGTATTGGTTAATGATTACGGT
```
► GlnAlaValPheGluAlaLysGlyValArgSerGlyAspLysLeuLysTrpValLeuValAsnAspTyrGly
```
GCCGACCAAGAAGGCGAAGCCATCGCTCAATAATAGCGAACTAGTGTAGGGTGGGCTTTAGACCACCGATTA
```
► AlaAspGlnGluGlyGluAlaIleAlaGln
```
ACCATAACAAAGGTGGGCTGAAGCCCACCCTACAACCACAAAGAACGATTAATCTGTGAAAACAAAAATTTT
TCCCTTAAATAAAATTGCGTTTGCTTGTTCACTGCTATTGGCAAATCCTTTAGCGTGGGCGGGAGATCAATT
TGATGCCTCTCTTTGGGGAGATGGTTCGGTGTTGGGCGTTGATTTTGCCCGATTTAATGTAAAAAATGCCGT
GTTACCAGGGCGTTATGAAGCTCAAATCTATGTGAAATTTGAAGAAAAAGGCGTAAGCGATATTATTTTTGC
```

Figure 2B

```
TGATAATCCTGCCACAGGTCGGACAGAATTATGCTTTACGCCTAAACTTCAAGAAATGCTGGATTTGATGGA
                                                           ► MetLeuAspLeuMetAs
TGAAGCCATTGTGAAATCGCCCAATTCAGAAGATGACACTTGTGTCTTTGCTTCTGATGCTATTCCTAAAGG
► pGluAlaIleValLysSerProAsnSerGluAspAspThrCysValPheAlaSerAspAlaIleProLysGl
CACGTTTGAATATCAAAGCGGCGAAATGAAATTGAAACTTGAGCTCCCTCAAGCTCTCACTATTCGCCGACC
► yThrPheGluTyrGlnSerGlyGluMetLysLeuLysLeuGluLeuProGlnAlaLeuThrIleArgArgPr
AAGAGGCTATATTGCGCCATCTCGCTGGCAAACTGGCACCAATGCCGCTTTTGCAAATTACGATATCAACTA
► oArgGlyTyrIleAlaProSerArgTrpGlnThrGlyThrAsnAlaAlaPheAlaAsnTyrAspIleAsnTy
TTATCGTTCTGGTAATCCCGAAGTAAAATCCGAAAGTTTGTATGTGGGCTTGCGTAGTGGCGTAAATTTTGG
► rTyrArgSerGlyAsnProGluValLysSerGluSerLeuTyrValGlyLeuArgSerGlyValAsnPheGl
CAACTGGGCATTGCGTCATAGCGGCAGTTTTAGCCGTTTTGAAAACCAAAGTAGCTCGGGTTTTACTGATAA
► yAsnTrpAlaLeuArgHisSerGlySerPheSerArgPheGluAsnGlnSerSerSerGlyPheThrAspLy
GGGCAAAAATCATTACGAACGTGGCGATACCTATTTACAACGAGATTTCGCCCTGCTTCGTGGCAATGTCAC
► sGlyLysAsnHisTyrGluArgGlyAspThrTyrLeuGlnArgAspPheAlaLeuLeuArgGlyAsnValTh
TGTTGGGGATTTTTTCAGCACTGCCCGCATTGGCGAAAATTTTGGTATGCGTGGTTTGCGTATTGCCTCTGA
► rValGlyAspPhePheSerThrAlaArgIleGlyGluAsnPheGlyMetArgGlyLeuArgIleAlaSerAs
TGATAGAATGCTTGCCCCATCACAACGTGGTTTTGCCCCAGTGGTGCGTGGCGTGGCAAACACAAACGCCAA
► pAspArgMetLeuAlaProSerGlnArgGlyPheAlaProValValArgGlyValAlaAsnThrAsnAlaLy
AGTCAGCATCAAACAAAATGGCTATACGATTTATCAAATCACCGTTCCCGCAGGGCCTTTCGTGATTAACGA
► sValSerIleLysGlnAsnGlyTyrThrIleTyrGlnIleThrValProAlaGlyProPheValIleAsnAs
TTTGTATGCCAGCGGTTATAGCGGCGATTTAACGGTGGAAATCCAAGAAAGTGATGGTAAAGTGCGGTCATT
► pLeuTyrAlaSerGlyTyrSerGlyAspLeuThrValGluIleGlnGluSerAspGlyLysValArgSerPh
TATTGTGCCGTTTTCTAATCTTGCCCCGTTAATGCGTGTGGGGCATTTGCGTTATCAATTAGCTGGCGGACG
► eIleValProPheSerAsnLeuAlaProLeuMetArgValGlyHisLeuArgTyrGlnLeuAlaGlyGlyAr
TTATCGAATTGACAGCCGCACCTTTGATGAACGTGTGTTACAAGGCGTGTTGCAATATGGTTTAACTAATCA
► gTyrArgIleAspSerArgThrPheAspGluArgValLeuGlnGlyValLeuGlnTyrGlyLeuThrAsnHi
TCTCACGCTGAATTCAAGCCTGCTTTATACACGTCATTATCGTGCAGGGCTGTTTGGTTTTGGTTTAAATAC
► sLeuThrLeuAsnSerSerLeuLeuTyrThrArgHisTyrArgAlaGlyLeuPheGlyPheGlyLeuAsnTh

GCCGATTGGGGCGTTTTCTGCTGATGCCACTTGGTCGCACGCTGAATTTCCGCTAAAACATGTGAGCAAAAA
► rProIleGlyAlaPheSerAlaAspAlaThrTrpSerHisAlaGluPheProLeuLysHisValSerLysAs
CGGCTACAGCTTGCACGGCAGTTATAGTATTAACTTCAATGAAAGTGGCACCAATATCACGTTGGCAGCCTA
► nGlyTyrSerLeuHisGlySerTyrSerIleAsnPheAsnGluSerGlyThrAsnIleThrLeuAlaAlaTy
TCGCTATTCTTCACGGGATTTTTACACCTTAAGCGACACCATTGGTCTTAACCGCACTTTCAGACAATTTAG
► rArgTyrSerSerArgAspPheTyrThrLeuSerAspThrIleGlyLeuAsnArgThrPheArgGlnPheSe
CGGTGCGTATTTGCCTGAAATTTACCGCCCAAAAAATCAGTTTCAAGTGAGTTTAAGCCAAAGTCTGGGGAA
► rGlyAlaTyrLeuProGluIleTyrArgProLysAsnGlnPheGlnValSerLeuSerGlnSerLeuGlyAs
TTGGGGAAATCTCTATCTTTCAGGACAAACCTATAATTATTGGGAAAAACGTGGCACGAATACGCAATATCA
► nTrpGlyAsnLeuTyrLeuSerGlyGlnThrTyrAsnTyrTrpGluLysArgGlyThrAsnThrGlnTyrGl
```

Figure 2C

```
            AGTTGCCTATTCAAACAGCTTCCACATTCTTAATTACTCTGTAAACCTCTCACAGAGTATTGATAAAGAAAC
▶ nValAlaTyrSerAsnSerPheHisIleLeuAsnTyrSerValAsnLeuSerGlnSerIleAspLysGluTh
            GGGCAAACGTGACAACAGCATTTATTTAAGTCTCAGCCTGCCATTAGGCGATAACCATTCTGCAGATAGTAG
▶ rGlyLysArgAspAsnSerIleTyrLeuSerLeuSerLeuProLeuGlyAspAsnHisSerAlaAspSerSe
            TTATTCTCGCAGTGGTAACGATATTAACCAACGACTTGGCGTAAATGGCTCTTTTGGTGAACGTCATCAATG
▶ rTyrSerArgSerGlyAsnAspIleAsnGlnArgLeuGlyValAsnGlySerPheGlyGluArgHisGlnTr
            GAGTTATGGTATTAACGCTTCACGCAATAATCAAGGCTATCGCAGTTATGACGGTAATCTTTCGCATAACAA
▶ pSerTyrGlyIleAsnAlaSerArgAsnAsnGlnGlyTyrArgSerTyrAspGlyAsnLeuSerHisAsnAs
            TAGCATTGGTAGTTACCGTGCTTCTTATTCACGTGATAGCCTCAAAAATCGCTCCATCTCACTGGGCGCAAG
▶ nSerIleGlySerTyrArgAlaSerTyrSerArgAspSerLeuLysAsnArgSerIleSerLeuGlyAlaSe
            CGGTGCTGTCGTGGCGCACAAACACGGTATTACCTTAAGCCAACCTGTTGGCGAAAGTTTTGCCATTATTCA
▶ rGlyAlaValValAlaHisLysHisGlyIleThrLeuSerGlnProValGlyGluSerPheAlaIleIleHi
            CGCCAAAGATGCCGCAGGAGCAAAAGTGGAATCAGGTGCCAATGTGAGCCTTGATTATTTCGGCAATGCGGT
▶ sAlaLysAspAlaAlaGlyAlaLysValGluSerGlyAlaAsnValSerLeuAspTyrPheGlyAsnAlaVa
            TATGCCTTACACCAGCCCGTATGAAATCAATTATATCGGTATCAATCCATCTGATGCGGAGGCGAATGTGGA
▶ lMetProTyrThrSerProTyrGluIleAsnTyrIleGlyIleAsnProSerAspAlaGluAlaAsnValGl
            ATTTGAAGCCACTGAACGCCAAATCATTCCTCGTGCAAATTCAATTAGCTTAGTAGATTTCCGCACGGGCAA
▶ uPheGluAlaThrGluArgGlnIleIleProArgAlaAsnSerIleSerLeuValAspPheArgThrGlyLy
            AAATACAATGGTGTTATTTAACCTCACTTTGCCAAATGGCGAGCCAGTGCCAATGGCATCCACCGCACAAGA
▶ sAsnThrMetValLeuPheAsnLeuThrLeuProAsnGlyGluProValProMetAlaSerThrAlaGlnAs
            TAGCGAAGGGGCATTTGTGGGCGATGTGGTGCAAGGTGGTGTGCTTTTCGCTAATAAACTTACCCAGCCAAA
▶ pSerGluGlyAlaPheValGlyAspValValGlnGlyGlyValLeuPheAlaAsnLysLeuThrGlnProLy
            AGGCGAGTTAATCGTCAAATGGGGTGAGCGAGAAAGCGAACAATGCCGTTTCCAATATCAAGTTGATTTGGA
▶ sGlyGluLeuIleValLysTrpGlyGluArgGluSerGluGlnCysArgPheGlnTyrGlnValAspLeuAs
            TAACGCACAAATACAAAGTCACGATATTCAATGCAAAACCGCAAAATAAATAATTGAAGAGGATTTATGCAA
▶ pAsnAlaGlnIleGlnSerHisAspIleGlnCysLysThrAlaLys                    ▶ MetGln
            AAAACACCCAAAAAATTAACCGCGCTTTTCCATCAAAAATCCACTGCTACTTGTAGTGGAGCAAATTATAGT
▶ LysThrProLysLysLeuThrAlaLeuPheHisGlnLysSerThrAlaThrCysSerGlyAlaAsnTyrSer
            GGAGCAAATTATAGTGGCTCAAAATGCTTTAGGTTTCATCGTCTGGCTCTGCTTGCTTGCGTGGCTCTGCTT
▶ GlyAlaAsnTyrSerGlySerLysCysPheArgPheHisArgLeuAlaLeuLeuAlaCysValAlaLeuLeu
            GATTGCATTGTGGCACTGCCTGCTTATGCTTACGATGGCAGAGTGACCTTTCAAGGGGAGATTTTAAGTGAT
▶ AspCysIleValAlaLeuProAlaTyrAlaTyrAspGlyArgValThrPheGlnGlyGluIleLeuSerAsp
            GGCACTTGTAAAATTGAAACAGACAGCCAAAATCGCACGGTTACCCTGCCAACAGTGGGAAAAGCTAATTTA
▶ GlyThrCysLysIleGluThrAspSerGlnAsnArgThrValThrLeuProThrValGlyLysAlaAsnLeu
            AGCCACGCAGGGCAAACCGCCGCCCCTGTGCCTTTTTCCATCACGTTAAAAGAATGCAATGCAGATGATGCT
▶ SerHisAlaGlyGlnThrAlaAlaProValProPheSerIleThrLeuLysGluCysAsnAlaAspAspAla
            ATGAAAGCTAATCTGCTATTTAAGGGGGAGACAACACAACAGGGCAATCTTATCTTTCCAATAAGGCAGGC
▶ MetLysAlaAsnLeuLeuPheLysGlyGlyAspAsnThrThrGlyGlnSerTyrLeuSerAsnLysAlaGly
```

Figure 2D

```
AACGGCAAAGCCACCAACGTGGGCATTCAAATTGTCAAAGCCGATGGCATAGGCACGCCTATCAAGGTGGAC
▶ AsnGlyLysAlaThrAsnValGlyIleGlnIleValLysAlaAspGlyIleGlyThrProIleLysValAsp
  GGCACCGAAGCCAACAGCGAAAAAGCCCCCGACACAGGTAAAGCGCAAAACGGCACAGTTATTCAACCCCGT
▶ GlyThrGluAlaAsnSerGluLysAlaProAspThrGlyLysAlaGlnAsnGlyThrValIleGlnProArg
  TTTGGCTACTTTGGCTCGTTATTACGCCACAGGTGAAGCCACCGCAGGCGACGTTGAAGCCACTGCAACTTT
▶ PheGlyTyrPheGlySerLeuLeuArgHisArg
  TGAAGTGCAGTATAACTAAAATATTTATTATCCAGTGAAAAAATGAATAAGAAATCGTATATAAATCATTAC
                                                   ▶ MetAsnLysLysSerTyrIleAsnHisTyr

TTAACTTTATTTAAAGTTACTACTTTACTATTTACTCTTTCAAGTAATCCTGTATGGGCAAATATAAAAACA
▶ LeuThrLeuPheLysValThrThrLeuLeuPheThrLeuSerSerAsnProValTrpAlaAsnIleLysThr
  GTTCAGGGAACAACTAGTGGTTTTCCACTTCTAACAAGAACTTTCACATTTAATGGCAATTTGCAATGGAAT
▶ ValGlnGlyThrThrSerGlyPheProLeuLeuThrArgThrPheThrPheAsnGlyAsnLeuGlnTrpAsn
  GTGAGTGCTCTACAACCAGCTTATATTGTTTCCTCTCAAGCAAGAGATAATCTTGATACAGTACATATTCAA
▶ ValSerAlaLeuGlnProAlaTyrIleValSerSerGlnAlaArgAspAsnLeuAspThrValHisIleGln
  TCTTCTGAAATTAATGCTCCAACAAATTCATTAGCTCCATTTAATAATTGGATTAATACGAAATCAGCAGTA
▶ SerSerGluIleAsnAlaProThrAsnSerLeuAlaProPheAsnAsnTrpIleAsnThrLysSerAlaVal
  GAGCTAGGTTATAGCTTTGCGGGCATTACTTGTACTAGTAATCCTTGCCCAACAATGAAATTACCATTATTA
▶ GluLeuGlyTyrSerPheAlaGlyIleThrCysThrSerAsnProCysProThrMetLysLeuProLeuLeu
  TTTCATCCTGATCTTACTAATTTAACTCCACCTGGAAAGAAAAATTCTGATGGAGGGGAGATTTTTAAATTA
▶ PheHisProAspLeuThrAsnLeuThrProProGlyLysLysAsnSerAspGlyGlyGluIlePheLysLeu
  CATAATGAATCTAATTTAGGCGTCTCTTTTCAAATTGGAGTAAAAACGAATACTTCTCTAGATTGGGTTAAT
▶ HisAsnGluSerAsnLeuGlyValSerPheGlnIleGlyValLysThrAsnThrSerLeuAspTrpValAsn
  GCTAAGAATAATTTTAGCTCTCTAAAAGTTTTAATGGTGCCTTTTAATTCTAGCGATAAAATATCTTTGCAT
▶ AlaLysAsnAsnPheSerSerLeuLysValLeuMetValProPheAsnSerSerAspLysIleSerLeuHis
  TTACGTGCTAAATTTCATTTATTAACAGATTTTTCATCGCTAAATAATGATATTACTATTGACCCTATGAAT
▶ LeuArgAlaLysPheHisLeuLeuThrAspPheSerSerLeuAsnAsnAspIleThrIleAspProMetAsn
  ACTAGTATAGGCAAAATTAATCTTGAAACGTGGCGTGGCTCAACAGGCAATTTTCTGTTAAATATGTAGGT
▶ ThrSerIleGlyLysIleAsnLeuGluThrTrpArgGlySerThrGlyAsnPheSerValLysTyrValGly
  GAGGATAAGGGAGATATATCTATTTTCTTTAATACACCTAAAATTATTCTAAAAAAACAACAACGCCGATGT
▶ GluAspLysGlyAspIleSerIlePhePheAsnThrProLysIleIleLeuLysLysGlnGlnArgArgCys
  ACTCTGAATAATGCTCCAGTGAGCCCAAATCCAGTTAAATTACGAGCGGTAAAAAAACGTGAATTGGAGGCA
▶ ThrLeuAsnAsnAlaProValSerProAsnProValLysLeuArgAlaValLysLysArgGluLeuGluAla
  CAAAGTGAAATGGAAGGTGGGACATTTCAGTTAAGAGTAAATTGTGACAATACCACTTATAATAAAGCCAAC
▶ GlnSerGluMetGluGlyGlyThrPheGlnLeuArgValAsnCysAspAsnThrThrTyrAsnLysAlaAsn
  GGCAAATGGTTATTTCCTGTAGTGAAAGTTACTTTTACGGACGAAGATGGTACAACGAATAATGGAACAAAT
▶ GlyLysTrpLeuPheProValValLysValThrPheThrAspGluAspGlyThrThrAsnAsnGlyThrAsn
```

Figure 2E

```
GACTTACTTCGCACCCAAACAGGCAGCGGACAAGCCACAGGCGTTAGCTTAAGAATCAAACGAGAAAATGGT
```
▸ AspLeuLeuArgThrGlnThrGlySerGlyGlnAlaThrGlyValSerLeuArgIleLysArgGluAsnGly
```
ACAGAAACCGTAAAATACGGTGCTGATTCTGCTCAAATGGGGAATGCTGGACAATTTGAATTACGAAAACAA
```
▸ ThrGluThrValLysTyrGlyAlaAspSerAlaGlnMetGlyAsnAlaGlyGlnPheGluLeuArgLysGln
```
CCATCCCCTGCTGGTGGAGATCAATATGCTGAAGAAACTTTCAAAGTCTATTACGTAAAAGACTCAACAAGA
```
▸ ProSerProAlaGlyGlyAspGlnTyrAlaGluGluThrPheLysValTyrTyrValLysAspSerThrArg
```
GGCACCTTAATCGAAGGAAAAGTCAAAGCCGCCGCCACTTTCACAATGTCATATCAATAATAATGTCGGGTG
```
▸ GlyThrLeuIleGluGlyLysValLysAlaAlaAlaThrPheThrMetSerTyrGln
```
GGAATATAAAGGCTGAAGGTTTAAACTTCAGTCTTTTTTTATAGGAAAATACCATTGCAACTTTAAGGATAA
AATTTTATCCTAAGCACAATTTTTATAAGAATAGGTCAAATTATGTTAGCCAAAGCAAAATATAGAAAAGAT
```
▸ MetLeuAlaLysAlaLysTyrArgLysAsp
```
TACAAACAACCAGATTTTACGGTCACAGACATTTATTTAGATTTTCAACTTGATCCTAAAAATACTGTGGTG
```
▸ TyrLysGlnProAspPheThrValThrAspIleTyrLeuAspPheGlnLeuAspProLysAsnThrValVal
```
ACTGCAACCACAAAATTCCAACGCTTAAATAATGAAGCGACGTCTTTACGTTTAGACGGGCATAGCTTCCAG
```
▸ ThrAlaThrThrLysPheGlnArgLeuAsnAsnGluAlaThrSerLeuArgLeuAspGlyHisSerPheGln
```
TTTTCTTCTATTAAATTTAATGGCGAGCCATTTTCTGATTATCAACAAGATGGCGAGAGTTTAACGCTCGAT
```
▸ PheSerSerIleLysPheAsnGlyGluProPheSerAspTyrGlnGlnAspGlyGluSerLeuThrLeuAsp
```
TTAAAAGACAAAAGTGCGGATGAATTTGAGCTTGAAATTGTGACGTTCCTTGTGCCAGCCGAAAATACGTCA
```
▸ LeuLysAspLysSerAlaAspGluPheGluLeuGluIleValThrPheLeuValProAlaGluAsnThrSer
```
TTACAAGGGCTATATCAGTCTGGCGAAGGTATTTGTACGCAATGTGAGGCGGAAGGTTTCCGTCAAATCACT
```
▸ LeuGlnGlyLeuTyrGlnSerGlyGluGlyIleCysThrGlnCysGluAlaGluGlyPheArgGlnIleThr
```
TATATGCTTGATCGTCCTGATGTGCTGGCGCGTTATATAATCAAAATTACGGCAGATAAAACCAAATATCCA
```
▸ TyrMetLeuAspArgProAspValLeuAlaArgTyrIleIleLysIleThrAlaAspLysThrLysTyrPro
```
TTCTTACTGTCGAATGGTAATCGCATTGCAAGTGGCGAATTAGAAGATGGTCGCCATTGGGTGGAATGGAAT
```
▸ PheLeuLeuSerAsnGlyAsnArgIleAlaSerGlyGluLeuGluAspGlyArgHisTrpValGluTrpAsn
```
GATCCTTTCCCAAAACCAAGCTATTTATTTGCTTTAGTGGCGGGAGATTNNGGTTTATTACAAGATAANTTT
```
▸ AspProPheProLysProSerTyrLeuPheAlaLeuValAlaGlyAspXaaGlyLeuLeuGlnAspXaaPhe
```
ATTACTAAAAGTGGTCGTGAAGTGGCTTTAGAGCTTTATGTGGATCGCGGTAATCTTAACCGTGCAACTGGG
```
▸ IleThrLysSerGlyArgGluValAlaLeuGluLeuTyrValAspArgGlyAsnLeuAsnArgAlaThrGly
```
GCAATGGAAAGTCTGAAAAAAGCGATGAAATGGGATGAAGATCGCTTTATTTTAGAATTTTACCTAGATATT
```
▸ AlaMetGluSerLeuLysLysAlaMetLysTrpAspGluAspArgPheIleLeuGluPheTyrLeuAspIle
```
TATATGATCGCGGCCGCCGATTCCTCCAATATGGGCGCAATGGAAAATAAAGGATTAAATATCTTTAACTCT
```
▸ TyrMetIleAlaAlaAlaAspSerSerAsnMetGlyAlaMetGluAsnLysGlyLeuAsnIlePheAsnSer
```
AAATTGGTGTTGGCAAATCCACAAACGGCAACAGATGAAGATTATCTTGTCATTGAAAGTGTGATTGCACAC
```
▸ LysLeuValLeuAlaAsnProGlnThrAlaThrAspGluAspTyrLeuValIleGluSerValIleAlaHis

Figure 2F

```
GAATATTCCCATAACTGGACGGGAAACCGTGTAACCCGCCGAGATGGGTTCAACTAGGTTTGAAGAAGGTTA
```
▶ GluTyrSerHisAsnTrpThrGlyAsnArgValThrArgArgAspGlyPheAsn
```
ACGGCTTCCGGGAACAAGATTTCTCAGATCAGTTCTCCGGGCCGGAACCGATTAATAAGGGAAAATTTTCCG
```

Figure 2G

CLJ11

CLJ10

CLJ12

KIEEGKLVIWINGDKGYNGLAEVGKKFEKDTGIKVTVEHPDKLEEKFPQVAATGDGPDIIF
WAHDRFGGYAQSGLLAEITPDKAFQDKLYPFTWDAVRYNGKLIAYPIAVEALSLIYNKDLL
PNPPKTWEEIPALDKELKAKGKSALMFNLQEPYFTWPLIAADGGYAFKYENGKYDKIKDVG
VDNAGAKAGLTFLVDLIKNKHMNADTDYSIAEAAFNKGETAMTINGPWAWSNIDTSKVN
YGVTVLPTFKGQPSKPFVGVLSAGINAASPNKELAKEFLENYLLTDEGLEAVNKDKPLGA
VALKSYEEELAKDPRIAATMENAQKGEIMPNIPQMSAFWYAVRTAVINAASGRQTVDEALK
DAQTRITKIEGRTLSSNPVWANIKTVQGTTSGFPLLTRTFTENGNLQWNVSALQPAYIVSSQ
ARDNLDTVHIQSSEINAPTNSLAPENNWINTKSAVELGYSFAGITCTSNPCPTMKLPLLFHP
OLTNLTPPGKKNSDGGEIFKLHNESNLGVSFQIGVKTNTSLDWVNAKNNFSSLKVLMVPF
NSSKSISLHLRAKFHLLTDFSSLNNDITIDPMNTSIGKINLETWRGSTGNFSVKYVGEDKG
DISIFFNTPKIILKKQQRRCTLNNAPVSPNPVKLRAVKKRELEAQSEMEGGTFQLRVNCDN
TTYNKAN

Figure 9

SEQUENCE AND ANALYSIS OF LKP PILIN STRUCTURAL GENES AND THE LKP PILI OPERON OF NONTYPABLE *HAEMOPHILUS INFLUENZAE*

RELATED APPLICATION

This application is a Continuation-In-Part of Ser. No. 08/277,231 filed Jul. 19, 1994 now U.S. Pat. No. 5,643,725, the contents of which is incorporated herein by reference.

BACKGROUND OF THE INVENTION

Nontypable *Haemophilus influenzae* (NTHi) are primarily noninvasive human respiratory tract pathogens. NTHi can reside in the respiratory tract as a commensal or give rise to local infections, including otitis media, bronchitis, sinusitis, and rarely, pneumonia (Bluestone, C. D., and J. O. Klein, *In Pediatric Otolaryngology.*, 356 (1983); Bluestone and Stool ed. W. B. Saunders Co. Philadelphia.; Musher, D. M. et al., *Ann. Intern. Med.* 99:344–350 (1983)). Several potential adherence factors have been described for *Haemophilus influenzae* (both typable and nontypable) adherence to human cells, including four classes of fimbriae/pili and two high molecular weight proteins with similarity to the filamentous hemagglutinin of *Bordetella pertussis* (St. Geme, J. W., et al., *Proc. Natl. Acad. Sci. USA* 90:2875–2879 (1993)). Pili are bacterial surface antigens. They are protein appendages consisting of a helically symmetrical assembly of major protein (pilin) subunits. Some pili can also carry from two to three minor proteins assembled on their tips. One of these proteins, adhesin, carries the active site for pilus adhesion to specific membrane receptors on human and animal cells.

One class of pili/fimbriae has been widely studied, the long thick positive (LKP) family. LKP pili are expressed by both typable and nontypable *H. influenzae* (Hib). The pili in this family have a characteristic morphology, partially shared adhesion specificity and their structural proteins share amino acid sequences. These pili are hemagglutination positive and mediate attachment to human mucosal cells (Brinton, C. C. et al., *Pediatr. Infect. Dis. J.* 8 Suppl.:54–61 (1989)). Hemagglutination of human erythrocytes is accomplished via binding to the AnWj blood group antigen while binding to epithelial cells involves a sialic acid containing lactosylceramide receptor (van Alphen, L. et al., *Infect. Immun.* 69:4473–4477 (1991)).

The LKP family has been divided into different strain specific serotypes based on reactivity to polyclonal antisera raised against the purified pili. Little cross reactivity among pili serotypes has been observed (Brinton, C. C., et al., *Pediatr. Infect. Dis. J.* 8 Suppl.:54–61 (1989)).

Inhibiting, or blocking, LKP pilus-mediated adhesion by *H. influenzae* to cells can prevent *H. influenzae* diseases. Purified, intact LKP pili have been shown to be vaccine candidates for NTHi otitis media in the chinchilla model, conferring protection against challenge with NTHi strains bearing homologous pili serotype (Karasic, R. et al., *Pediatr. Infect. Dis. J.* 8 (Suppl.): S62–65 (1988)). However, because protection is pilus-specific, for broad protection, a vaccine would be required to be multivalent, including the most frequently occurring serotypes of pili in the natural population of pathogens. LKP pilin structural genes have been cloned and sequenced by several groups (Coleman, T. et al., *Infect. Immun.* 59:1716–1722 (1991); Forney, L. J. et al., *Infect. Immun.* 59:1991–1996 (1991); Kar, S., et al. *Infect. Immun.* 58:903–908 (1990); van Ham, S. M., et al., *EMBO Jour.* 8:3535–3540 (1989)), but only the genes responsible for pili serotypes 1 and 4 have been identified.

SUMMARY OF THE INVENTION

The invention relates to the isolation, cloning and sequencing of the pilin gene for the *Haemophilus influenzae* pili serotype 5 (FIG. 1), to the sequencing of the entire LKP1 operon, which is set forth in FIGS. 2A–G, and to the cloning of the LKP10, LKP11, and LKP12 pili. The present invention also relates to DNA molecules (also referred to herein as DNA sequences or nucleic acid sequences) which encode proteins which comprise the *H. influenzae* LKP, particularly a tip adhesin protein. The present invention also relates to DNA molecules capable of hybridizing to the DNA sequences of the *Haemophilus influenzae* genome related to the pili. The DNA molecules of the present invention can be used in a method for assaying a sample, such as a blood sample, for the presence of *Haemophilus influenzae*. Accordingly, the present invention relates to the use of the DNA molecules as a diagnostic.

The present invention further relates to recombinant *Haemophilus influenzae* pili proteins, and peptides, specifically a tip adhesin protein. The proteins, or peptides, of the present invention can be used to produce antibodies, both polyclonal and monoclonal, which are reactive with (i.e., bind to) the *H. influenzae* pili proteins, and can be used in diagnostic assays to detect the presence of *Haemophilus influenzae* antibodies, in for example, a blood sample. Such antibodies to also be used as vaccines in methods of passive immunization.

The proteins and peptides of the present invention can also be employed in methods for immunizing a mammal, such as a human, against *Haemophilus influenzae* infection and, thus, as a vaccine for the prevention of *Haemophilus influenzae* related diseases, for example, otitis media. In particular, based on the DNA and amino acid sequences presented herein, an adhesin protein, or peptide, vaccine can be constructed which can induce protecting antibodies to *H. influenzae* in mammals.

BRIEF DESCRIPTION OF THE DRAWINGS

FIG. 1 is a graphic illustration of the conserved regions of the pilin structural proteins of *H. influenzae* serotypes 1, 4 and 5 (SEQ ID NOs:1–3, respectively).

FIGS. 2A–G show the DNA sequence (SEQ ID NO:4) of the LKP1 operon and the deduced amino acid sequences for the six open reading frames (SEQ ID NOs:5–10).

FIG. 9 shows the amino acid sequence of LKP1 fusion protein. The underline indicates the partial amino acid sequence of the LKP tip adhesin protein SEQ ID NO:11 that was fused to maltose-binding protein.

DETAILED DESCRIPTION OF THE INVENTION

Figure 3:
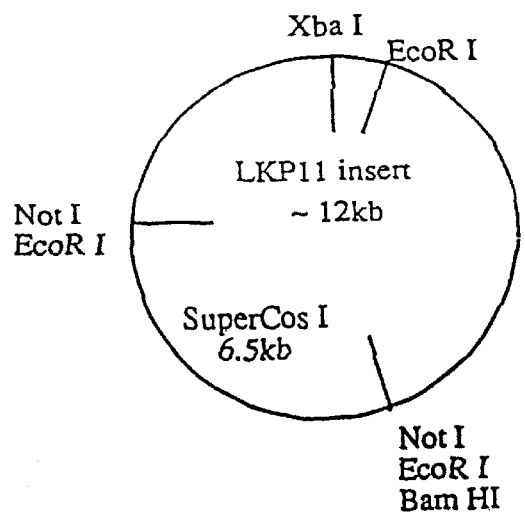
FIGS. 3, 4 and 5 are schematics of the physical maps obtained by restriction enzyme digestion of vectors containing LKP inserts.

Described herein, for the first time, is the cloning of the *Haemophilus influenzae* serotype 5 pilin gene and the sequence of the entire LKP1 operon. The LKP1 operon, as shown in FIGS. 2A–G, is composed of five separate genes, designated hipP (the pilin or pillin structural gene), hipC (the periplasmic chaperone gene), hipR (the membrane anchor gene), hipM (the minor tip associated protein gene) and hipA (the tip adhesin gene). These five genes are also referred to herein as hifA (for hipP), hifB (for hipC), hifC (for hipR), hifD (for hipM) and hifE (for hipA). Also present on the LKP1 operon are an integrase gene, and a peptidase gene. The proteins encoded by these genes of the LKP1 operon and the LKP5 pilin protein are collectively referred to herein as the *H. influenzae* pili proteins.

The present invention encompasses the isolated and/or recombinant nucleic acid sequences encoding the *H. influenzae* pili proteins, or biologically active fragments thereof, described herein. As used herein nucleic acids are also referred to as DNA and RNA, or DNA sequences and RNA sequences, or DNA molecules or RNA molecules. Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods known to those of skill in the art to obtain isolated nucleic acids and methods described herein. These isolated nucleic acids include essentially pure nucleic acids, nucleic acids produced by chemical synthesis, by combinations of biological and chemical methods, and recombinant nucleic acids which are isolated.

Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

Also encompassed by the present invention are nucleic acid sequences (DNA or RNA sequences) which are substantially complementary to the *H. influenzae* DNA sequences described herein, and nucleic acid sequences which hybridize with these DNA sequences under conditions of stringency known to those of skill in the art sufficient to identify DNA sequences with substantial nucleic acid sequence identity. It is reasonable to predict that DNA sequences identified under such stringent conditions will likely encode a protein (also referenced to herein as a polypeptide, or peptide fragment) with the biological activity of *H. influenzae* pili proteins. A general description of stringent hybridization conditions are discussed in Ausubel, F. M., et al., *Current Protocols in Molecular Biology*, Greene Publishing Assoc. and Wiley-Interscience 1989, the teachings of which are incorporated herein by reference. Factors such as probe length, base composition, percent mismatch between the hybridizing sequences, temperature and ionic strength influence the stability of nucleic acid hybrids. Thus, stringency conditions sufficient to identify additional *H. influenzae* pili proteins, (e.g., high or moderate stringency conditions) can be determined empirically, depending in part upon the characteristics of the known DNA to which other unknown nucleic acids are being compared for sequence similarity.

As defined herein, substantially complementary means that the sequence need not reflect the exact sequence of e.g., SEQ ID NO:4, but must be sufficiently similar in identity of sequence to hybridize with SEQ ID NO:4 under stringent conditions. For example, non-complementary bases, or longer or shorter sequences can be interspersed in sequences provided the sequence has sufficient complementary bases with, e.g., SEQ ID NO:4 to hybridize therewith.

The DNA molecules of the present invention can, preferably, encode a functional or biologically active pili protein, such as the pilin gene, hipP; the periplasmic chaperon, hipC; the membrane anchor protein, hipR; the tip associated protein, hipM and most preferably, the tip adhesin protein, hipA. A "functional or biologically active protein" is defined herein as a protein which shares significant identity (e.g., at least about 65%, preferably at least about 80% and most preferably at least about 95%) with the corresponding sequences of the endogenous protein and possesses one or more of the functions thereof. Biological functions of the *H. influenzae* pili proteins include antigenic structural, and adhesion properties. For example, as described in Karasic, R. et al. (Karasic, R. et al., *Pediatr. Infect. Dis. J.* 8 (*Suppl.*): S62–65 (1988)), the teachings of which are herein incorporated by reference, pili proteins can be shown to adhere to mucosal cells and erythrocytes. Thus, such adhesion properties can be a measure of biological activity. Also described herein, biological activity can include the antigenicity of the protein, or peptide, resulting in the production of antibodies which bind to the pili proteins.

The *H. influenzae* pili proteins of the present invention are understood to specifically include the proteins of the LKP1 operon and the serotype 5 hipP pilin protein, and proteins having amino acid sequences analogous to these sequences. Such proteins are defined herein as *H. influenzae* pili protein analogs, or derivatives. Analogous amino acid sequences are defined herein to mean amino acid sequences with sufficient identity of amino acid sequence with, e.g., LKP1 tip adhesin protein, to possess the biological activity of tip adhesin. The biological activity of tip adhesin can include, for example, the capability of tip adhesin to bind to specific membrane receptors on human and animal cells. For example, an analog polypeptide can be produced with "silent" changes in the amino acid sequence wherein one, or more amino acid residue differs from the amino acid residues of the LKP1 adhesin, yet still possess adhesion activity. Examples of such differences include additions, deletions or substitutions of residues to e.g., SEQ ID NO:9. Also encompassed by the present invention are analogous proteins that exhibit lesser or greater biological activity of the pili proteins of the present invention.

The present invention also encompasses biologically active protein, or biologically active fragments of the *H. influenzae* pili proteins described herein. Such fragments can include only a part of the full-length amino acid sequence of a pili protein yet possess biological activity. Such fragments can be produced by amino- and carboxyl-terminal deletions, as well as internal deletions. Such peptide fragments can be tested for biological activity as described herein. Thus, a functional, or biologically active, protein includes mutants or derivatives of the endogenous protein wherein one or more amino acids have been substituted, deleted or added. Also included are active fragments of the protein. The *H. influenzae* pili proteins, as set forth above, include functional or biologically active pili proteins, such as the pilin structural protein, hipP; the periplasmic chaperon, hipC; the membrane anchor protein, hipR; the tip associated protein, hipM; and most preferably, the tip adhesion protein, hipA.

The present invention further relates to fusion proteins comprising the pili proteins described herein (referred to herein as a first moiety) linked to a second moiety not occurring in the pili protein as found in nature. Thus, the second moiety can be a single amino acid, peptide or polypeptide. The first moiety can be in an N-terminal location, a C-terminal location or internal to the fusion protein. In one embodiment, the fusion protein comprises a pili protein and either a maltose binding protein (MBP) (SEQ ID NO:11) or glutathione-S-transferase (GST).

The DNA sequences of the present invention can also be used in a recombinant construct for the infection, transfection or transformation of a cell in vitro or in vivo under control of an appropriate promoter for the expression of functional *H. influenzae* pili proteins, as defined herein, in an appropriate host cell. Such recombinant constructs are also referred to herein as expression vectors. For example, a DNA sequence can be functionally ligated to a suitable promoter (e.g., a constitutive or inducible promoter or the endogenous promoter) introduced into a suitable expression vector, such as pUC19, which is then introduced into a suitable host cell. The construct can also include DNA encoding one or more selectable markers (such as neo, gpt, dhfr, ada, pac, hyg and hisd) or DNA encoding one or more different antigens or therapeutic proteins.

The construct can be introduced by any suitable means, as set forth above, such as by calcium phosphate precipitation, microinjection, electroporation or infection (such as with an infectious retroviral, herpes vaccinia or adenovirus vector). The host cell can be a eucaryotic or procaryotic cell. Suitable cells include bacterial (e.g. *E. coli*) or mammalian cells. Mammalian cells include primary somatic cells, such as, epithelial cells, fibroblasts, keratinocytes, macrophages or T cells, or immortalized cell lines, such as HeLa or HT1080. The recombinant host cell can then be cultured and, optionally, selected, in vitro under appropriate conditions resulting in the expression of the protein. Alternatively, the cell can be transplanted or injected into an animal, such as a human, for in vivo expression.

In one embodiment, the present invention relates to LKP type pili-producing *E. coli* recombinants. Such recombinants have been constructed from *Haemophilus infuenzae*, as described herein. These single serotype recombinants produced pili in large, easily purifiable quantities. They did not phase vary or become recalcitrant upon subculture and could be grown as *E. coli* in liquid medium with good pilus yields. The single serotype pilus preparations grown and purified from them contained pili identical to those on the parent *H. influenzae* (Hflu) strains and contained no other Hflu antigens. These preparations are easily standardized for purity, identity, concentration and potency for subsequent mixing into a multivalent vaccine and provides an efficient means of producing pilus for vaccine manufacture. As described herein, single-type-producing *E. coli* recombinant vaccine strains have been constructed for LKP10, LKP11 and LKP12 serotypes.

Multiple serotype recombinants containing two operons on separate plasmids have also been constructed. Single colonies of these strains simultaneously expressed, in good quantities, two serotypes of pili. However, these strains were unstable in that, during in vitro subculture, they tended to rapidly lose pilus expression, perhaps because the plasmids used were incompatible. When the two operons are placed on two compatible plasmids these strains are expected to be more stable. The use of stable, high-producing double-expressing recombinant strains could simply production of proteins suitable for vaccine use by reducing by half the number of vaccine strains required.

Good production, concentration and purification methods for Hflu LKP pili of different serotypes have been developed and are described herein. Pili can be purified from *E. coli* recombinant cultures producing Hflu pili as described for the purification of pili from Hflu culture. Both solid phase and liquid phase fermentation methods have been used. The preferred procedure involves mechanical removal of pili from the harvested bacteria and their separation from the bacterial cells by centrugation. Pili are concentrated and further purified by alternate cycles of longitudinal aggregation (crystallization) of intact pilus rods with soluble impurities removed by centrugation of the crystals followed by solubilization of the pilus crystals into free pilus rods with particulate impurities removed by centrugation. Each stage of the production/purification process was optimized for each pilus serotype. To date, nineteen different LKP serotypes have been purified.

Alternative pilus purification methods with analytical and industrial utility have also been developed Using appropriate solvent and column conditions, intact pili can be purified away from contaminating proteins by HPLC or FPLC on molecular sizing, hydrophobic or ion exchange columns. These methods are also capable of scale-up for industrial production.

Purification methods for individual pilus proteins have also been developed starting with intact LKP pili. Hflu LKP pilus structural proteins, as deduced from the multiple sequence alignment of pilus gene sequences with other pilus genes, include pilin, small tip minor and large tip minor proteins. The large tip minor protein is referred to as the "adhesin" because it carries the known LKP pilus adhesion specificity for human red blood cells. However, by analogy with other pilus families, the other two LKP pilus structural proteins may also be adhesins with specificities for as yet unknown human receptors. Both pilins and adhesins of LKP pili have been puried in biologically active form.

The pilins are purified in assembled rod form by removal of the minor tip proteins and separation of rods from minors on molecular sizing columns. In their assembled form, the pilin units retain the antigenic specificity of intact pili which is conferred by the exposed surface determinants of the pilin subunits on the lateral surface of the pilus rod. Pilin rods are expected to be equally as effective multivalent vaccine components as intact pili may have advantage of higher purity and possibly reduced side effects.

The adhesin of LKP11 has been isolated and purified in active and soluble form. Its removal from LKP11 pili eliminates the ability of these pili to bind to human red blood cells. In pure form it can bind to human red blood cell membranes. The adhesin band on SDS gels is labeled by antibodies reactive with fusion protein comprised of a fragment of adhesin and maltose binding protein. Purified LKP pilus adhesins may have utility as vaccine components capable of inducing adhesion-blocking or clearing antibodies. The LKP11 adhesin did not cross-react antigenically with the LKP1 adhesin on Western blots. Thus, the SDS/PAGE gel similarity of apparent molecular weights found for 3 different LKP adhesins was not predictive of antigenic similarity in this limited two-serotype test. Free adhesins can be tested for efficacy as otitis media vaccines and for their ability to induce adhesion-blocking antibodies. Antiserum to the fusion protein, which labeled the adhesin band on Western blots, did not block adhesion to red cells.

The isolated recombinant proteins of the present invention can be administered to a mammal to protect, or to treat the mammal against *H. influenzae* infection. Isolated recombinant pili protein can be formulated into a vaccine composition, for example, as described in U.S. Pat. No. 5,336,490, the teachings of which are incorporated herein by reference. The protein can also be administered via an infectious construct, preferably a replication incompetent or attenuated viral construct. Alternatively, the protein can be administered via a recombinant host cell (such as, a mammalian cell) which will express the protein in vivo or in a pharmaceutically acceptable carrier. In particular, the recombinant LKP1 tip adhesin protein, a biologically active fragment thereof, or a fusion protein, can be used in a vaccine composition to induce the production of antibodies in a mammal. It is reasonable to predict that such antibodies can protect the mammal from *H. influenzae* diseases.

The vaccine composition may be administered in a single dose or in more than one dose over a period of time to achieve a level of antibody in the blood which is sufficient to confer protection from *H. influenzae* infection.

Suitable pharmaceutical carriers include, but are not limited to water, salt solutions, alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. The pharmaceutical preparations can be sterilized and desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the active compounds. They can also be combined where desired with other active agents, e.g., enzyme inhibitors, to reduce metabolic degradation.

For parenteral application, particularly suitable are injectable, sterile solutions, preferably oily or aqueous solutions, as well as suspensions, emulsions, or implants, including suppositories. Ampoules are convenient unit dosages.

Modes of administration are those known in the art, such as parenteral, oral or intranasal administration or by cellular implantation.

It will be appreciated that the actual effective amounts of the protein in a specific case will vary according to the specific compound being utilized, the particular composition formulated, the mode of administration and the age, weight and condition of the patient, for example. As used herein, an effective amount of protein is an amount of protein which is capable of raising the level of antibody in a mammal to a level sufficient to provide protection from *H. influenzae* infection. Dosages for a particular patient can be determined by one of ordinary skill in the art using conventional considerations, (e.g. by means of an appropriate, conventional pharmacological protocol).

The DNA molecules and proteins of the present invention can be used in in vitro diagnostic assays to detect the presence of *H. influenzae* in biological samples. In one embodiment, the DNA molecules, or fragments thereof, can be used as probes in an assay for detecting *Haemophilus influenzae* in a sample, such as a blood sample from a mammal, e.g. a human. Such probes can be designed such that they specifically bind to the target sequence (e.g., an *H. influenzae* pili protein).

In one embodiment the DNA probe can comprise the nucleotides of a serotype conserved region of the *H. influenzae* genome, such as the nucleotides encoding a tip adhesin protein. To specifically bind to the target sequence, the probe must be of sufficient length to provide the desired specificity, i.e., to avoid being hybridized to random sequences in the sample. The DNA molecule capable of hybridization preferably contains at least about 400 nucleotides, more preferably at least about 1000 nucleotides, and most preferably at least about 1200 nucleotides. For example, the DNA molecule can comprise at least about 400 nucleotides between about nucleotide 7000 to 7400 of SEQ ID NO:4. The DNA hybridization probe preferably shares at least about around 70% homology or the corresponding sequences of the *Haemophilus influenzae* genome, more preferably at least about 80% and most preferably at least about 90%.

In particular, the DNA molecules of the present invention are capable of hybridizing to serotype conserved regions of the *H. influenzae* genome. A particularly preferred embodiment are DNA molecules that hybridize with the *H. influenzae* region encoding the tip adhesin protein. For example, a DNA molecule can be capable of hybridizing to the gene encoding the tip adhesin protein of serotype 1, preferably the sequence set forth between about nucleotide 6955 to 8265 of SEQ ID NO:4. In one embodiment, the DNA molecule is capable of hybridizing to the genome under stringent conditions, as described herein. The hybridization assay can be performed employing known hybridization procedures, such as those described herein. The probe can be, for example, detectably labeled employing known labels in the art, including enzymes, dyes, antibodies and radioactive labels. The probe is preferably immobilized on a solid support (e.g., a membrane).

Alternatively, the DNA molecule can be selected such that it hybridizes to a non-conserved region of the *Haemophilus influenzae* genome. For example, a DNA molecule that hybridizes to the gene encoding the pilin protein can be employed. Such an assay can detect the presence of a particular serotype of *Haemophilus influenzae* in the sample.

A sample which can be subjected to the present assay can be any sample which is suspected of containing or being contaminated with *Haemophilus influenzae*. Examples of such an sample include a blood sample, a nasopharyngeal sample, or an ear aspirate.

The assay can be used, therefore, as a diagnostic for the detection of infection of a subject, such as a mammal (e.g., a human), with *Haemophilus influenzae*. The assay can also be used to detect the presence of contamination of a material with *Haemophilus influenzae*, such as a food, medicament, or biological material.

In another embodiment, the protein can be used in an assay for detecting *Haemophilus influenzae* infection in a sample, such as a blood sample. For example, the pili of a pathogen can be isolated from the sample or recombinantly produced, employing the techniques described herein. One or more of the proteins, or fragments thereof, of the pili can then be sequenced. The sequences can be aligned to and compared with the corresponding protein sequence(s) of SEQ ID NO:4. Homology in excess of 90%, for example, is indicative of presence of the pathogen (i.e., infection) in the sample.

The pili protein, or a fragment thereof (e.g., a peptide fragment) can also be used in an immunoassay, specifically an ELISA, to detect the presence of antibodies in biological samples (e.g., blood, serum or tissue). Such immunoassay can be readily performed by those of skill in the art using well-established techniques to detect antibody bound to LKP pili protein or peptide fragments.

The pili proteins, or fragments thereof (also referred to herein as peptides, or peptide fragments), can also be used to produce antibodies that are reactive with the pili proteins described herein. The term antibody is intended to encompass both polyclonal and monoclonal antibodies. Polyclonal antibodies can be prepared by immunizing an animal with a preparation of crude or purified pili protein using techniques well-known to those of skill in the art. Pili fusion proteins can also be used for immunization. Monoclonal antibodies can be prepared using techniques known to those of skill in the art. These antibodies can be used in diagnostic assays to detect the presence of *H. influenzae* antibodies in biological samples as described above.

The invention is further specifically illustrated by the following examples.

EXAMPLE 1

Cloning and Sequencing of the LKP 5 hipP Gene and the LKP1 Operon

Materials and Methods

Bacterial strains and plasmids

*H. influenzae* strains P860295 (ATCC 53775), P86149 (ATCC 53778), and P810384 (ATCC 53779) which express LKP serotypes 1, 4, and 5 respectively, described previously (Brinton, C. C. et al., *Pediatr. Infect. Dis. J.* 8 *Suppl.*: 54–61 (1989)) were employed. *E. coli* strains MB392 (Kar, S. et al., *Infect. Immun.* 58:903–908 (1990)) and HB101 were used as hosts for recombinant plasmids and strain DH5-α was used for cloning steps involving β-galactosidase α-peptide complementation. Hflu were grown in brain heart infusion (Dco Laboratories, Detroit, Mich.) containing 10 µg/ml hemin (Sigma Chemical Co., St. Louis, Mo.) and 2 µg/ml NAD (Sigma) at 37° C. *E. coli* strains were grown in Luria broth (Miller, J. H., *In Experiments in molecular genetics.,* 203 (1972). Cold Spring Harbor Laboratory. Cold Spring Harbor, N.Y.) at 37° C. Where appropriate, antibiotics were used at the following concentrations: ampicillin (Sigma) 100 µg/ml, kanamycin (Sigma) 25 µg/ml, and chloramphenicol (Sigma) 20 µg/ml.

Construction and properties of plasmid pHF1 which expresses LKP1 pili in *E. coli* as described previously (Kar, S. et al., *Infect. Immun.* 58:903–908 (1990)) were employed. Plasmid pPX551 is a pUC18 derivative containing the 1.9 kb XhoI fragment of pHF1 inserted into the BamHI site. Deletion clones of pHF1 lacking the pepN locus were constructed as described in the text. The LKP4 pilin structural gene was isolated by PCR amplification of P860295 chromosomal DNA using primers with the following sequences: for the 5' end of the gene-5'GTGCT GGATCCGTTTCTCTTGCATTACATTAGG 3' (SEQ ID NO:12) and for the 3' end- 5'TTAG GAATTCGGAAGCGTTTTTTACTTTTTTTGG3' (SEQ ID NO:13). The 5' primer included a HindIII restriction site, underlined in the sequence, and the 3' primer included an EcoRI site also shown underlined. The PCR product was cloned into pCR1000 (Invitrogen, Inc., California) as per manufacturer's directions. The LKP4 structural gene was subcloned by blunting the EcoRI site with Klenow in the presence of all four dNTPs, and cutting with Asp718 I (an Asp718 I site is located in the vector) releasing the fragment. The LKP4 gene was ligated into HindII-Asp718 I cut pPX191 (a derivative of pUC19 with the bla gene replaced by the cat gene from pACYC184 (Chang, A. C. Y., and S. N. Cohen, *J. Bacteriol.* 134:1141–1156 (1978)) to form pPX602.

The LKP5 pilin structural gene was isolated from P810384 by PCR using the following primers: for the 5'end- 5'-AACGAATTCTGCTGTTTATTAAGGCTTTAG (SEQ ID NO:14) and for the 3'-AGCTGGATCCTTGTAGGGTGGGCGTAAGCC (SEQ ID NO:15). The PCR product of approximately 1 kb was cloned into pCRII (Invitrogen, Inc., San Diego, Calif. and subcloned as a blunt ended fragment by Klenow treatment of EcoRI ends generated using the vector's flanking EcoRI sites. The LKP5 pilin gene was subcloned into plasmid pPX191 and orientation determined by restriction analysis. The LKP5 subclone was saved as pPX605.

Cloning of hipP genes encoding other LKP serotypes hipP loci encoding serotype 4 and serotype 1 LKP genes have been described (Kar, S. et al., *Infect. Immun.* 58:903–908 (1990); van Ham, S. M. et al., *EMBO Jour.* 8:3535–3540 (1989)). To determine the serotype specificity of LKP pili is located within the hipP gene, PCR was used to clone the serotypes 4 and 5 pilin genes from an NTHi strains expressing these pili. The PCR product for the LKP4 pilin gene was cloned into pPX191 as described above and is expressed under control of the lac promoter. The hipP gene from an LKP5 expressing Hflu strain was isolated by PCR as described and cloned into pPX191 for expression under lac control.

Oligonucleotide synthesis

The synthetic oligonucleotides used as primers for PCR amplification and DNA sequencing were synthesized on an Applied Biosystems (ABI) 380B DNA synthesizer using b-cyanoethyl phosphoramidite chemistry (Sinha, N. D. et al., *Nucleic Acids Research* 12:4539–4557 (1984)).

Polymerase chain reaction (PCR) amplication

The LKP4 hipP and LKP5 hipP pilin genes were amplified by PCR from NTHi strains P861249 and P810384 respectively, using standard PCR amplification protocols (Saiki, R. K. et al., *Science* 239:487–491 (1988)).

DNA sequencing

The hipP gene contained on plasmid pPX551 and the entire LKP1 operon contained on plasmid pHF1 were sequenced with standard M13 sequencing primers and with overlapping sense and antisense primers. All the DNA sequencing was done on an Applied Biosystems (ABI) 373A DNA Sequencer, utilizing the Taq thermal cycling DyeDeoxy™ Terminator sequencing kit from ABI, part #901497. The LKP4 and LKP5 serotypes were sequenced directly from the PCR products using the PCR amplification primers and internal synthetic primers based on the LKP1 sequencing study.

SDS-PAGE analysis

Sodium dodecyl sulfate polyacrylamide gel electrophoresis (SDS-PAGE) was performed in a 70 by 100 mm mini-gel system (Bio-Rad, Richmond, Calif.) using the method of Laemmli (Laemmli, U.K., *Nature (London)* 227:680–685 (1970)). Samples were reduced with β-mercaptoethanol or DTT in sample preparation buffer and boiled for 5 min. Gels were run at 150 V constant voltage. Separated proteins were detected by staining with Coomassie brilliant blue G-250 (Sigma).

Partial purification of pili

LKP pili were purified according to previously described methods using differential pH solubility (Brinton, C. C., Jr. et al., *Pediatr. Infect. Dis. J.* 8 *Suppl.*:54–61 (1989)). Briefly, piliated bacteria were harvested from liquid culture by centrugation and washed 2× in phosphate buffered saline, pH 7.2. The bacterial pellet was resuspended in 100 mM tris, pH 10.3, containing 150 mM NaCl at a ratio of 4 ml buffer/g wet weight of cells. Pili were sheared off of the cells by blending in an Oster miniblender for three 3 min bursts at 4° C. Bacterial debris was separated by centrugation and discarded. The supernatant was dialyzed against 50 mM NaAcetate, pH 5.0 overnight to precipitate pili and denature other proteins. The pellet was collected by centrugation at 15,000×g at 4° C. and dissolved overnight in 50 ml of 0.01 M CAPS buffer, pH 10.4 with gentle rocking. This cycle of acid precipitation and solubilization in basic buffer was repeated two more times. The final acid pellet was then resolubilized in 0.01 M NaPhosphate, pH 10.4 and non soluble material discarded. This soluble fraction was referred to as partially purified pili.

Sequence of the LKP1 operon

The LKP1 operon was sequenced as described above and the full sequence is set forth in SEQ ID NO:4. Sequence analysis indentified six potential open reading frames (ORFs) in the LKP operon, including the hipP (at about nucleotide 1882–2532 of SEQ ID NO:4) and hipC (at about nucleotide 2854–3630 of SEQ ID NO:4) genes. All six ORFs in the LKP operon were identified as homologous to equivalent pilus operon genes in the pilus superfamily, as defined by multiple sequence alignment of proteins. Analysis of sequence alignment was also performed using Entrez Sequences Database Release 10.0 of the National Center for Biotechnology Information (National Library of Medicine, Bethesda, Md.). Derived amino acid sequences of the ORFs are shown in FIGS. 2A–G (SEQ ID NOs:5–10). A function for each reading frame was assigned based on sequence alignment analysis. There are five ORFs which appear to be grouped into an operon controlled by the hipC promoter region. After the hipC (periplasmic chaperon) gene, the second reading frame hipR (at about nucleotide 4016–6238 of SEQ ID NO:4) was designated, a membrane anchor protein, the third ORF hipM (at about nucleotide 6259–6873 of SEQ ID NO:4) was designated, a tip associated protein, (also referred to herein as a minor tip protein) and the fourth ORF hipA (at about nucleotide 6955–8265 of SEQ ID NO:4) was designated, a tip adhesin protein. The pilin gene (hipP) and the periplasmic chaperon gene (hipC) are transcribed in opposite orientations as in the LKP 4 operon with the promoter region having the previously indentified TA repeats(van Ham, S. M. et al., *Cell* 73:1187–1196 (1993)). Since pHF1 expresses LKP1 pili in *E. coli*, there are 10 TA repeats in the intrapromoter region as described by van Ham et al. These TA repeats are responsible for phase variation of the LKP pili phenotype, with loss of some of the repeats resulting in loss of piliation and a TA repeat number between 10 or 11 allowing expression of the LKP operon. As indentified on the LKP1 operon was an ORF encoding an integrase (at about nucleotide 1495–1868 of SEQ ID NO:4). Also located on the LKP1 operon was a sequence encoding an enzyme, peptidase (at about nucleotide 8395–9342 of SEQ ID NO:4).

The predicted size of the LKP1 hipP gene product is approximately 21.2 kilodaltons, assuming a signal sequence length of 20 amino acids, while the observed molecular weight in SDS-PAGE gels is approximately 27 kilodaltons. Part of this may be explained by the anomalous sequence migration of LKP pilins in general in SDS-PAGE gels (mature LKP4 migrates at a molecular size of 24 kilodaltons while its predicted size is 22.1 kilodaltons) but the exact explanation remains unknown.

Sequence comparison of LKP serotypes 1, 4, and 5 hipP genes

This report represents the first sequence analysis of the hipP genes encoding LKP serotypes 1 and 5 (FIG. 1). The hipP gene from an LKP4 expressing Hib strain has also been sequenced (van Ham, S. M. et al., *EMBO Jour.* 8:3535–3540 (1989)) and the derived amino acid sequence shows 99% identity with the LKP4 hipP derived amino acid sequence contained herein. The hipP gene sequences from Hib strains Eagan and M43 have been published (Forney, L. J. et al., *Infect. Immun.* 59:1991–1996 (1991)). The LKP1 hipP gene should encode a protein of approximately 21.5 kD while the predicted molecular weight of the LKP 4 hipP protein is 23.8 kD. The actual hipP gene products observed in recombinant *E. coli* are of approximately the correct sizes in Western blots for LKP4 and LKP5, but the LKP1 pilin runs aberrantly at a higher molecular weight than predicted at 26 kD. MacVector software was used to assess homology of these genes, with LKP4 hipP and LKP5 hipP proteins being 70 and 67% identical to LKP1 hipP, respectively. The alignment between the sequences is very good at the amino termini of the proteins, with three major areas of sequence divergence in the LKP1, 4, and 5 serotype genes farther into the proteins as shown in the Figure. Since little cross reactivity is observed between anti-LKP1, anti-LKP4, or anti-LKP5 sera with intact pili of a heterologous serotype, the sequences responsible for the serotype specificity of the typing antisera must be located in these regions. By comparison of the sequences in GenBank to the LKP4 sequence, the *H. influenzae* type b M43 pilin (Gilsdorf, J. R. et al., *Infect. Immun.* 58:1065–1072 (1990)) sequenced by Gilsdorf et al. also appears to be an LKP4 serotype gene (data not shown).

EXAMPLE 2

Construction of LKP Type Pili-Producing *E. coli* Recombinants

Bacterial strains

Piliated Hflu strains used for *E. coli* recombinant construction are LKP11/CB59, LKP10/88-0807 and LKP12/88-0677. Hemagglutination and serum agglutination were examined before making genomic library. *E. coli* strains XL1-Blue$^{MR}$ and HB101 were used as cloning host cell.

DNA library construction and cosmid vector DNA

Chromosomal DNA from LKP11, LKP10 and LKP12 were extracted and purified respectively by standard techniques. Hflu genomic DNA size is about $1.8 \times 10^6$ bp. Chromosomal DNA was partially digested with restriction enzyme Sau3A I. Approximately 30 kb DNA fragment was eluted from LMTA-gel (Sigma) and purified by phenol-chloroform method. The final DNA concentration is about 1 ug/ul.

Vector DNA SuperCos I (Stratagene, La Jolla, Calif.) was digested with Xba I and dephosphorylated with calf intestinal alkaline phosphatase (CIAP). The Xba I and CIAP treated vector DNA was then digested with Bam HI restriction enzyme. About 6.5 kb vector DNA fragment was obtained.

LKP11/CB59, LKP10/88-0807 and LKP12/88-0677 DNA fragments were ligated at the Bam HI site of the vector DNA SuperCos I, respectively. The ligated DNA was packaged into 1 phage particles using Ciga-pack Gold kit (Stratagene, La Jolla, Calif.). The host cell for packaging was XL1-Blue$^{MR}$.

Library screening

Figure 4:
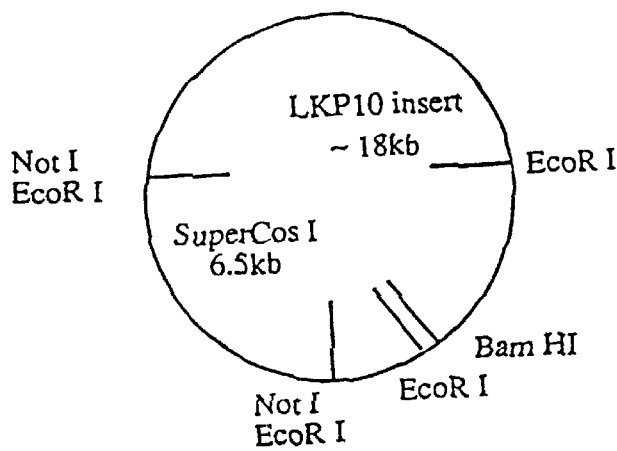
Figure 5:
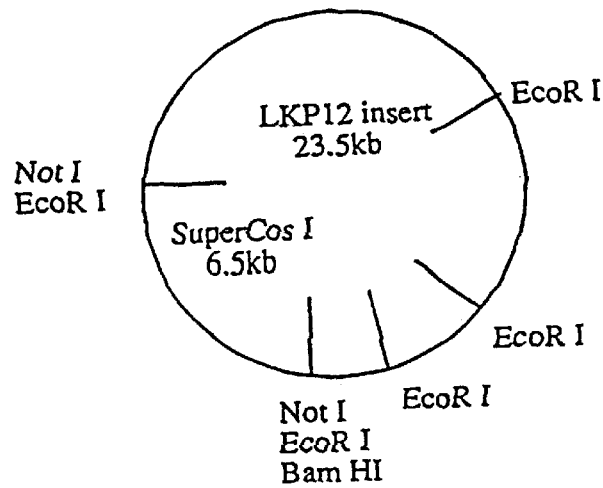

Recombinant expressed LKP type pili were screened by colony blot method. The concentration of anti-pilius sera from LKP11, LKP10 and LKP12 was 1:1000 dilution. The percentage of positive colony was 40/4200 for LKP11, 9/700 for LKP10 and 1/600 for LKP12. The cell piliation was examined by EM. The recombinants were verified by further HA and SA assay and they were named CLJ11 for LKP11, CLJ10 for LKP10 and CLJ12 for LKP12 (FIGS. 3, 4 and 5). Recombinants DNA was extracted and transformed to *E. coli* strain HB101 because XL1-Blue cell expresses type I pili. The recombinants DNA size is about 18.5 kb for CLJ11. This was obtained by digestion and subsequent ligation using restriction site on insert and vector DNA. CLJ10 DNA is about 25 kb and 35 kb is for CLJ12. Partial DNA sequence is available for these recombinant inserts.

EXAMPLE 3

Protocols for the Purification of an LKP Pilus from an *E. coli* Recombinant Strain Using the Liquid Phase Method General Protocol 1. Inoculate recombinant *E. coli* cells in a 3 ml of LB media containing ampicillin and grow at 37° C. until the OD 540 nm reading reaches 0.6–0.8 (3–4 hours).
2. Transfer the cell suspension to 50 ml of medium and grow at 37° C. until the reading at 540 nm reaches 0.8–1.0 (4–5 hours).
3. Transfer the 50 ml of cell suspension to 1 L of medium in 2.8 L flask and grow at 37° C. overnight (16–18 hours) until a reading at 540 nm of 4.0–5.0 is obtained.
4. Harvest cells by centrugation at 5000 rpm for 15 minutes.
5. Resuspend the cells in 50 nM acetate buffer pH 5.0 and keep the suspension at room temperature for 1 hour.
6. Blend at 11000 rpm in large cup, or 14000 rpm in small cup, with omnimixer, ice for 3 minutes.
7. Titrate to pH 8.0 with 1 M Tris-HCI and let stand for 3 hours at room temperature.
8. Centrifuge at 12000 rpm for 20 minutes at 4° C. Weigh all pellets and discard.
9. Add 10 ul of DNase and RNase for each 100 ml of prep. Mix thoroughly and let stand for 10 minutes at room temperature.
10. Dialyze against several changes of 50 mM acetate buffer pH 5.0 overnight. Of the prep does not reach pH 5.0 overnight, then dialyze longer against more changes of buffer.
11. Centrifuge at 16000 rpm for 60 minutes at 4° C. to pellet the protein precipitant and pilus crystals.
12. Resuspend the pellet in about 25% original volume with 25 mM Tris-HCI buffer pH 8.0.
13. With gentle stirring add Triton X-100 and EDTA to the prep to yield final concentration of 0.2% and 5 mM. Stir gently overnight at 4° C.
14. Clarify the prep by centrifuging at 16000 rpm for 60 minutes at 4° C.
15. Add NaCl and PEG 8000 to final concentration of 0.5 M and 3.0% respectively then incubate and prep over ice for 2 hours.
16. Centrifuge the prep at 16000 rpm for 60 minutes at 4° C. to pellet the pilus crystals.
17. Resuspend pellet in 25 mM Tris-HCI pH 8.0 in ⅓ of previous volume. Use less solution a lesser yield of pilus crystals is obtained.
18. Repeat steps 13 to 17.
19. Resuspend pellet in 25 mM Tris-HCI pH 8.0. Depending on purity and amount of material alternative solubilization and crystallization steps may be continued as needed.

During purification, sample after each step and use SDS-PAGE to examine purity of the samples. Dark field microscopy assay is needed in assistance for purity checking. It is necessary to use UV scanning to determine any contamination by DNA or RNA.

Since Triton X-100 has a strong absorbance at 280 nm, it is important to remove the residual of Triton X-100 by crystallization, one time, or more, of pili by PEG and NaCl after purification. This avoids false reading at 280 nm when one determines concentration of pilus preparation by UV method.

Purification of LKP 5 Pili

1. Harvest in 80 mM PBS pH 5.0 using 5–10 ml/tray.
2. Titrate prep to pH 5.0 with 6N HCI if necessary.
3. Blend with omnimixer over ice for 3 minutes (average speed=9800 rpm) (up to 11000 rpm if possible in larger cups and up to 14000 rpm in small cups).
4. Titrate to pH 9.0 with 5 M NaOH and let stand for 3 hours at room temperature. It may be necessary to stir gently to prevent pH changes. Monitor pH throughout and adjust if needed. (If cultures were grown in broth, then titrate with a 1 M solution of buffer (Tris) instead of NaOH.)

5. Centrifuge at 15300 g for 20 minutes at 4° C. Transfer supernatant to clean bottles and clarify a second time as before. Weigh all pellets and discard.
6. Adjust pH of supernatant to 8.0 and add 10 ul of DNase and RNase for each 100 ml of prep. Mix thoroughly and let stand for 10 minutes at room temperature.
7. Dialyze against several changes of 40 mM acetate buffer pH 5.0 overnight. If prep does not reach pH 5.0 overnight then dialyze longer against more changes of buffer.
8. Centrifuge at 18600 g for 60 minutes at 4° C. to pellet the pilus crystals (crystals not typical for clear pili).
9. Resuspend the pellet in about 25%, original volume with 25 mM Tris-CHI pH 9.0 using rubber policeman. Stir gently at 4° C. (avoid forming) several hours. Break up large pieces with gentle pipeting as needed.
10. With gentle stirring, add Triton X-100 (2% stock) to the prep to yield a final concentration of 0.4% and add EDTA (25 mM stock) to a final concentration of 5 mM. Incubate overnight at 4° C.
11. Clarify the prep by centrifuging at 186000 g for 60 minutes at 4° C. Transfer supernatant to clean flask.
12. Adjust the pH of the supernatant to below 8.0 using 1 N HCI.
13. Add NaCI (5 M stock) to a final concentration of 0.5 M and PEG (30% stock) to final concentration of 3% then incubate the prep over ice for 0.5 hour. Inspect in darkfield for crystals. Increase time if needed but it is critical not to overexpose pili to PAGE because resolubilization becomes increasingly difficult with increasing times.
14. Centrifuge prep at 18600 g for 60 minutes at 4° C. to pellet the pilus crystals.
15. Wash pellet with 40 mM citrate buffer pH 5.0 to remove excess PEG/NaCl. Then centrifuge at 186000 g for 60 minutes (2 times).
16. Resuspend pellet in 25 mM Tris-CHI pH 9.0 in ⅓ to ½ previous volume. Solubilize by swirling followed by gentle pipetting. Run sample on a gel to check for purity. If necessary, continue with step 17.
17. Add Triton x-100 to the prep to yield a final concentration of 0.4% and add EDTA to a final concentration of 5 mM then incubate overnight at 4° C. (see step 10 for details).
18. Adjust the pH of the prep to below 8.0 using HCI (between 7 and 8).
19. Add NaCI to a final concentration of 0.5 M and PEG to a final concentration of 3% then incubate the prep over ice for 0.5 hours (see step 13 for details).
20. Centrifuge prep at 186000 g for 60 minutes at 5° C. to pellet pilus crystals.
21. Resuspend the pellet in 252 mM Tris-HCI pH 9.0 to solubilize pili (see step 16 for details). Check for purity by SDS-PAGE. If necessary, continue with step 22.
22. Add Triton X-100 to the prep to yield a final concentration of 0.4% and add EDTA to a final concentration of 5 mM then incubate overnight at 4° C. (see step 10 for details).
23. Clarify by centrifuging at 18600 g for 60 minutes at 4° C.
24. Add NaCI to a final concentration of 0.5 M and PEG to a final concentration of 3# then incubate the prep over ice for 0.5 hour (see step 13 for details).
25. Centrifuge at 18600 g for 1 hour at 4° C. Discard supernatant.
26. Resuspend pellet in Tris-HCI pH 9.0. Depending on amount and purity of material, alternating solubilization/crystallization steps may be continued as needed.

During purification process, monitor pellet material and supernatant by darkfield and/or gel and/or scan. May need to reprocess Purity by SDS-PAGE check: Repeat Triton step as needed, but avoid SDS reaction steps in previous protocols because of high losses of pili.

EXAMPLE 4

Purification of LKP pili by HPLC and Other Column Methods

Besides detergent extraction and PEG precipitation, LKP pili also can be purified by HPLC, FPLC and other column methods. These methods are good particularly for unknown LKP pili. Normally, pili are partially purified by extraction and precipitation first until the pilus solution is clear, concentrated and very small size. The preparation still is not pure as determined by SDS-PAGE, column methods would be the application of the choice. Sizing columns are preferred to be used for this purpose. Prior to loading to a column, treatment for further purification of the pilus sample is important. The detergent used for partial purification of pili should be removed from pilus samples by dialysis or other known techniques. Detergent significantly reduces column separation resolution. Size exclusive column requires a small sample volume.

Figure 6A:
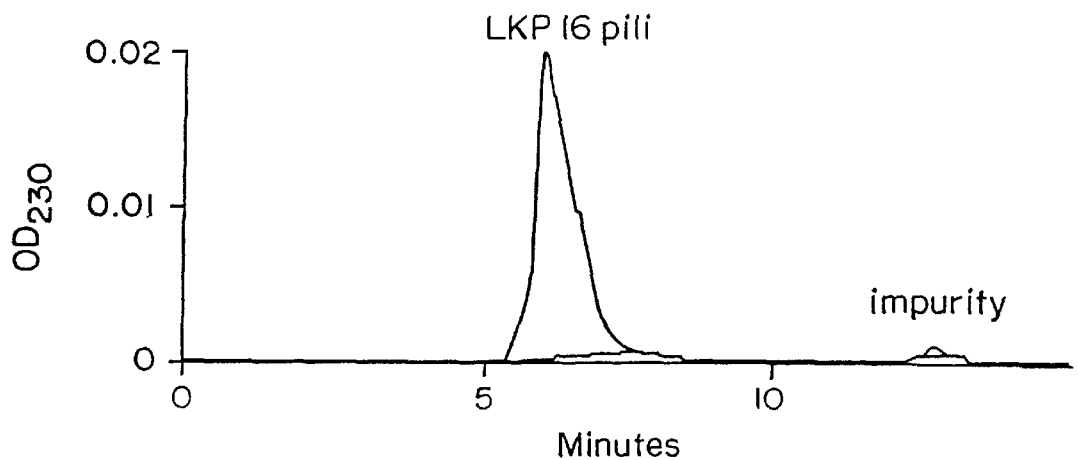
FIGS. 6A and B are graphic representations showing the HPLC purification of LKP16 and LKP19 pili. Protein was eluted out from a sizing column with 150 mM Tris-HCI, pH 8.0, monitored at 230 nm.
Figure 6B:
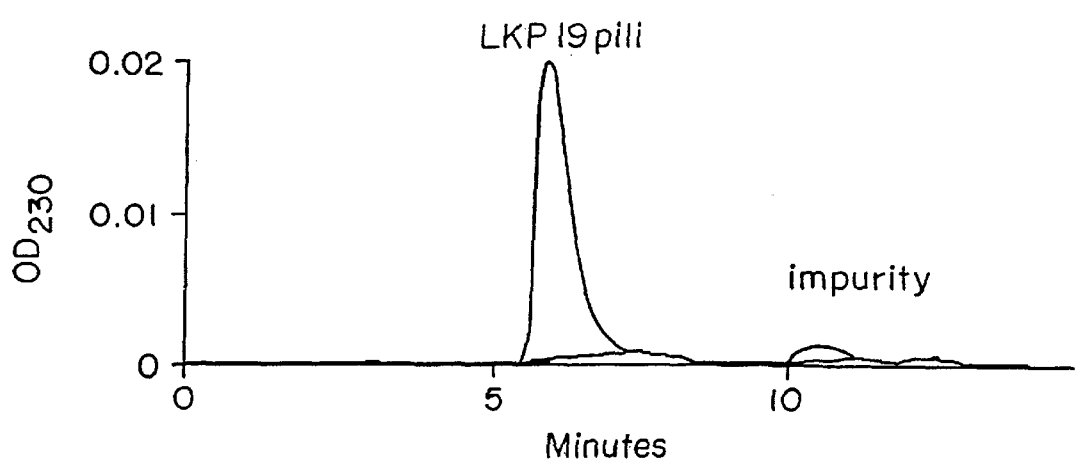
Figure 7:
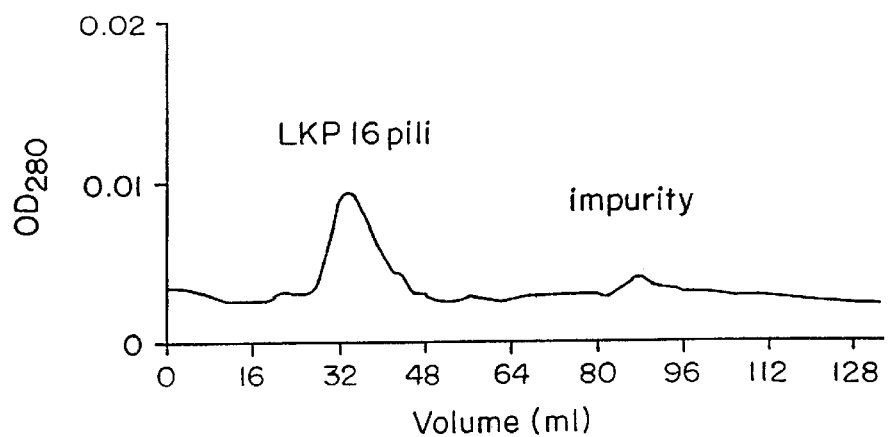
FIG. 7 is a graphic representation showing the purification of LKP16 pili with Sepharose CL-6B column (1×50 cm). Protein was eluted out with 25 mM Tris-HCI, pH 8.0, monitored at 230 nm.
Figure 8:
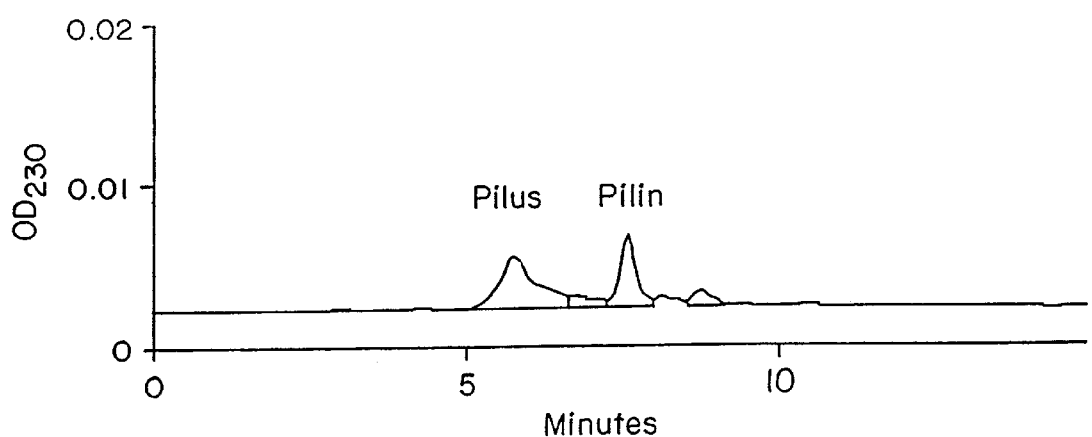
FIG. 8 is a graphic representation showing the HPLC separation of LKP1 pili and LKP1 pilin subunits. Protein was eluted out from a sizing column with 150 mM Tris-HCI, pH 8.0.

For HPLC or FPLC, the loading volume of 50 ul to 200 ul is recommended, and for other routine LC gel filtration columns, the sample loading volume depends on the length and size of the column. A 1 ml of pilus sample is preferred for a column with a total volume of 50 ml. Since pili have a low absorbance at 280 nm, a higher sensitivity for monitor is recommended. Available protein eluted from column can be monitored at 230 nm. FIGS. 6A and 6B show the purification of unknown pilus LKP16 from clinic isolate 880715 and LKP19 from 881219 by HPLC protein KW-804 column from Waters Company. Further purification of KKP16 by HPLC is shown in FIG. 5. FIG. 7 shows the purification of LKP15 and LKP16 by a Sepharose CL-6B column (1×50 cm). Column methods are also useful for isolation of pilin from pili. FIG. 8 shows the isolation of LKP1 pilin from LKP1 pilus rods.

EXAMPLE 5

Protocol for the Purification of an LKP Pilus from an Hflu Strain or *E. coli* Recombinant Strain Using Solid Phase Method Generally speaking, recombinant strain expresses pilus structural protein better than parent strain, H flu, does, therefore, it is easier to purify pili from the recombinant cells. However, due to the fact that the *E. coli* recombinant strain expresses the pilus protein as same as the parent Hflu does, purification procedures of pilus rods from Hflu or from recombinant strain are basically the same. Growth of Hflu strain requires choclate agar media and certain $CO_2$ and humidity. Growth of *E. coli* recombinant strain needs LB agar media containing ampicillin.

1. Harvest in 80 mM PBS pH 5.0 using 5 ml/tray. Use a smoothed glass edge to scrape wet cells and then transfer the cell suspension to omnimixer cup. Less cells are made surface only use media surface moisture to collect wet cells.
2. Titrate prep to pH 5.0 with 2 M acetate buffer necessary.
3. Blend at 14000 rpm with omnimixer over ice for 3–5 minutes.
4. Titrate to pH 8.0 with 1 M Tris-HCI buffer and monitor pH change by pH meter. It may titrate to pH with 2.5 or 5 M NaOH instead of Tris buffer, prep contains a lot of wet cells. Be careful to avoid lysis of cells when use NaOH. Incubate the prep at room temperature for 3 hours.
5. Centrifuge at 12000 rpm for 20–30 minutes at 4° C. Weigh all pellets and discard.
6. Add 10 ul of DNase and RNase for each 100 ml of prep. Mix thoroughly and let stand for 10 minutes at room temperature.
7. Dialyze against several changes of 50 mM acetate buffer, pH 5.0, overnight. prep does not reach pH 5.0 overnight then dialyze longer against more changes of buffer.
8. Centrifuge at 16000 rpm for 60 minutes at 4° C. to pellet protein precipitate and pilus crystals.
9. Resuspend pellet in about 25% original volume with 25 mM Tris-HCI buffer, pH 8.0.
10. With gentle stirring, add Triton X-100 and EDTA to prep to yield final concentration of 0.2% and 5 mM. Stir gently overnight at 4° C.
11. Clarify prep by centrugation at 16000 rpm for 60 minutes at 4° C.
12. Add NaCl and PEG 8000 to final concentration of 0.5 M and 3.0%, respectively, then incubate the prep over ice for 2 hours. LKP pili with different length and dimer may be crystallized in different concentrations of NaCl and PEG 8000. Therefore a concentration test for NaCl and PEG to crystalize different pili is important.
13. Centrifuge at 16000 rpm for 60 minutes at 4° C. to pellet pilus crystals.
14. Resuspend pellet in 25 mM Tris-HCI, pH 8.0 in ⅓ previous. Use even less solution a smaller yield of pilus crystal is found.
15. Repeat from step 10 to step 14.
16. Resuspend pellet in 25 mM Tris-HCI, pH 8.0. Depending on purity and amount of material, alternate solubilization and crystallization steps may be continued as needed.

During purification, sample after each step and use SDS-PAGE to examine purity of the samples. Dark field microscopy assay is needed in assistance for purity checking. It is necessary to use UV scanning for finding out any contamination by DNA or RNA.

Since Triton X-100 has a strong absrbance at 280 nm it is wise to remove the residual of the detergent by one more time crystallization of pili by PEG and NaCI after purification. This avoids false readings at 280 nm when one determines concentration of pilus preparation by UV method.

EXAMPLE 6

Construction of MBP-Δ3'Tip Fusion Protein

The genetic fusion was constructed by using PCR primers to obtain a portion of the LKP1 tip gene from pHF1 which would be in frame with the MBP protein gene in the vector pMAL-p2. The primers were designed so that the carboxyl terminal of approximately 100 amino acids of the tip protein would be deleted and replaced with a stop codon. The amino terminal portion of the protein was PRC'd in frame with an appropriate restriction site at the approximate point of the signal sequence cleavage site which was determined by analogy to other bacterial signal sequences and the hydrophobicity profile of the deduced amino acid sequence of the tip protein. The amino acid sequence of the fusion protein is shown in FIG. 9. The partial sequence of the LKP tip protein of the fusion protein is underlined.

Expression of the fusion, purification, and antisera production

The protein was expressed in E. coli BL21 (an onnipT.lon K-12 strain) grown in SOB broth containing ampicillin at 100 μg/ml at 28 C. after induction with 0.2 mM IPTG. The cells were pelleted by centrugation and washed 1 time in PBS. The cells were resuspended in 20 mM Tris, pH 7.5 containing 2 mM EDTA and 400 mM NaCl at a ratio of 20 ml/liter of original culture. The cells were lysed by passing through a French pressure cell 3 times and the cell debris removed by low speed centrugation at 8 times×g for 20 minutes at 4° C. The supernatant was diluted 5-fold in the same buffer used for breakage and passed over a 15 ml bed volume amylose resin column at 1 ml/min at room temperature. After the lysate was run over the column, the column was washed with 15 bed volumes of the lysing buffer at 5 ml/min. The bound material was eluted using washing buffer containing 10 mM maltose. The elution was done with 50 ml of buffer at 1 ml/min and the eluant pooled. The resulting protein mixture was analyzed by SDS-PAGE and Western Blot and anti-MBP sera and found to contain the fusion, breakdown products, and full length MBP. Little other material was detected.

The fusion proteins, MBP and breakdown products eluted as a complex. Mice were immunized with 10 μg doses of the complex using 100 μg MPL as adjuvant. Immunizations were done subcutaneously at weeks 0, 4, and 6 and the mice exsanguinated on week 8. The negative control sera was mouse anti-MBP sera made against purified MBP using the same purification and immunization protocols.

Anti-GST sera

The GST fusion was constructed using the complete LKP tip gene, including the signal sequence. The gene was PCR'd out from PHF1 with the appropriate restriction enzyme sites for insertion into pGEX-3× in frame, and expressed in E. coli DH5α. The cells were grown in SOB containing 100 μg/ml ampicillin and induced with IPTG at 0.2 mM at 37° C. for 2 hours. The cells were harvested and washed in PBS, then resuspended in PBS and lysed by passing through a French pressure cell. Cell debris was harvested by centrugation, and washed 3 times with buffer containing 1% Triton X-Zwittergent 3–14 and the inclusion bodies recovered by centrugation. The inclusion bodies were solubilized in 5 M guanidine HCl and analyzed by SDS-PAGE. The guanidine concentration was lowered to 2.5 M by dialysis and the soluble inclusion bodies stored at 4° C. The antisera was made by running preparative 10% SDS-PAGE gels and cutting the fusion band out of the gel. The acrylamide-protein band was minced using a scalpel and mixed with MPL (100 μg) and injected into mice 3 times at weeks 0, 4, and 6. Mice were bled at week 8.

EXAMPLE 7

Removal, Purification and Identification of H. influenzae LKP Pilus Tip Adhesin Protein This is the first demonstration that tip adhesin protein from H. influenzae LKP1 pili can be removed without depolymerization of pilus rods. Free tip adhesin protein can be isolated and purified by means of dialysis and prep-electrophoresis. Purified tip adhesin can be identified by the antiserum from a constructed genetic fusion protein, which is from a portion of LKP1 tip gene and MBP (maltose binding protein) gene, using Western blot analysis. Specific binding was detected between the purified tip protein and fusion protein antiserum, which clearly shows that the protein purified from LKP1 pilus prep is LKP1 tip adhesin protein.

Activity assays with human red blood cell (RBC) ghosts demonstrated that purified tip protein binds to a native ghosts preparation but not does not bind to denatured RBC ghosts, indicating that purified tip protein is biologically functional or at least partially functional.

Removal of Tip Protein from Pilus Rods

1. Dialyze purified LKP1 pili in 200 mM Gly-HCl buffer, pH 2.0 containing 5 M NaCl, at room temperature for 4 to 6 hours.
2. Transfer the dialysis bag into a 25 mM Tris-HCl buffer, pH 8.0 and dialyze for several hours till the pH of pilus prep reaches to pH 8.0.
3. Add SDS to the pilus prep to a final concentration of 0.1% and incubate in 4° C. for 10 hours.
4. Dialyze the pilus prep in 50 mM citrate buffer, pH 5.0 overnight.
5. Pilus aggregates can be removed by centrugation and most free tip protein is retained in the supernatant.

Tip protein can be completely removed by 2% SDS in 25 mM Tris buffer without depolymerization of pilus rods, but the SDS may damage the activity of the protein. 0.1% SDS only removes about 20–30% of total tip protein, however, the protein maintains biological activity. The results also demonstrated that 4M urea and 2M GuHCl in pH 2.0 buffer can partially remove tip protein from pilus rods without depolymerization.

Purification of tip protein

Figure 10:
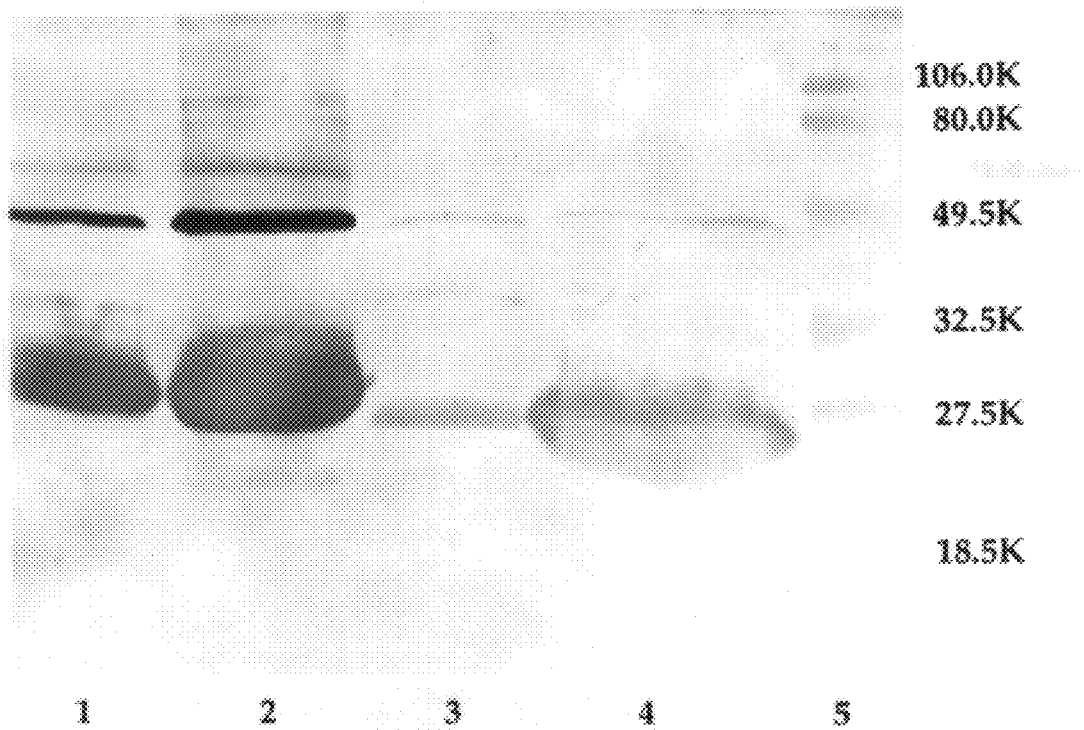
FIG. 10 is a photograph of a gel showing the identification of LKP1 tip adhesin protein by antibodies reactive with the fusion protein of LKP1 tip adhesin-MBP in Western blotted membranes. Lanes 1 and 2: different preps of purified LKP1 pili with tip protein (47 Kd). (A positive reaction was shown between tip protein and the antibody); lane 3: purified LKP10 pili with tip adhesin (47 Kd). (The tip protein does not react with the antibody); lane 4: purified LKP11 pili with tip protein (47 Kd). (The tip protein does not react with the antibody); lane 5: protein molecular weight markers.
Figure 11:
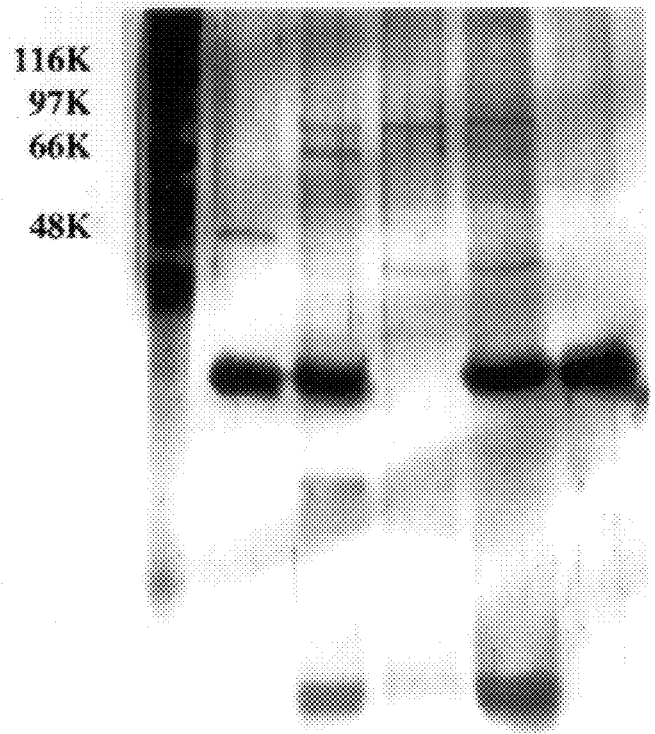
FIG. 11 is a photograph of a gel showing the binding activity of LKP1 tip adhesin to human red cell (HRC) ghosts. Lane 1: molecular weight markers; lane 2: purified LKP1 pili with tip protein; lane 3: the pili with HRC ghosts after centrifugation. Tip protein band (47 Kd) disappeared due to the binding of tip adhesin pili to ghosts pellet; lane 4: HRC ghosts after centrifugation, used as control; lane 5: purified pili without tip protein (treated with 1% SDS) was incubated with fresh ghosts, showing the same protein band pattern as the pattern of lane 3; Lane 6: purified pili without tip protein. Prior to the gel loading, pili were treated with 1% SDS, exhaustively dialyzed in 25 m Tris buffer, pH 8.0, crystallized by PEG plus NaCl and resolubilized in 25 mM Tris buffer, pH 8.0.
Figure 12:
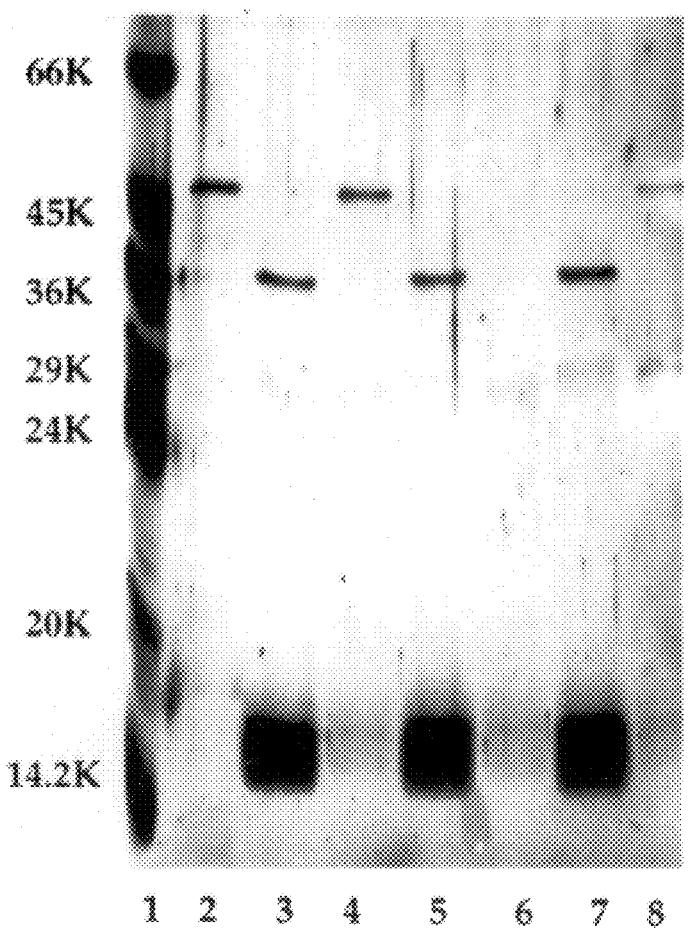
FIG. 12 is a photograph of a gel showing the binding activity of purified LKP1 tip adhesin protein to human red cell ghosts. Lane 1: molecular weight markers; lane 2: purified tip adhesin protein with a molecular weight of 47 Kd and the protein was removed by 0.1% SDS in 100 mM Glycine buffer, pH 2.0; lane 3: purified adhesin was incubated with fresh human red cell ghosts and pelleted by centrifugation prior to loading the supernatant on the gel. The tip adhesin band disappeared due to the binding to HRC ghosts; lane 4: purified adhesin was incubated with boiled HRC ghosts and pelleted by centrifugation prior to loading the supernatant on the gel. It showed adhesin band with 47 Kd, which indicates that tip adhesin protein does not bind to the ghosts pellet; lane 5: supernatant of fresh ghosts after centrifugation. It was used as a control; lane 6: supernatant of boiled HRC ghosts after centrifugation, showing a different soluble protein pattern from that of fresh HRC ghosts, used as another control; lane 7: different prep of purified tip protein incubated with fresh HRC ghosts, which showed the binding between tip protein and fresh HRC ghosts pellet; lane 8: different prep of purified tip protein incubated with boiled HRC ghosts, indicating that the tip protein does not bind the denatured ghosts. The gel was silver stained.
Figure 13:
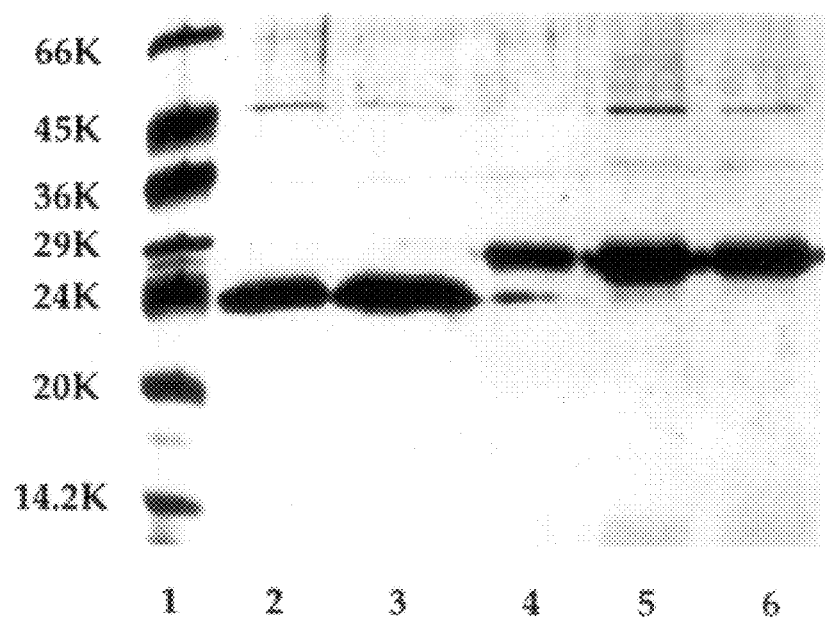
FIG. 13 is a photograph of a gel showing adhesin proteins from different LKP type pili with the same molecular weight. Lane 1: molecular weight markers; lane 2: LKP10 pili; lane 3: LKP11 pili and lane 4 to 6: different purified preparation of LKP1 pili (SEQ ID NO: 4) and the deduced amino acid sequence for six open reading frames (SEQ ID NOs: 5–10). Proteins were stained with silver.

1. Mix concentrated tip protein with SDS-PAGE sample treatment buffer without the SDS and β-mercaptolethanol. The ratio is 2.5 ml of pilus prep to 0.3 ml of sample treatment buffer.
2. Load the sample to a 12% SDS-PAGE (0.1% SDS) in Prep-Cell (Bio-Rad) with the length of stacking gel of 0.8–1.0 cm and running gel of 5 cm.
3. Run the gel at 300 volt with cooling system for 6–8 hours, and monitor the elution at 280 nm.
4. Pool the fractions containing tip protein and concentrate.
5. Determine the purity of the pooled fractions by mini-SDS-PAGE. The identification of purified tip protein by anti-KLP1-MBP fusion protein is shown in FIG. 10. The binding activity of purified tip protein with human red cell ghosts is shown in FIGS. 11 and 12. FIG. 13 compares adhesin proteins from different LKP type pili by SDS/PAGE.

EXAMPLE 8

Serotype Analysis

The *Haemophilus influenzae* (Hflu) bacterioplex is a differentiated complex of bacterial phases, or cell types, socially organized to facilitate the protein appendages expressed on the surface of Hflu, and also secreted from Hflu in free form, carrying specific adhesion determinants for binding to human cell membrane receptors. Pili adapt pathogenic bacteria to life in vertebrate hosts by mimicking the functions of the host's own proteins. Pilus functions include attaching bacteria to a variety of host cells and tissues and stimulating the host's immune system in ways which benefit the bacteria and damage the host. Pili are transmission, virulence, dissemination, pathogenicity and immunity factors in most bacterial diseases.

The expression of pili is controlled by a genetic switching mechanism, phase variation, in which pilus expression and pilus type are switched on and off at probabilities which vary with and are determined by conditions and signals in the immediate environment of the bacteria. Under some conditions the switching probabilities can be very high, as high as $10^{-2}$ per bacterial cell division. Under other environmental conditions the probability of the same phase switch can be $10^{-6}$ or lower. Phase switching is accompanied by both reversible and irreversible rearrangements in the DNA of pilus operons. Phase switching during in vitro growth is frequently accompanied by deletions to pilus operon genes such that nonpiliated phases remain irreversibly in that phase.

By purifying Hflu pili from different isolates and producing antisera to the purified preparations distinct LKP pilus serotypes have so far been identified. The expression of the different serotypes is used as a marker to identify the different piliation phases of the Hflu bacterioplex.

TABLE 1

|       |        | L = 1 | L = 2 | L = 3 | D = 3 | D = 4 |
|-------|--------|-------|-------|-------|-------|-------|
| LKP1  | N = 4  | 0     | 0     | 4     | 0     | 4     |
| LKP2  | N = 2  | 0     | 1     | 1     | 0     | 2     |
| LKP3  | N = 0  | 0     | 0     | 0     | 0     | 0     |
| LKP4  | N = 1  | 0     | 1     | 0     | 0     | 1     |
| LKP5  | N = 5  | 0     | 1     | 4     | 0     | 5     |
| LKP6  | N = 12 | 0     | 2     | 8     | 1     | 9     |
| LKP7  | N = 3  | 0     | 0     | 2     | 0     | 2     |
| LKP8  | N = 0  | 0     | 0     | 0     | 0     | 0     |
| LKP9  | N = 0  | 0     | 0     | 0     | 0     | 0     |
| LKP10 | N = 26 | 1     | 8     | 17    | 2     | 24    |
| LKP11 | N = 22 | 0     | 6     | 16    | 0     | 22    |
| LKP12 | N = 12 | 0     | 3     | 7     | 2     | 8     |
| LKP13 | N = 0  | 0     | 0     | 0     | 0     | 0     |
| LKP14 | N = 9  | 1     | 2     | 6     | 1     | 8     |
| LKP15 | N = 6  | 0     | 5     | 1     | 0     | 6     |
| LKP16 | N = 9  | 0     | 4     | 5     | 3     | 6     |
| LKP17 | N = 17 | 0     | 6     | 11    | 2     | 15    |
| LKP18 | N = 12 | 1     | 4     | 7     | 1     | 11    |
| LKP19 | N = 3  | 0     | 1     | 3     | 0     | 3     |
| LKP20 | N = 15 | 1     | 6     | 8     | 3     | 12    |
| Total |        | 4     | 50    | 99    | 15    | 136   |

Strains = 77

L = 1 is length < 0.2µ
L = 2 is length < 0.2µ < 0.5µ
L = 3 is length < 0.5µ
D = 3 is 3 nm diameter ("thin")
D = 4 is 4 nm diameter ("thick")

The frequency of each LKP serotype was determined for all serotypable cultures and for all cultures expressing typical LKP pili. The serotype frequency was determined by counting types on both single expressors and multiple expressors. Sixteen of the 20 serotypes were found on typically LKP piliated cultures and 90% of these cultures were serotypable in the 20-type system. The frequency distribution of serotypes for these cultures is shown in Table 1.

Three different LKP pilus operon genes were selected, the pilin gene, anchor gene and adhesin gene, which had all exhibited sequence similarity among different serotypes in multiple sequence alignments, but were also characteristic of Hflu LKP pili. Sequences were selected from these genes that would serve as suitable primer sequences flanking each gene for use in a PCR reaction.

```
LKP1 Pilin:   HF2 5'>AGCTGGATCCTTGTAGGGTGGGCGTAAGCC<3'   (SEQ ID NO:16)

HF1 5'> AACGGATTCGTTTGCTGTTTATTAAGCCTT<3'   (SEQ ID NO:17)

LKP1 Anchor:  R5 5'>GCCGCACCTTTGATGAACG>3'               (SEQ ID NO:18)

R3 5'>GGCAAATACGCACCGCTAAAT>3'             (SEQ ID NO:19)

LKP1 Adhesin: A5 5'>CGGACGAAGATGGTACAACGA>3'             (SEQ ID NO:20)

A31 5'>CCAAGCTTGGCCCGACATTATTATTGATATGACA>3'  (SEQ ID NO:21)
```

All three pairs of primers were synthesized and used in a PCR reaction to amplify segments of DNA extracted from Hflu isolates.

Data showing the presence of LKP pilus operons in tested *Haemophilus influenzae* strains is shown in Table 2.

TABLE 2

CORRELATION BETWEEN THE PRESENCE OF LKP PILUS OPERON MATERIAL IN *H. INFLUENZAE* ISOLATES AND THE EXPRESSED LKP PAPAMETERS OF PILIATION AND HEMAGGLUTINATICO

| LKP Parameter | Total | PCR Done | PCR + | PCR − | Fraction PCR + | Percent PCR + |
|---|---|---|---|---|---|---|
| Pilus Length 0 | 74 | 68 | 59 | 9 | 59/68 | 87% |
| Pilus length 3 | 101 | 93 | 82 | 11 | 82/93 | 88% |
| HA+ | 148 | 139 | 115 | 24 | 115/139 | 83% |
| HA− | 166 | 149 | 119 | 30 | 119/149 | 80% |
| Pilus Diam. 3 | 40 | 38 | 28 | 10 | 28/38 | 74% |
| Pilus diam. 4 | 172 | 159 | 136 | 23 | 136/159 | 86% |
| Serotypable | 189 | 173 | 149 | 24 | 149/173 | 86% |
| Not serotypable | 54 | 63 | 53 | 10 | 53/63 | 84% |

1. Pilus length 0 means nonpiliated.
2. length 3 means >0.5 microns (longest, typical of LKP pili).
3. HA+ means positive for hemaggiutination of human red cells; typical of LKP pili. (These isolates are not recalcitrant by definition.)
4. HA− means negative for hemagglutination of human red blood cells; typical of SNN pili. (These isolates are recalcitrant since all isolates were hemadsorbed at least once.)
5. Pilus diameter 3 means the isolates express pili with diameters typical of SNN pili.
6. Pilus diameter 4 means the isolates express pili with diameters typical of LKP pili.
7. Serotypable means the isolates agglutinate under standard conditions with at least one of the LKP pilus typing antisera in the 1–20 system.
8. Not serotypable means the isolates do not agglutinate with any of the LKP pilus typing antisera in the 1–20 system.

EXAMPLE 9

Hybridization Assay for *Haemophilus Influenzae* Assay Probe Construction

An approximately 1100 bp fragment from plasmid pHF1 (Karasic, R. et al., *Pediatr. Infect. Dis. J.* 8 (*Suppl.*):S62–65 (1988)) which contains the LKP1 serotype operon was amplified by PCR using primers which hybridize at the 5' and 3' ends of the hipA gene. This gene encodes the tip adhesin protein of the LKP1 pili. The PCR reaction included digoxigenin labeled dUTP along with the four dNTPs to label the PCR reaction product with digoxigenin. This probe was electrophoresed on an agarose gel and purified by cutting out the ~1.2 kb band and extracting the DNA by standard methods. The probe was redissolved in 30 µl of appropriate buffer.

Hybridization Assay

Eleven randomly chosen *Haemophilus influenzae* clinical isolates were grown on BHI-XV plates at 37° C. with 5% $CO_2$ and also streaked onto BHI agar. All isolates grew only on the BHI-XV plate, indicating that they were *H. influenzae*. The isolates included 2 Hib strains and 9 NTHi. The strains were inoculated onto a nylon membrane placed onto BHI-XV agar. Five clinical isolates of another respiratory pathogen, *Moraxella catarrhalis* were also spotted onto the filter. The bacteria were grown overnight at 37° C. in 5% $CO_2$. After growth, 2 *Bordetella pertussis* strains were spotted onto the filter. Filters were processed for colony hybridization according to the method of Maniatis et al. (*Molecular Cloning: A Laboratory Manual*, 1991, Cold Spring Harbor Laboratories, Cold Spring Harbor, N.Y.). Filters were blocked in pre-hybridization solution as described by Boehringer-Mannheim for the Genius™ system at 65° C. for 3 hours. Colony debris was removed by gentle rubbing with wet paper towels. The probe, 30 µl, was added to 5 ml of pre-hybridization solution and boiled for 10 minutes to denature the DNA. Probe was immediately added to the filter and allowed to hybridize overnight at 65° C. Filters were washed in 2× SSC, 0.1 SDS, 2× for 5 min/wash at room temperature followed by 2, 15 minute washes with 0.2× SSC, 0.1% SDS at 65° C. Bound probe was detected using alkaline phosphatase labeled anti-digoxigenin antibodies as described by the manufacturer. Results are shown in Table 3.

TABLE 3

HYBRIDIZATION OF dig-LABELED LKP 1 TIP PROBE TO RANDOM CLINICAL ISOLATES

| | Number of Positive Results | | | |
|---|---|---|---|---|
| Bacteria Strain | Strong Signal | Weak Signal | No Signal | # Total |
| *H. influenzae* | 4 | 4 | 3 | 11 |
| *M. catarrhalis* | 0 | 0 | 5 | 5 |
| *B. pertussis* | 0 | 0 | 0 | 2 |

The probe was specific for *H. influenzae* with no hybridization seen with either *M. catarrhalis* or *B. pertussis*.

Hybridization Assay of Nontypable Strains of *Haemophilus influenza* pili

Ten LKP pili expressing NTHi strains which express differing serotypes of LKP pili, along with Hib Eagan were grown on a nylon filter overlayed onto chocolate agar at 37° C. in 5% $CO_2$. An additional NTHi isolate was also included. After growth, two strains appeared yellow on the filter which was suggestive of non-Haemophilus bacteria, so they were tested by growth on BHI and BHI-XV. This experiment showed them to be contaminants and not NTHi. The filter was removed from the agar and processed as described above. The probe from the first experiment was reboiled and added to the filter as before, except that the hybridization temperature was lowered to 62° C. The filter was washed as before except that the wash temperature was also 62° C. Bound probe was detected as above. Results are shown in Table 4.

TABLE 4

HYBRIDIZATION OF dig-LABELED TKP TIP PROBE TO LKP TYPE STRAINS

| LKP Serotype | Signal with probe | No signal with probe | ID of strain |
|---|---|---|---|
| 5 | Strong | | NTHi |
| 2 | Moderate | | NTHi |
| 9 | Strong | | NTHi |
| 1 | Strong | | NTHi |
| 6 | Moderate | | NTHi |
| 13 | Strong | | NTHi |
| 4 | Strong | | NTHi |
| 7 | Moderate | | NTHi |
| | | X | Contaminant |
| | | X | Contaminant |

TABLE 4-continued

HYBRIDIZATION OF dig-LABELED TKP TIP PROBE TO LKP TYPE STRAINS

| LKP Serotype | Signal with probe | No signal with probe | ID of strain |
|---|---|---|---|
| 10 | Weak | | NTHi |
| 4 | Strong | | Hib |

The results set forth above establish that the DNA probes hybridized selectively to *Haemophilus influenzae*.

Equivalents

Those skilled in the art will recognize, or be able to ascertain using not more than routine experimentation, many equivalents to the specific embodiments of the invention described herein. Such equivalents are intended to be encompassed by the following claims.

We claim:

1. An isolated nucleic acid sequence encoding nontypable *Haemophilus influenzae* serotype 1 LKP pilin structural protein, consisting of the sequence selected from the group consisting of:

a) nucleotides 1882 to 2532 of SEQ ID NO:4;

b) the fully complementary strand of a);

c) nucleic acid sequences that selectively hybridize to the nucleotides of a); and d) RNA sequences transcribed from the nucleotides of a), b) or c).

2. An isolated nucleic acid sequence encoding nontypable *Haemophilus influenzae* serotype 1 KLP tip adhesin protein, consisting of the sequence selected from the group consisting of:

a) nucleotides 6955 to 8265 of SEQ ID NO:4;

b) the fully complementary strand of a);

c) nucleic acid sequences that selectively hybridize to the nucleotides of a); and d) RNA sequences transcribed from the nucleotides of a), b), or c).

3. An isolated nucleic acid sequence encoding nontypable *Haemophilus influenzae* serotype 1 LKP tip adhesin protein, consisting of nucleotides 6955 to 8265 of SEQ ID NO:4.

4. A recombinant expression vector comprising a nontypable *Haemophilus influenzae* serotype 10, serotype 11 or serotype 12 LKP operon DNA insert which encodes LKP pilus proteins, said expression vector which expresses at least one *Haemophilus influenzae* serotype 10, serotype 11, or serotype 12 LKP pilus protein in a procaryotic or eucaryotic cell.

5. A procaryotic or eucaryotic host cell transformed with a vector of claim 4.

6. The expression vector of claim 4 wherein the vector is CLJ 11 and the serotype 11 LKP operon DNA insert is approximately 12 kb.

7. The expression vector of claim 4 wherein the vector is CLJ 10 and the serotype 10 LKP operon DNA insert is approximately 18 kb.

8. The expression vector of claim 4 wherein the vector is CLJ 12 and the serotype 12 LKP operon DNA insert is approximately 23.5 kb.

9. A recombinant expression vector comprising a DNA insert encoding nontypable *Haemophilus influenzae* serotype 1 LKP tip adhesin protein, said DNA insert consisting of nucleotides 6955 to 8265 of SEQ ID NO:4, wherein said expression vector expresses a nontypable *Haemophilus influenzae* tip adhesin protein in a procaryotic or eucaryotic cell.

10. The recombinant expression vector of claim 9 wherein the DNA insert encodes a tip adhesin protein comprising an amino acid sequence of SEQ ID NO:9.

11. The recombinant expression vector of claim 9 wherein the DNA insert encodes an amino acid sequence consisting of SEQ ID NO:11.

12. A method of producing nontypable *Haemophilus influenzae* serotype 10, serotype 11 or serotype 12 LKP pilus proteins in a procaryotic or eucaryotic host cell comprising the steps of:

a) introducing a serotype 10, serotype 11 or serotype 12 LKP operon DNA insert which encodes the LKP pilus proteins into an expression vector which expresses at least one LKP pilus protein in the host cell, thereby producing a nontypable *Haemophilus influenzae* LKP pilus protein expression vector; and b) transfecting the host cell with the expression vector produced in step a) and maintaining the transfected host cell under conditions suitable for the expression of nontypable *Haemophilus influenzae* LKP pilus proteins in the host cell.

13. The method of claim 12 wherein the LKP pilus protein is tip adhesin protein.

* * * * *

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
       (A) LENGTH: 217 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

```
Met Glu Gln Phe Ile Met Lys Lys Thr Thr Gly Ser Leu Ile Leu
1               5                   10                  15

Leu Ala Phe Ala Thr Asn Ala Ala Asp Pro Gln Val Ser Thr Glu Thr
                20                  25                  30

Ser Gly Lys Val Thr Phe Phe Gly Lys Val Val Glu Asn Thr Cys Lys
            35                  40                  45

Val Lys Thr Asp Ser Lys Asn Met Ser Val Val Leu Asn Asp Val Gly
    50                  55                  60

Lys Asn His Leu Lys Thr Lys Lys Asp Thr Ala Met Pro Thr Pro Phe
65                  70                  75                  80

Thr Ile Asn Leu Glu Asn Cys Ser Thr Thr Thr Thr Thr Asn Asn Lys
                85                  90                  95

Pro Val Ala Thr Lys Val Gly Ala Tyr Phe Tyr Ser Trp Lys Asn Ala
                100                 105                 110

Asp Glu Asn Asn Glu Tyr Thr Leu Lys Asn Thr Lys Ser Gly Asn Asp
            115                 120                 125

Ala Ala Gln Asn Val Asn Ile Gln Thr Phe Asp Ala Asn Gly Thr Asp
        130                 135                 140

Ala Ile Glu Val Val Gly Asn Gly Thr Thr Asp Phe Thr His Ser Asn
145                 150                 155                 160

Thr Asn Asp Val Ala Thr Gln Gln Thr Val Asn Lys Asn His Ile Ser
                165                 170                 175

Gly Lys Ala Thr Ile Asn Gly Glu Asn Asn Val Lys Leu His Tyr Ile
```

```
                        180              185              190
Ala Arg Tyr Tyr Ala Thr Ala Gln Ala Glu Ala Gly Lys Val Glu Ser
        195              200              205

Ser Val Asp Phe Gln Ile Ala Tyr Glu
    210              215

(2) INFORMATION FOR SEQ ID NO:2:

(i) SEQUENCE CHARACTERISTICS:
        (A) LENGTH: 216 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Met Glu Gln Phe Ile Met Lys Lys Thr Leu Leu Gly Ser Leu Ile Leu
1               5                   10                  15

Leu Ala Phe Ala Gly Asn Val Gln Ala Asp Ile Asn Thr Glu Thr Ser
            20                  25                  30

Gly Lys Val Thr Phe Phe Gly Lys Val Val Glu Asn Thr Cys Lys Val
        35                  40                  45

Lys Thr Glu His Lys Asn Leu Ser Val Val Leu Asn Asp Val Gly Lys
    50                  55                  60

Asn Ser Leu Ser Thr Lys Val Asn Thr Ala Met Pro Thr Pro Phe Thr
65                  70                  75                  80

Ile Thr Leu Gln Asn Cys Asp Pro Thr Thr Ala Asn Gly Thr Ala Asn
                    85                  90                  95

Lys Ala Asn Lys Val Gly Leu Tyr Phe Tyr Ser Trp Lys Asn Val Asp
                100                 105                 110

Lys Glu Asn Asn Phe Thr Leu Lys Glu Gln Thr Thr Ala Asn Asp Tyr
                115                 120                 125

Ala Thr Asn Val Asn Ile Gln Leu Met Glu Ser Asn Gly Thr Lys Ala
        130                 135                 140

Ile Ser Val Val Gly Lys Glu Thr Glu Asp Phe Met His Thr Asn Asn
145                 150                 155                 160

Asn Gly Val Ala Leu Asn Gln Thr Pro Asn Asn Thr His Ile Ser Gly
                    165                 170                 175

Ser Thr Gln Leu Thr Gly Thr Asn Glu Leu Pro Leu His Phe Ile Ala
                180                 185                 190

Gln Tyr Tyr Ala Thr Asn Lys Ala Thr Ala Gly Lys Val Gln Ser Ser
        195                 200                 205

Val Asp Phe Gln Ile Ala Tyr Glu
    210                 215

(2) INFORMATION FOR SEQ ID NO:3:

(i) SEQUENCE CHARACTERISTICS:
        (A) LENGTH: 214 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Met Glu Gln Phe Ile Met Lys Lys Thr Leu Leu Gly Ser Leu Ile Leu
1               5                   10                  15

Leu Ala Phe Ala Gly Asn Val Gln Ala Ala Asp Pro Asn Pro Glu Thr
```

```
                       20                  25                  30
Lys Gly Lys Val Thr Phe Tyr Gly Lys Val Val Glu Asn Thr Cys Lys
        35                  40                  45
Val Lys Ser Gly Asn Arg Asp Met Ser Val Val Leu Asn Asp Val Gly
 50                  55                  60
Lys Ala His Leu Ser Gln Lys Gly Tyr Thr Ala Met Pro Thr Pro Phe
 65                  70                  75                  80
Thr Ile Thr Leu Glu Gly Cys Asn Ala Asn Thr Gly Thr Lys Pro Lys
                85                  90                  95
Ala Asn Lys Val Gly Val Tyr Phe Tyr Ser Trp Asn Asn Ala Asp Lys
            100                 105                 110
Glu Asn Ser Tyr Thr Leu Lys Ser Thr Leu Thr Gly Thr Asp Lys Ala
            115                 120                 125
Asp Asn Val Asn Ile Gln Ile Phe Gln Glu Asn Gly Thr Asp Ala Ile
130                 135                 140
Gly Val Ala Asp Lys Thr Ile Asp Asp Phe Thr His Lys Asn Asn Gly
145                 150                 155                 160
Ser Thr Asn Ser Asp Lys Pro Thr Lys Asn His Ile Ser Ser Ala Thr
                165                 170                 175
Ala Leu Asn Asn Gln Asp Gly Ile Ala Leu His Tyr Ile Ala Gln Tyr
            180                 185                 190
Tyr Ala Thr Gly Met Ala Ser Ala Gly Lys Gly Pro Thr Ser Val Asp
            195                 200                 205
Phe Pro Ile Ala Tyr Glu
            210

(2) INFORMATION FOR SEQ ID NO:4:

(i) SEQUENCE CHARACTERISTICS:
        (A) LENGTH: 9432 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: complement (1882..2532)

(ix) FEATURE:
        (A) NAME/KEY: CDS
        (B) LOCATION: 2854..3630

(ix) FEATURE:
        (A) NAME/KEY: CDS
        (B) LOCATION: 4016..6238

(ix) FEATURE:
        (A) NAME/KEY: CDS
        (B) LOCATION: 6259..6873

(ix) FEATURE:
        (A) NAME/KEY: CDS
        (B) LOCATION: 6955..8265

(ix) FEATURE:
        (A) NAME/KEY: CDS
        (B) LOCATION: 8395..9342

(xi) SEQUENCE DESCRIPTION: SEQ ID NO:4:

AAGCTTGCAT GCCTGCAGGT CGACTCTAGA GGATCATTCC ATTGTGTTTT ATCTTTTAAT      60

AAACACCAAG GTGAGGTAGA AATATTCAGT TCATCAAGCA AGGATTTTTG CGTAAAACGA     120

TCGGCTAATA ATCCAAATAC ATGTTGATTA ACGAAGTTTT TATGATTGCT GAGTAATTCA     180
```

```
GTCAAAGGCG TTTTTTCCCA GCGTTCAATT TCCGCCGTGA TGATCGCATT TTCAGGTAAG    240

TCAAAAACTG GCGCATTGAA GGCTAAGGGT TCAACATAAA TATCTAAAGG TGCACCAGCG    300

TAACCTAACA TTCTGCCGAG TTGTCCGTTG CCGAGAACAT AAACGGTTGG GTATAAGGTG    360

GAGTTTTGCA TAATATTTCT CGTTAAATTT ACGAAAAAAC AACCGCACTT TAAAAGTGCG    420

GTCAGATCTG AAGATATTTT TATGTGCGTG GATCGGGATT GTCCAGTACA GCACGAGTTT    480

GGCTTTCACG GAAAGATTGC AAGCGTGAAA GCAATTCTGC ATCCCAACCT GCTAGAATTT    540

GGGCTGCTAA CAACCCAGCA TTTGCCGCGC CTGCAGAGCC AATCGCTAAT GTTCCGACTG    600

GAATCCCTTT TGGCATTTGC ACAATTGAAT AAAGGCTATC CACACCACTT AACATAGAAC    660

TTTTTACTGG CACCCCCAGC ACTGGCACAA GTGTTTTGGC TGCGATCATA CCAGGTAAAT    720

GTGCCGCACC GCCTGCACCA GCAATAATTA CTTTATAGCC ATTTTTTTGT GCATTTCGG     780

CAAATTCGAA AAGTTTATCA GGCGTACGAT GGGCAGAGAC GACTTCCACA TGATAAGGCA    840

CGTTTAATTC ATCTAAAATC TGAGTTGCCT CTTGCATAGT AGCCCAATCA CTTTTTGACC    900

CCATCACAAC GGCAATTTGT GCAGTTTTTG ACATGCTATT TTCTCAATTT TCTAATTAAA    960

AACGTGGTGT AGAATAGCAT AGATTACATA TATCGAGCAA ACGTTTGCTA TTTATGTACG   1020

TATTAATGGG GATTATTTTA TAATTATTTG ATTTTTAAAT TTTAGTAACT ATACTTGATA   1080

CCAAATTAAT GGGCGATAGT TTATATGGGA CGAACTGAAA AATTATTAGA TAAGCTCGCA   1140

CAATCAAAAT CTACATTTAA TTGGAATGAA TTAGTTTCTT TGTTAGCTCA ACAAGGTTAT   1200

GAAAAGCGAG AAATGGCAGG TTCTCGAGTG AGATTTTATA ATAGAACACT CGAACATATG   1260

ATTTTGTTAC ACAAGCCTCA TCCTGAAAAT TATATTAAAG GCGGTGTTTT AAAGTCAGTG   1320

AAAGAATCAT TAAAACAGGT AGGTATTCTA TGAAGTTATT AAATTATAAA GGTTATGTTG   1380

GCACGATTGA GGCGGATTTA GAAAACAATA TATTATTTGG CAAACTTGCT TACATTCGTG   1440

ATTTAGTGAC TTACGAAGCA GAGTCATTAT CTGAGTTAGA AAAAGAATTT CATCAATCTG   1500

TTGATTTATA TTTACAAGAT TGTTTGGAAT TAGGTAAAGA ACCGAATAAG CCTTTTAAAG   1560

GTGTATTTAA TGTACGAATT GGCGAGGAAT TGCATAGAGA AGCAACGATC ATAGCTGGCG   1620

ATCGTTCTCT TAATGCTTTT GTGACGGAAG CAATTAAAGA AAAAATTTTT CGTGAAAAAC   1680

CAAGTTTAAG ATAACAAAAC GTATTTACAT TTTTTTTCAT CACGTAGGCT GGGCGTAAGC   1740

CCATGTAGAG ACACATAAAA AAGATTTGTA GGCTAGGCGT AAGCTCACGT GGATACATAT   1800

AAAAAAGATT TGTAGGGTGG GCGTAAGCCC ACGCAGGATA TAACAAACAC GTGGGCTTAG   1860

ATTGCATTAC ATTAGGAATT ATTCGTAAGC AATTTGGAAA TCAACTGAGG ATTCTACTTT   1920

ACCAGCTTCC GCTTGAGCTG TTGCATAGTA TCTAGCGATA TAGTGTAATT TCACATTGTT   1980

TTCACCGTTA ATTGTAGCTT TTCCTGAAAT ATGATTTTTA TTCACAGTTT GTTGTGTTGC   2040

AACGTCATTT GTATTGCTAT GCGTAAAATC TGTTGTTCCG TTGCCGACAA CTTCAATTGC   2100

ATCTGTACCA TTAGCATCAA AAAGCTGGAT ATTAACATTC TGTGCAGCAT CATTTCCTGA   2160

TTTTGTATTT TTTAATGTAT ATTCATTATT TTCATCTGCA TTTTTCCAAG AATAGAAATA   2220

AGCTCCAACT TTTGTTGCAA CAGGCTTATT ATTAGTAGTA GTAGTAGTAG AACAATTTTC   2280

TAAATTAATT GTAAATGGTG TTGGCATCGC TGTATCTTTT TTAGTTTTTA AATGATTTTT   2340

ACCCACATCA TTTAATACTA CGCTCATATT TTTACTATCC GTTTTCACTT TACAAGTATT   2400

CTCAACAACC TTACCAAAGA AAGTAACTTT ACCAGATGTT TCAGTACTTA CTTGAGGATC   2460

AGCAGCATTC GTTGCAAATG CCAATAAAAT TAAGCTACCA AGAAGTGTTT TTTTCATAAT   2520

AAATTGCTCC ATAAAGAGGT TTGTGCCTTA TAAATAAGGC AATAAAGATT AATATAAACC   2580
```

```
GTTTATTAAA ATGCCAAAGG CTTAATAAAC AGCAAACTTT GTTTTCCCAA AAAAAGTAAA      2640

AAACTCTTCC ATTATATATA TATATATATA TAATTAAAGC CCTTTTTGAA AAATTTCATA      2700

TTTTTTTGAA TTAATTCGCT GTAGGTTGGG TTTTTGCCCA CATGGAGACA TATAAAAAAG      2760

ATTTGTAGGG TGGGCGTAAG CCCACGCGGA ACATCATCAA ACAACTGTAA TGTTGTATTA      2820

GGCACGGTGG GCTTATGCCT CGCCTACGGG GAA ATG AAT AAG GAT AAA TAT GGG      2874
                                    Met Asn Lys Asp Lys Tyr Gly
                                     1               5

CTT AGC CCA GTT TAT GGA TTT AAT TAT GTT GAA ATG GGG AAA ACA ATG      2922
Leu Ser Pro Val Tyr Gly Phe Asn Tyr Val Glu Met Gly Lys Thr Met
        10                  15                  20

TTT AAA AAA ACA CTT TTA TTT TTT ACC GCA CTA TTT TTT GCC GCA CTT      2970
Phe Lys Lys Thr Leu Leu Phe Phe Thr Ala Leu Phe Phe Ala Ala Leu
 25                  30                  35

TGT GCA TTT TCA GCC AAT GCA GAT GTG ATT ATC ACT GGC ACC AGA GTG      3018
Cys Ala Phe Ser Ala Asn Ala Asp Val Ile Ile Thr Gly Thr Arg Val
 40                  45                  50                  55

ATT TAT CCC GCT GGG CAA AAA AAT GTT ATC GTG AAG TTA GAA AAC AAT      3066
Ile Tyr Pro Ala Gly Gln Lys Asn Val Ile Val Lys Leu Glu Asn Asn
             60                  65                  70

GAT GAT TCG GCA GCA TTG GTG CAA GCC TGG ATT GAT AAT GGC AAT CCA      3114
Asp Asp Ser Ala Ala Leu Val Gln Ala Trp Ile Asp Asn Gly Asn Pro
             75                  80                  85

AAT GCC GAT CCA AAA TAC ACC AAA ACC CCT TTT GTG ATT ACC CCG CCT      3162
Asn Ala Asp Pro Lys Tyr Thr Lys Thr Pro Phe Val Ile Thr Pro Pro
             90                  95                 100

GTT GCT CGA GTG GAA GCG AAA TCA GGG CAA AGT TTG CGG ATT ACG TTC      3210
Val Ala Arg Val Glu Ala Lys Ser Gly Gln Ser Leu Arg Ile Thr Phe
105                 110                 115

ACA GGC AGC GAG CCT TTA CCT GAT GAT CGC GAA AGC CTC TTT TAT TTT      3258
Thr Gly Ser Glu Pro Leu Pro Asp Asp Arg Glu Ser Leu Phe Tyr Phe
120                 125                 130                 135

AAT TTG TTA GAT ATT CCG CCG AAA CCT GAT GCG GCA TTT CTG GCA AAA      3306
Asn Leu Leu Asp Ile Pro Pro Lys Pro Asp Ala Ala Phe Leu Ala Lys
             140                 145                 150

CAC GGC AGC TTT ATG CAA ATT GCC ATT CGC TCA CGT TTG AAG TTG TTT      3354
His Gly Ser Phe Met Gln Ile Ala Ile Arg Ser Arg Leu Lys Leu Phe
             155                 160                 165

TAT CGC CCT GCG AAA CTC TCG ATG GAT TCT CGT GAT GCA ATG AAA AAA      3402
Tyr Arg Pro Ala Lys Leu Ser Met Asp Ser Arg Asp Ala Met Lys Lys
             170                 175                 180

GTA GTG TTT AAA GCC ACA CCT GAA GGG GTG TTG GTG GAT AAT CAA ACC      3450
Val Val Phe Lys Ala Thr Pro Glu Gly Val Leu Val Asp Asn Gln Thr
185                 190                 195

CCT TAT TAT ATG AAC TAC ATT GGT TTG TTA CAT CAA AAT AAA CCT GCG      3498
Pro Tyr Tyr Met Asn Tyr Ile Gly Leu Leu His Gln Asn Lys Pro Ala
200                 205                 210                 215

AAA AAT GTC AAA ATG GTT GCC CCT TTT TCT CAA GCG GTA TTT GAA GCC      3546
Lys Asn Val Lys Met Val Ala Pro Phe Ser Gln Ala Val Phe Glu Ala
                 220                 225                 230

AAA GGC GTG CGT TCT GGC GAT AAA TTG AAA TGG GTA TTG GTT AAT GAT      3594
Lys Gly Val Arg Ser Gly Asp Lys Leu Lys Trp Val Leu Val Asn Asp
             235                 240                 245

TAC GGT GCC GAC CAA GAA GGC GAA GCC ATC GCT CAA TAATAGCGAA          3640
Tyr Gly Ala Asp Gln Glu Gly Glu Ala Ile Ala Gln
        250                 255

CTAGTGTAGG GTGGGCTTTA GACCACCGAT TAACCATAAC AAAGGTGGGC TGAAGCCCAC      3700

CCTACAACCA CAAAGAACGA TTAATCTGTG AAAACAAAAA TTTTTCCCTT AAATAAAATT      3760
```

```
GCGTTTGCTT GTTCACTGCT ATTGGCAAAT CCTTTAGCGT GGGCGGGAGA TCAATTTGAT    3820

GCCTCTCTTT GGGGAGATGG TTCGGTGTTG GGCGTTGATT TTGCCCGATT TAATGTAAAA    3880

AATGCCGTGT TACCAGGGCG TTATGAAGCT CAAATCTATG TGAAATTTGA AGAAAAAGGC    3940

GTAAGCGATA TTATTTTTGC TGATAATCCT GCCACAGGTC GGACAGAATT ATGCTTTACG    4000

CCTAAACTTC AAGAA ATG CTG GAT TTG ATG GAT GAA GCC ATT GTG AAA TCG    4051
                Met Leu Asp Leu Met Asp Glu Ala Ile Val Lys Ser
                  1               5                  10

CCC AAT TCA GAA GAT GAC ACT TGT GTC TTT GCT TCT GAT GCT ATT CCT    4099
Pro Asn Ser Glu Asp Asp Thr Cys Val Phe Ala Ser Asp Ala Ile Pro
             15                  20                  25

AAA GGC ACG TTT GAA TAT CAA AGC GGC GAA ATG AAA TTG AAA CTT GAG    4147
Lys Gly Thr Phe Glu Tyr Gln Ser Gly Glu Met Lys Leu Lys Leu Glu
         30                  35                  40

CTC CCT CAA GCT CTC ACT ATT CGC CGA CCA AGA GGC TAT ATT GCG CCA    4195
Leu Pro Gln Ala Leu Thr Ile Arg Arg Pro Arg Gly Tyr Ile Ala Pro
     45                  50                  55                  60

TCT CGC TGG CAA ACT GGC ACC AAT GCC GCT TTT GCA AAT TAC GAT ATC    4243
Ser Arg Trp Gln Thr Gly Thr Asn Ala Ala Phe Ala Asn Tyr Asp Ile
                 65                  70                  75

AAC TAT TAT CGT TCT GGT AAT CCC GAA GTA AAA TCC GAA AGT TTG TAT    4291
Asn Tyr Tyr Arg Ser Gly Asn Pro Glu Val Lys Ser Glu Ser Leu Tyr
             80                  85                  90

GTG GGC TTG CGT AGT GGC GTA AAT TTT GGC AAC TGG GCA TTG CGT CAT    4339
Val Gly Leu Arg Ser Gly Val Asn Phe Gly Asn Trp Ala Leu Arg His
         95                 100                 105

AGC GGC AGT TTT AGC CGT TTT GAA AAC CAA AGT AGC TCG GGT TTT ACT    4387
Ser Gly Ser Phe Ser Arg Phe Glu Asn Gln Ser Ser Ser Gly Phe Thr
    110                 115                 120

GAT AAG GGC AAA AAT CAT TAC GAA CGT GGC GAT ACC TAT TTA CAA CGA    4435
Asp Lys Gly Lys Asn His Tyr Glu Arg Gly Asp Thr Tyr Leu Gln Arg
125                 130                 135                 140

GAT TTC GCC CTG CTT CGT GGC AAT GTC ACT GTT GGG GAT TTT TTC AGC    4483
Asp Phe Ala Leu Leu Arg Gly Asn Val Thr Val Gly Asp Phe Phe Ser
                145                 150                 155

ACT GCC CGC ATT GGC GAA AAT TTT GGT ATG CGT GGT TTG CGT ATT GCC    4531
Thr Ala Arg Ile Gly Glu Asn Phe Gly Met Arg Gly Leu Arg Ile Ala
            160                 165                 170

TCT GAT GAT AGA ATG CTT GCC CCA TCA CAA CGT GGT TTT GCC CCA GTG    4579
Ser Asp Asp Arg Met Leu Ala Pro Ser Gln Arg Gly Phe Ala Pro Val
        175                 180                 185

GTG CGT GGC GTG GCA AAC ACA AAC GCC AAA GTC AGC ATC AAA CAA AAT    4627
Val Arg Gly Val Ala Asn Thr Asn Ala Lys Val Ser Ile Lys Gln Asn
    190                 195                 200

GGC TAT ACG ATT TAT CAA ATC ACC GTT CCC GCA GGG CCT TTC GTG ATT    4675
Gly Tyr Thr Ile Tyr Gln Ile Thr Val Pro Ala Gly Pro Phe Val Ile
205                 210                 215                 220

AAC GAT TTG TAT GCC AGC GGT TAT AGC GGC GAT TTA ACG GTG GAA ATC    4723
Asn Asp Leu Tyr Ala Ser Gly Tyr Ser Gly Asp Leu Thr Val Glu Ile
                225                 230                 235

CAA GAA AGT GAT GGT AAA GTG CGG TCA TTT ATT GTG CCG TTT TCT AAT    4771
Gln Glu Ser Asp Gly Lys Val Arg Ser Phe Ile Val Pro Phe Ser Asn
            240                 245                 250

CTT GCC CCG TTA ATG CGT GTG GGG CAT TTG CGT TAT CAA TTA GCT GGC    4819
Leu Ala Pro Leu Met Arg Val Gly His Leu Arg Tyr Gln Leu Ala Gly
        255                 260                 265

GGA CGT TAT CGA ATT GAC AGC CGC ACC TTT GAT GAA CGT GTG TTA CAA    4867
Gly Arg Tyr Arg Ile Asp Ser Arg Thr Phe Asp Glu Arg Val Leu Gln
    270                 275                 280
```

```
GGC GTG TTG CAA TAT GGT TTA ACT AAT CAT CTC ACG CTG AAT TCA AGC      4915
Gly Val Leu Gln Tyr Gly Leu Thr Asn His Leu Thr Leu Asn Ser Ser
285                 290                 295                 300

CTG CTT TAT ACA CGT CAT TAT CGT GCA GGG CTG TTT GGT TTT GGT TTA      4963
Leu Leu Tyr Thr Arg His Tyr Arg Ala Gly Leu Phe Gly Phe Gly Leu
                305                 310                 315

AAT ACG CCG ATT GGG GCG TTT TCT GCT GAT GCC ACT TGG TCG CAC GCT      5011
Asn Thr Pro Ile Gly Ala Phe Ser Ala Asp Ala Thr Trp Ser His Ala
            320                 325                 330

GAA TTT CCG CTA AAA CAT GTG AGC AAA AAC GGC TAC AGC TTG CAC GGC      5059
Glu Phe Pro Leu Lys His Val Ser Lys Asn Gly Tyr Ser Leu His Gly
        335                 340                 345

AGT TAT AGT ATT AAC TTC AAT GAA AGT GGC ACC AAT ATC ACG TTG GCA      5107
Ser Tyr Ser Ile Asn Phe Asn Glu Ser Gly Thr Asn Ile Thr Leu Ala
    350                 355                 360

GCC TAT CGC TAT TCT TCA CGG GAT TTT TAC ACC TTA AGC GAC ACC ATT      5155
Ala Tyr Arg Tyr Ser Ser Arg Asp Phe Tyr Thr Leu Ser Asp Thr Ile
365                 370                 375                 380

GGT CTT AAC CGC ACT TTC AGA CAA TTT AGC GGT GCG TAT TTG CCT GAA      5203
Gly Leu Asn Arg Thr Phe Arg Gln Phe Ser Gly Ala Tyr Leu Pro Glu
                385                 390                 395

ATT TAC CGC CCA AAA AAT CAG TTT CAA GTG AGT TTA AGC CAA AGT CTG      5251
Ile Tyr Arg Pro Lys Asn Gln Phe Gln Val Ser Leu Ser Gln Ser Leu
            400                 405                 410

GGG AAT TGG GGA AAT CTC TAT CTT TCA GGA CAA ACC TAT AAT TAT TGG      5299
Gly Asn Trp Gly Asn Leu Tyr Leu Ser Gly Gln Thr Tyr Asn Tyr Trp
        415                 420                 425

GAA AAA CGT GGC ACG AAT ACG CAA TAT CAA GTT GCC TAT TCA AAC AGC      5347
Glu Lys Arg Gly Thr Asn Thr Gln Tyr Gln Val Ala Tyr Ser Asn Ser
    430                 435                 440

TTC CAC ATT CTT AAT TAC TCT GTA AAC CTC TCA CAG AGT ATT GAT AAA      5395
Phe His Ile Leu Asn Tyr Ser Val Asn Leu Ser Gln Ser Ile Asp Lys
445                 450                 455                 460

GAA ACG GGC AAA CGT GAC AAC AGC ATT TAT TTA AGT CTC AGC CTG CCA      5443
Glu Thr Gly Lys Arg Asp Asn Ser Ile Tyr Leu Ser Leu Ser Leu Pro
                465                 470                 475

TTA GGC GAT AAC CAT TCT GCA GAT AGT AGT TAT TCT CGC AGT GGT AAC      5491
Leu Gly Asp Asn His Ser Ala Asp Ser Ser Tyr Ser Arg Ser Gly Asn
            480                 485                 490

GAT ATT AAC CAA CGA CTT GGC GTA AAT GGC TCT TTT GGT GAA CGT CAT      5539
Asp Ile Asn Gln Arg Leu Gly Val Asn Gly Ser Phe Gly Glu Arg His
        495                 500                 505

CAA TGG AGT TAT GGT ATT AAC GCT TCA CGC AAT AAT CAA GGC TAT CGC      5587
Gln Trp Ser Tyr Gly Ile Asn Ala Ser Arg Asn Asn Gln Gly Tyr Arg
    510                 515                 520

AGT TAT GAC GGT AAT CTT TCG CAT AAC AAT AGC ATT GGT AGT TAC CGT      5635
Ser Tyr Asp Gly Asn Leu Ser His Asn Asn Ser Ile Gly Ser Tyr Arg
525                 530                 535                 540

GCT TCT TAT TCA CGT GAT AGC CTC AAA AAT CGC TCC ATC TCA CTG GGC      5683
Ala Ser Tyr Ser Arg Asp Ser Leu Lys Asn Arg Ser Ile Ser Leu Gly
                545                 550                 555

GCA AGC GGT GCT GTC GTG GCG CAC AAA CAC GGT ATT ACC TTA AGC CAA      5731
Ala Ser Gly Ala Val Val Ala His Lys His Gly Ile Thr Leu Ser Gln
            560                 565                 570

CCT GTT GGC GAA AGT TTT GCC ATT ATT CAC GCC AAA GAT GCC GCA GGA      5779
Pro Val Gly Glu Ser Phe Ala Ile Ile His Ala Lys Asp Ala Ala Gly
        575                 580                 585

GCA AAA GTG GAA TCA GGT GCC AAT GTG AGC CTT GAT TAT TTC GGC AAT      5827
Ala Lys Val Glu Ser Gly Ala Asn Val Ser Leu Asp Tyr Phe Gly Asn
    590                 595                 600
```

```
GCG GTT ATG CCT TAC ACC AGC CCG TAT GAA ATC AAT TAT ATC GGT ATC        5875
Ala Val Met Pro Tyr Thr Ser Pro Tyr Glu Ile Asn Tyr Ile Gly Ile
605                 610                 615                 620

AAT CCA TCT GAT GCG GAG GCG AAT GTG GAA TTT GAA GCC ACT GAA CGC        5923
Asn Pro Ser Asp Ala Glu Ala Asn Val Glu Phe Glu Ala Thr Glu Arg
                    625                 630                 635

CAA ATC ATT CCT CGT GCA AAT TCA ATT AGC TTA GTA GAT TTC CGC ACG        5971
Gln Ile Ile Pro Arg Ala Asn Ser Ile Ser Leu Val Asp Phe Arg Thr
                640                 645                 650

GGC AAA AAT ACA ATG GTG TTA TTT AAC CTC ACT TTG CCA AAT GGC GAG        6019
Gly Lys Asn Thr Met Val Leu Phe Asn Leu Thr Leu Pro Asn Gly Glu
            655                 660                 665

CCA GTG CCA ATG GCA TCC ACC GCA CAA GAT AGC GAA GGG GCA TTT GTG        6067
Pro Val Pro Met Ala Ser Thr Ala Gln Asp Ser Glu Gly Ala Phe Val
        670                 675                 680

GGC GAT GTG GTG CAA GGT GGT GTG CTT TTC GCT AAT AAA CTT ACC CAG        6115
Gly Asp Val Val Gln Gly Gly Val Leu Phe Ala Asn Lys Leu Thr Gln
685                 690                 695                 700

CCA AAA GGC GAG TTA ATC GTC AAA TGG GGT GAG CGA GAA AGC GAA CAA        6163
Pro Lys Gly Glu Leu Ile Val Lys Trp Gly Glu Arg Glu Ser Glu Gln
                705                 710                 715

TGC CGT TTC CAA TAT CAA GTT GAT TTG GAT AAC GCA CAA ATA CAA AGT        6211
Cys Arg Phe Gln Tyr Gln Val Asp Leu Asp Asn Ala Gln Ile Gln Ser
                720                 725                 730

CAC GAT ATT CAA TGC AAA ACC GCA AAA TAAATAATTG AAGAGGATTT ATG          6261
His Asp Ile Gln Cys Lys Thr Ala Lys                         Met
            735                 740                          1

CAA AAA ACA CCC AAA AAA TTA ACC GCG CTT TTC CAT CAA AAA TCC ACT        6309
Gln Lys Thr Pro Lys Lys Leu Thr Ala Leu Phe His Gln Lys Ser Thr
                 5                  10                  15

GCT ACT TGT AGT GGA GCA AAT TAT AGT GGA GCA AAT TAT AGT GGC TCA        6357
Ala Thr Cys Ser Gly Ala Asn Tyr Ser Gly Ala Asn Tyr Ser Gly Ser
         20                  25                  30

AAA TGC TTT AGG TTT CAT CGT CTG GCT CTG CTT GCT TGC GTG GCT CTG        6405
Lys Cys Phe Arg Phe His Arg Leu Ala Leu Leu Ala Cys Val Ala Leu
 35                  40                  45

CTT GAT TGC ATT GTG GCA CTG CCT GCT TAT GCT TAC GAT GGC AGA GTG        6453
Leu Asp Cys Ile Val Ala Leu Pro Ala Tyr Ala Tyr Asp Gly Arg Val
 50                  55                  60                  65

ACC TTT CAA GGG GAG ATT TTA AGT GAT GGC ACT TGT AAA ATT GAA ACA        6501
Thr Phe Gln Gly Glu Ile Leu Ser Asp Gly Thr Cys Lys Ile Glu Thr
                 70                  75                  80

GAC AGC CAA AAT CGC ACG GTT ACC CTG CCA ACA GTG GGA AAA GCT AAT        6549
Asp Ser Gln Asn Arg Thr Val Thr Leu Pro Thr Val Gly Lys Ala Asn
             85                  90                  95

TTA AGC CAC GCA GGG CAA ACC GCC GCC CCT GTG CCT TTT TCC ATC ACG        6597
Leu Ser His Ala Gly Gln Thr Ala Ala Pro Val Pro Phe Ser Ile Thr
        100                 105                 110

TTA AAA GAA TGC AAT GCA GAT GAT GCT ATG AAA GCT AAT CTG CTA TTT        6645
Leu Lys Glu Cys Asn Ala Asp Asp Ala Met Lys Ala Asn Leu Leu Phe
115                 120                 125

AAA GGG GGA GAC AAC ACA ACA GGG CAA TCT TAT CTT TCC AAT AAG GCA        6693
Lys Gly Gly Asp Asn Thr Thr Gly Gln Ser Tyr Leu Ser Asn Lys Ala
130                 135                 140                 145

GGC AAC GGC AAA GCC ACC AAC GTG GGC ATT CAA ATT GTC AAA GCC GAT        6741
Gly Asn Gly Lys Ala Thr Asn Val Gly Ile Gln Ile Val Lys Ala Asp
                150                 155                 160

GGC ATA GGC ACG CCT ATC AAG GTG GAC GGC ACC GAA GCC AAC AGC GAA        6789
Gly Ile Gly Thr Pro Ile Lys Val Asp Gly Thr Glu Ala Asn Ser Glu
            165                 170                 175
```

```
AAA GCC CCC GAC ACA GGT AAA GCG CAA AAC GGC ACA GTT ATT CAA CCC        6837
Lys Ala Pro Asp Thr Gly Lys Ala Gln Asn Gly Thr Val Ile Gln Pro
        180                 185                 190

CGT TTT GGC TAC TTT GGC TCG TTA TTA CGC CAC AGG TGAAGCCACC             6883
Arg Phe Gly Tyr Phe Gly Ser Leu Leu Arg His Arg
    195                 200                 205

GCAGGCGACG TTGAAGCCAC TGCAACTTTT GAAGTGCAGT ATAACTAAAA TATTTATTAT      6943

CCAGTGAAAA A ATG AAT AAG AAA TCG TAT ATA AAT CAT TAC TTA ACT TTA       6993
             Met Asn Lys Lys Ser Tyr Ile Asn His Tyr Leu Thr Leu
              1               5                   10

TTT AAA GTT ACT ACT TTA CTA TTT ACT CTT TCA AGT AAT CCT GTA TGG        7041
Phe Lys Val Thr Thr Leu Leu Phe Thr Leu Ser Ser Asn Pro Val Trp
        15              20                  25

GCA AAT ATA AAA ACA GTT CAG GGA ACA ACT AGT GGT TTT CCA CTT CTA        7089
Ala Asn Ile Lys Thr Val Gln Gly Thr Thr Ser Gly Phe Pro Leu Leu
30              35                  40                  45

ACA AGA ACT TTC ACA TTT AAT GGC AAT TTG CAA TGG AAT GTG AGT GCT        7137
Thr Arg Thr Phe Thr Phe Asn Gly Asn Leu Gln Trp Asn Val Ser Ala
                50                  55                  60

CTA CAA CCA GCT TAT ATT GTT TCC TCT CAA GCA AGA GAT AAT CTT GAT        7185
Leu Gln Pro Ala Tyr Ile Val Ser Ser Gln Ala Arg Asp Asn Leu Asp
            65                  70                  75

ACA GTA CAT ATT CAA TCT TCT GAA ATT AAT GCT CCA ACA AAT TCA TTA        7233
Thr Val His Ile Gln Ser Ser Glu Ile Asn Ala Pro Thr Asn Ser Leu
        80                  85                  90

GCT CCA TTT AAT AAT TGG ATT AAT ACG AAA TCA GCA GTA GAG CTA GGT        7281
Ala Pro Phe Asn Asn Trp Ile Asn Thr Lys Ser Ala Val Glu Leu Gly
    95                  100                 105

TAT AGC TTT GCG GGC ATT ACT TGT ACT AGT AAT CCT TGC CCA ACA ATG        7329
Tyr Ser Phe Ala Gly Ile Thr Cys Thr Ser Asn Pro Cys Pro Thr Met
110             115                 120                 125

AAA TTA CCA TTA TTA TTT CAT CCT GAT CTT ACT AAT TTA ACT CCA CCT        7377
Lys Leu Pro Leu Leu Phe His Pro Asp Leu Thr Asn Leu Thr Pro Pro
                130                 135                 140

GGA AAG AAA AAT TCT GAT GGA GGG GAG ATT TTT AAA TTA CAT AAT GAA        7425
Gly Lys Lys Asn Ser Asp Gly Gly Glu Ile Phe Lys Leu His Asn Glu
            145                 150                 155

TCT AAT TTA GGC GTC TCT TTT CAA ATT GGA GTA AAA ACG AAT ACT TCT        7473
Ser Asn Leu Gly Val Ser Phe Gln Ile Gly Val Lys Thr Asn Thr Ser
        160                 165                 170

CTA GAT TGG GTT AAT GCT AAG AAT AAT TTT AGC TCT CTA AAA GTT TTA        7521
Leu Asp Trp Val Asn Ala Lys Asn Asn Phe Ser Ser Leu Lys Val Leu
    175                 180                 185

ATG GTG CCT TTT AAT TCT AGC GAT AAA ATA TCT TTG CAT TTA CGT GCT        7569
Met Val Pro Phe Asn Ser Ser Asp Lys Ile Ser Leu His Leu Arg Ala
190             195                 200                 205

AAA TTT CAT TTA TTA ACA GAT TTT TCA TCG CTA AAT AAT GAT ATT ACT        7617
Lys Phe His Leu Leu Thr Asp Phe Ser Ser Leu Asn Asn Asp Ile Thr
                210                 215                 220

ATT GAC CCT ATG AAT ACT AGT ATA GGC AAA ATT AAT CTT GAA ACG TGG        7665
Ile Asp Pro Met Asn Thr Ser Ile Gly Lys Ile Asn Leu Glu Thr Trp
            225                 230                 235

CGT GGC TCA ACA GGC AAT TTT TCT GTT AAA TAT GTA GGT GAG GAT AAG        7713
Arg Gly Ser Thr Gly Asn Phe Ser Val Lys Tyr Val Gly Glu Asp Lys
        240                 245                 250

GGA GAT ATA TCT ATT TTC TTT AAT ACA CCT AAA ATT ATT CTA AAA AAA        7761
Gly Asp Ile Ser Ile Phe Phe Asn Thr Pro Lys Ile Ile Leu Lys Lys
    255                 260                 265

CAA CAA CGC CGA TGT ACT CTG AAT AAT GCT CCA GTG AGC CCA AAT CCA        7809
```

```
Gln Gln Arg Arg Cys Thr Leu Asn Asn Ala Pro Val Ser Pro Asn Pro
270                 275                 280                 285

GTT AAA TTA CGA GCG GTA AAA AAA CGT GAA TTG GAG GCA CAA AGT GAA     7857
Val Lys Leu Arg Ala Val Lys Lys Arg Glu Leu Glu Ala Gln Ser Glu
                290                 295                 300

ATG GAA GGT GGG ACA TTT CAG TTA AGA GTA AAT TGT GAC AAT ACC ACT     7905
Met Glu Gly Gly Thr Phe Gln Leu Arg Val Asn Cys Asp Asn Thr Thr
            305                 310                 315

TAT AAT AAA GCC AAC GGC AAA TGG TTA TTT CCT GTA GTG AAA GTT ACT     7953
Tyr Asn Lys Ala Asn Gly Lys Trp Leu Phe Pro Val Val Lys Val Thr
        320                 325                 330

TTT ACG GAC GAA GAT GGT ACA ACG AAT AAT GGA ACA AAT GAC TTA CTT     8001
Phe Thr Asp Glu Asp Gly Thr Thr Asn Asn Gly Thr Asn Asp Leu Leu
    335                 340                 345

CGC ACC CAA ACA GGC AGC GGA CAA GCC ACA GGC GTT AGC TTA AGA ATC     8049
Arg Thr Gln Thr Gly Ser Gly Gln Ala Thr Gly Val Ser Leu Arg Ile
350                 355                 360                 365

AAA CGA GAA AAT GGT ACA GAA ACC GTA AAA TAC GGT GCT GAT TCT GCT     8097
Lys Arg Glu Asn Gly Thr Glu Thr Val Lys Tyr Gly Ala Asp Ser Ala
                370                 375                 380

CAA ATG GGG AAT GCT GGA CAA TTT GAA TTA CGA AAA CAA CCA TCC CCT     8145
Gln Met Gly Asn Ala Gly Gln Phe Glu Leu Arg Lys Gln Pro Ser Pro
            385                 390                 395

GCT GGT GGA GAT CAA TAT GCT GAA GAA ACT TTC AAA GTC TAT TAC GTA     8193
Ala Gly Gly Asp Gln Tyr Ala Glu Glu Thr Phe Lys Val Tyr Tyr Val
        400                 405                 410

AAA GAC TCA ACA AGA GGC ACC TTA ATC GAA GGA AAA GTC AAA GCC GCC     8241
Lys Asp Ser Thr Arg Gly Thr Leu Ile Glu Gly Lys Val Lys Ala Ala
    415                 420                 425

GCC ACT TTC ACA ATG TCA TAT CAA TAATAATGTC GGGTGGGAAT ATAAAGGCTG    8295
Ala Thr Phe Thr Met Ser Tyr Gln
430                 435

AAGGTTTAAA CTTCAGTCTT TTTTTATAGG AAAATACCAT TGCAACTTTA AGGATAAAAT   8355

TTTATCCTAA GCACAATTTT TATAAGAATA GGTCAAATT ATG TTA GCC AAA GCA      8409
                                           Met Leu Ala Lys Ala
                                             1                 5

AAA TAT AGA AAA GAT TAC AAA CAA CCA GAT TTT ACG GTC ACA GAC ATT     8457
Lys Tyr Arg Lys Asp Tyr Lys Gln Pro Asp Phe Thr Val Thr Asp Ile
            10                  15                  20

TAT TTA GAT TTT CAA CTT GAT CCT AAA AAT ACT GTG GTG ACT GCA ACC     8505
Tyr Leu Asp Phe Gln Leu Asp Pro Lys Asn Thr Val Val Thr Ala Thr
        25                  30                  35

ACA AAA TTC CAA CGC TTA AAT AAT GAA GCG ACG TCT TTA CGT TTA GAC     8553
Thr Lys Phe Gln Arg Leu Asn Asn Glu Ala Thr Ser Leu Arg Leu Asp
    40                  45                  50

GGG CAT AGC TTC CAG TTT TCT TCT ATT AAA TTT AAT GGC GAG CCA TTT     8601
Gly His Ser Phe Gln Phe Ser Ser Ile Lys Phe Asn Gly Glu Pro Phe
55                  60                  65

TCT GAT TAT CAA CAA GAT GGC GAG AGT TTA ACG CTC GAT TTA AAA GAC     8649
Ser Asp Tyr Gln Gln Asp Gly Glu Ser Leu Thr Leu Asp Leu Lys Asp
70                  75                  80                  85

AAA AGT GCG GAT GAA TTT GAG CTT GAA ATT GTG ACG TTC CTT GTG CCA     8697
Lys Ser Ala Asp Glu Phe Glu Leu Glu Ile Val Thr Phe Leu Val Pro
                90                  95                  100

GCC GAA AAT ACG TCA TTA CAA GGG CTA TAT CAG TCT GGC GAA GGT ATT     8745
Ala Glu Asn Thr Ser Leu Gln Gly Leu Tyr Gln Ser Gly Glu Gly Ile
            105                 110                 115

TGT ACG CAA TGT GAG GCG GAA GGT TTC CGT CAA ATC ACT TAT ATG CTT     8793
Cys Thr Gln Cys Glu Ala Glu Gly Phe Arg Gln Ile Thr Tyr Met Leu
        120                 125                 130
```

```
GAT CGT CCT GAT GTG CTG GCG CGT TAT ATA ATC AAA ATT ACG GCA GAT            8841
Asp Arg Pro Asp Val Leu Ala Arg Tyr Ile Ile Lys Ile Thr Ala Asp
        135                 140                 145

AAA ACC AAA TAT CCA TTC TTA CTG TCG AAT GGT AAT CGC ATT GCA AGT            8889
Lys Thr Lys Tyr Pro Phe Leu Leu Ser Asn Gly Asn Arg Ile Ala Ser
150                 155                 160                 165

GGC GAA TTA GAA GAT GGT CGC CAT TGG GTG GAA TGG AAT GAT CCT TTC            8937
Gly Glu Leu Glu Asp Gly Arg His Trp Val Glu Trp Asn Asp Pro Phe
                170                 175                 180

CCA AAA CCA AGC TAT TTA TTT GCT TTA GTG GCG GGA GAT TNN GGT TTA            8985
Pro Lys Pro Ser Tyr Leu Phe Ala Leu Val Ala Gly Asp Xaa Gly Leu
            185                 190                 195

TTA CAA GAT AAN TTT ATT ACT AAA AGT GGT CGT GAA GTG GCT TTA GAG            9033
Leu Gln Asp Xaa Phe Ile Thr Lys Ser Gly Arg Glu Val Ala Leu Glu
        200                 205                 210

CTT TAT GTG GAT CGC GGT AAT CTT AAC CGT GCA ACT GGG GCA ATG GAA            9081
Leu Tyr Val Asp Arg Gly Asn Leu Asn Arg Ala Thr Gly Ala Met Glu
    215                 220                 225

AGT CTG AAA AAA GCG ATG AAA TGG GAT GAA GAT CGC TTT ATT TTA GAA            9129
Ser Leu Lys Lys Ala Met Lys Trp Asp Glu Asp Arg Phe Ile Leu Glu
230                 235                 240                 245

TTT TAC CTA GAT ATT TAT ATG ATC GCG GCC GCC GAT TCC TCC AAT ATG            9177
Phe Tyr Leu Asp Ile Tyr Met Ile Ala Ala Ala Asp Ser Ser Asn Met
                250                 255                 260

GGC GCA ATG GAA AAT AAA GGA TTA AAT ATC TTT AAC TCT AAA TTG GTG            9225
Gly Ala Met Glu Asn Lys Gly Leu Asn Ile Phe Asn Ser Lys Leu Val
            265                 270                 275

TTG GCA AAT CCA CAA ACG GCA ACA GAT GAA GAT TAT CTT GTC ATT GAA            9273
Leu Ala Asn Pro Gln Thr Ala Thr Asp Glu Asp Tyr Leu Val Ile Glu
        280                 285                 290

AGT GTG ATT GCA CAC GAA TAT TCC CAT AAC TGG ACG GGA AAC CGT GTA            9321
Ser Val Ile Ala His Glu Tyr Ser His Asn Trp Thr Gly Asn Arg Val
    295                 300                 305

ACC CGC CGA GAT GGG TTC AAC TAGGTTTGAA GAAGGTTAAC GGCTTCCGGG               9372
Thr Arg Arg Asp Gly Phe Asn
310                 315

AACAAGATTT CTCAGATCAG TTCTCCGGGC CGGAACCGAT TAATAAGGGA AAATTTTCCG          9432

(2) INFORMATION FOR SEQ ID NO:5:

(i) SEQUENCE CHARACTERISTICS:
        (A) LENGTH: 217 amino acids
        (B) TYPE: amino acid
        (D) TOPOLOGY: linear (ii) MOLECULE TYPE: protein (xi) SEQUENCE DESCRIPTION: SEQ ID NO:5:

Met Glu Gln Phe Ile Met Lys Lys Thr Leu Leu Gly Ser Leu Ile Leu
1               5                   10                  15

Leu Ala Phe Ala Thr Asn Ala Ala Asp Pro Gln Val Ser Thr Glu Thr
            20                  25                  30

Ser Gly Lys Val Thr Phe Phe Gly Lys Val Val Glu Asn Thr Cys Lys
        35                  40                  45

Val Lys Thr Asp Ser Lys Asn Met Ser Val Val Leu Asn Asp Val Gly
    50                  55                  60

Lys Asn His Leu Lys Thr Lys Lys Asp Thr Ala Met Pro Thr Pro Phe
65                  70                  75                  80

Thr Ile Asn Leu Glu Asn Cys Ser Thr Thr Thr Thr Asn Lys
                85                  90                  95
```

```
Pro Val Ala Thr Lys Val Gly Ala Tyr Phe Tyr Ser Trp Lys Asn Ala
            100                 105                 110

Asp Glu Asn Asn Glu Tyr Thr Leu Lys Asn Thr Lys Ser Gly Asn Asp
            115                 120                 125

Ala Ala Gln Asn Val Asn Ile Gln Leu Phe Asp Ala Asn Gly Thr Asp
            130                 135                 140

Ala Ile Glu Val Val Gly Asn Gly Thr Thr Asp Phe Thr His Ser Asn
145                 150                 155                 160

Thr Asn Asp Val Ala Thr Gln Gln Thr Val Asn Lys Asn His Ile Ser
                165                 170                 175

Gly Lys Ala Thr Ile Asn Gly Glu Asn Asn Val Lys Leu His Tyr Ile
                180                 185                 190

Ala Arg Tyr Tyr Ala Thr Ala Gln Ala Glu Ala Gly Lys Val Glu Ser
            195                 200                 205

Ser Val Asp Phe Gln Ile Ala Tyr Glu
            210                 215
```

(2) INFORMATION FOR SEQ ID NO:6:

(i) SEQUENCE CHARACTERISTICS:
        (A) LENGTH: 259 amino acids
        (B) TYPE: amino acid
        (D) TOPOLOGY: linear (ii) MOLECULE TYPE: protein (xi) SEQUENCE DESCRIPTION: SEQ ID NO:6:

```
Met Asn Lys Asp Lys Tyr Gly Leu Ser Pro Val Tyr Gly Phe Asn Tyr
1               5                   10                  15

Val Glu Met Gly Lys Thr Met Phe Lys Lys Thr Leu Leu Phe Phe Thr
            20                  25                  30

Ala Leu Phe Phe Ala Ala Leu Cys Ala Phe Ser Ala Asn Ala Asp Val
            35                  40                  45

Ile Ile Thr Gly Thr Arg Val Ile Tyr Pro Ala Gly Gln Lys Asn Val
        50                  55                  60

Ile Val Lys Leu Glu Asn Asn Asp Asp Ser Ala Ala Leu Val Gln Ala
65                  70                  75                  80

Trp Ile Asp Asn Gly Asn Pro Asn Ala Asp Pro Lys Tyr Thr Lys Thr
                85                  90                  95

Pro Phe Val Ile Thr Pro Pro Val Ala Arg Val Glu Ala Lys Ser Gly
            100                 105                 110

Gln Ser Leu Arg Ile Thr Phe Thr Gly Ser Glu Pro Leu Pro Asp Asp
            115                 120                 125

Arg Glu Ser Leu Phe Tyr Phe Asn Leu Leu Asp Ile Pro Pro Lys Pro
130                 135                 140

Asp Ala Ala Phe Leu Ala Lys His Gly Ser Phe Met Gln Ile Ala Ile
145                 150                 155                 160

Arg Ser Arg Leu Lys Leu Phe Tyr Arg Pro Ala Lys Leu Ser Met Asp
                165                 170                 175

Ser Arg Asp Ala Met Lys Lys Val Val Phe Lys Ala Thr Pro Glu Gly
            180                 185                 190

Val Leu Val Asp Asn Gln Thr Pro Tyr Tyr Met Asn Tyr Ile Gly Leu
            195                 200                 205

Leu His Gln Asn Lys Pro Ala Lys Asn Val Lys Met Val Ala Pro Phe
210                 215                 220

Ser Gln Ala Val Phe Glu Ala Lys Gly Val Arg Ser Gly Asp Lys Leu
```

```
                     225                 230                 235                 240

Lys Trp Val Leu Val Asn Asp Tyr Gly Ala Asp Gln Glu Gly Glu Ala
                         245                 250                 255

Ile Ala Gln (2) INFORMATION FOR SEQ ID NO:7:

(i) SEQUENCE CHARACTERISTICS:
        (A) LENGTH: 741 amino acids
        (B) TYPE: amino acid
        (D) TOPOLOGY: linear (ii) MOLECULE TYPE: protein (xi) SEQUENCE DESCRIPTION: SEQ ID NO:7:

Met Leu Asp Leu Met Asp Glu Ala Ile Val Lys Ser Pro Asn Ser Glu
  1               5                  10                  15

Asp Asp Thr Cys Val Phe Ala Ser Asp Ala Ile Pro Lys Gly Thr Phe
              20                  25                  30

Glu Tyr Gln Ser Gly Glu Met Lys Leu Lys Leu Glu Leu Pro Gln Ala
          35                  40                  45

Leu Thr Ile Arg Arg Pro Arg Gly Tyr Ile Ala Pro Ser Arg Trp Gln
 50                  55                  60

Thr Gly Thr Asn Ala Ala Phe Ala Asn Tyr Asp Ile Asn Tyr Tyr Arg
 65                  70                  75                  80

Ser Gly Asn Pro Glu Val Lys Ser Glu Ser Leu Tyr Val Gly Leu Arg
                  85                  90                  95

Ser Gly Val Asn Phe Gly Asn Trp Ala Leu Arg His Ser Gly Ser Phe
                 100                 105                 110

Ser Arg Phe Glu Asn Gln Ser Ser Ser Gly Phe Thr Asp Lys Gly Lys
             115                 120                 125

Asn His Tyr Glu Arg Gly Asp Thr Tyr Leu Gln Arg Asp Phe Ala Leu
         130                 135                 140

Leu Arg Gly Asn Val Thr Val Gly Asp Phe Phe Ser Thr Ala Arg Ile
145                 150                 155                 160

Gly Glu Asn Phe Gly Met Arg Gly Leu Arg Ile Ala Ser Asp Asp Arg
                 165                 170                 175

Met Leu Ala Pro Ser Gln Arg Gly Phe Ala Pro Val Val Arg Gly Val
             180                 185                 190

Ala Asn Thr Asn Ala Lys Val Ser Ile Lys Gln Asn Gly Tyr Thr Ile
         195                 200                 205

Tyr Gln Ile Thr Val Pro Ala Gly Pro Phe Val Ile Asn Asp Leu Tyr
210                 215                 220

Ala Ser Gly Tyr Ser Gly Asp Leu Thr Val Glu Ile Gln Glu Ser Asp
225                 230                 235                 240

Gly Lys Val Arg Ser Phe Ile Val Pro Phe Ser Asn Leu Ala Pro Leu
                 245                 250                 255

Met Arg Val Gly His Leu Arg Tyr Gln Leu Ala Gly Gly Arg Tyr Arg
             260                 265                 270

Ile Asp Ser Arg Thr Phe Asp Glu Arg Val Leu Gln Gly Val Leu Gln
         275                 280                 285

Tyr Gly Leu Thr Asn His Leu Thr Leu Asn Ser Ser Leu Leu Tyr Thr
         290                 295                 300

Arg His Tyr Arg Ala Gly Leu Phe Gly Phe Gly Leu Asn Thr Pro Ile
305                 310                 315                 320

Gly Ala Phe Ser Ala Asp Ala Thr Trp Ser His Ala Glu Phe Pro Leu
```

-continued

```
                    325                 330                 335
Lys His Val Ser Lys Asn Gly Tyr Ser Leu His Gly Ser Tyr Ser Ile
                340                 345                 350
Asn Phe Asn Glu Ser Gly Thr Asn Ile Thr Leu Ala Ala Tyr Arg Tyr
                355                 360                 365
Ser Ser Arg Asp Phe Tyr Thr Leu Ser Asp Thr Ile Gly Leu Asn Arg
            370                 375                 380
Thr Phe Arg Gln Phe Ser Gly Ala Tyr Leu Pro Glu Ile Tyr Arg Pro
385                 390                 395                 400
Lys Asn Gln Phe Gln Val Ser Leu Ser Gln Ser Leu Gly Asn Trp Gly
                405                 410                 415
Asn Leu Tyr Leu Ser Gly Gln Thr Tyr Asn Tyr Trp Glu Lys Arg Gly
                420                 425                 430
Thr Asn Thr Gln Tyr Gln Val Ala Tyr Ser Asn Ser Phe His Ile Leu
                435                 440                 445
Asn Tyr Ser Val Asn Leu Ser Gln Ser Ile Asp Lys Glu Thr Gly Lys
            450                 455                 460
Arg Asp Asn Ser Ile Tyr Leu Ser Leu Ser Leu Pro Leu Gly Asp Asn
465                 470                 475                 480
His Ser Ala Asp Ser Ser Tyr Ser Arg Ser Gly Asn Asp Ile Asn Gln
                485                 490                 495
Arg Leu Gly Val Asn Gly Ser Phe Gly Glu Arg His Gln Trp Ser Tyr
                500                 505                 510
Gly Ile Asn Ala Ser Arg Asn Asn Gln Gly Tyr Arg Ser Tyr Asp Gly
            515                 520                 525
Asn Leu Ser His Asn Asn Ser Ile Gly Ser Tyr Arg Ala Ser Tyr Ser
            530                 535                 540
Arg Asp Ser Leu Lys Asn Arg Ser Ile Ser Leu Gly Ala Ser Gly Ala
545                 550                 555                 560
Val Val Ala His Lys His Gly Ile Thr Leu Ser Gln Pro Val Gly Glu
                565                 570                 575
Ser Phe Ala Ile Ile His Ala Lys Asp Ala Ala Gly Ala Lys Val Glu
                580                 585                 590
Ser Gly Ala Asn Val Ser Leu Asp Tyr Phe Gly Asn Ala Val Met Pro
            595                 600                 605
Tyr Thr Ser Pro Tyr Glu Ile Asn Tyr Ile Gly Ile Asn Pro Ser Asp
        610                 615                 620
Ala Glu Ala Asn Val Glu Phe Glu Ala Thr Glu Arg Gln Ile Ile Pro
625                 630                 635                 640
Arg Ala Asn Ser Ile Ser Leu Val Asp Phe Arg Thr Gly Lys Asn Thr
                645                 650                 655
Met Val Leu Phe Asn Leu Thr Leu Pro Asn Gly Glu Pro Val Pro Met
            660                 665                 670
Ala Ser Thr Ala Gln Asp Ser Glu Gly Ala Phe Val Gly Asp Val Val
            675                 680                 685
Gln Gly Gly Val Leu Phe Ala Asn Lys Leu Thr Gln Pro Lys Gly Glu
            690                 695                 700
Leu Ile Val Lys Trp Gly Glu Arg Glu Ser Glu Gln Cys Arg Phe Gln
705                 710                 715                 720
Tyr Gln Val Asp Leu Asp Asn Ala Gln Ile Gln Ser His Asp Ile Gln
                725                 730                 735
Cys Lys Thr Ala Lys
            740
```

(2) INFORMATION FOR SEQ ID NO:8:

(i) SEQUENCE CHARACTERISTICS:
        (A) LENGTH: 205 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gln Lys Thr Pro Lys Lys Leu Thr Ala Leu Phe His Gln Lys Ser
 1               5                  10                  15

Thr Ala Thr Cys Ser Gly Ala Asn Tyr Ser Gly Ala Asn Tyr Ser Gly
                20                  25                  30

Ser Lys Cys Phe Arg Phe His Arg Leu Ala Leu Leu Ala Cys Val Ala
            35                  40                  45

Leu Leu Asp Cys Ile Val Ala Leu Pro Ala Tyr Ala Tyr Asp Gly Arg
        50                  55                  60

Val Thr Phe Gln Gly Glu Ile Leu Ser Asp Gly Thr Cys Lys Ile Glu
65                  70                  75                  80

Thr Asp Ser Gln Asn Arg Thr Val Thr Leu Pro Thr Val Gly Lys Ala
                85                  90                  95

Asn Leu Ser His Ala Gly Gln Thr Ala Ala Pro Val Pro Phe Ser Ile
           100                 105                 110

Thr Leu Lys Glu Cys Asn Ala Asp Asp Ala Met Lys Ala Asn Leu Leu
       115                 120                 125

Phe Lys Gly Gly Asp Asn Thr Thr Gly Gln Ser Tyr Leu Ser Asn Lys
   130                 135                 140

Ala Gly Asn Gly Lys Ala Thr Asn Val Gly Ile Gln Ile Val Lys Ala
145                 150                 155                 160

Asp Gly Ile Gly Thr Pro Ile Lys Val Asp Gly Thr Glu Ala Asn Ser
                165                 170                 175

Glu Lys Ala Pro Asp Thr Gly Lys Ala Gln Asn Gly Thr Val Ile Gln
            180                 185                 190

Pro Arg Phe Gly Tyr Phe Gly Ser Leu Leu Arg His Arg
        195                 200                 205
```

(2) INFORMATION FOR SEQ ID NO:9:

(i) SEQUENCE CHARACTERISTICS:
        (A) LENGTH: 437 amino acids
        (B) TYPE: amino acid
        (D) TOPOLOGY: linear (ii) MOLECULE TYPE: protein (xi) SEQUENCE DESCRIPTION: SEQ ID NO:9:

```
Met Asn Lys Lys Ser Tyr Ile Asn His Tyr Leu Thr Leu Phe Lys Val
 1               5                  10                  15

Thr Thr Leu Leu Phe Thr Leu Ser Ser Asn Pro Val Trp Ala Asn Ile
                20                  25                  30

Lys Thr Val Gln Gly Thr Thr Ser Gly Phe Pro Leu Leu Thr Arg Thr
            35                  40                  45

Phe Thr Phe Asn Gly Asn Leu Gln Trp Asn Val Ser Ala Leu Gln Pro
        50                  55                  60

Ala Tyr Ile Val Ser Ser Gln Ala Arg Asp Asn Leu Asp Thr Val His
65                  70                  75                  80

Ile Gln Ser Ser Glu Ile Asn Ala Pro Thr Asn Ser Leu Ala Pro Phe
                85                  90                  95
```

Asn Asn Trp Ile Asn Thr Lys Ser Ala Val Glu Leu Gly Tyr Ser Phe
            100                 105                 110

Ala Gly Ile Thr Cys Thr Ser Asn Pro Cys Pro Thr Met Lys Leu Pro
        115                 120                 125

Leu Leu Phe His Pro Asp Leu Thr Asn Leu Thr Pro Pro Gly Lys Lys
    130                 135                 140

Asn Ser Asp Gly Gly Glu Ile Phe Lys Leu His Asn Glu Ser Asn Leu
145                 150                 155                 160

Gly Val Ser Phe Gln Ile Gly Val Lys Thr Asn Thr Ser Leu Asp Trp
                165                 170                 175

Val Asn Ala Lys Asn Asn Phe Ser Ser Leu Lys Val Leu Met Val Pro
            180                 185                 190

Phe Asn Ser Ser Asp Lys Ile Ser Leu His Leu Arg Ala Lys Phe His
        195                 200                 205

Leu Leu Thr Asp Phe Ser Ser Leu Asn Asn Asp Ile Thr Ile Asp Pro
    210                 215                 220

Met Asn Thr Ser Ile Gly Lys Ile Asn Leu Glu Thr Trp Arg Gly Ser
225                 230                 235                 240

Thr Gly Asn Phe Ser Val Lys Tyr Val Gly Glu Asp Lys Gly Asp Ile
                245                 250                 255

Ser Ile Phe Phe Asn Thr Pro Lys Ile Ile Leu Lys Lys Gln Gln Arg
            260                 265                 270

Arg Cys Thr Leu Asn Asn Ala Pro Val Ser Pro Asn Pro Val Lys Leu
        275                 280                 285

Arg Ala Val Lys Lys Arg Glu Leu Glu Ala Gln Ser Glu Met Glu Gly
    290                 295                 300

Gly Thr Phe Gln Leu Arg Val Asn Cys Asp Asn Thr Thr Tyr Asn Lys
305                 310                 315                 320

Ala Asn Gly Lys Trp Leu Phe Pro Val Val Lys Val Thr Phe Thr Asp
                325                 330                 335

Glu Asp Gly Thr Thr Asn Asn Gly Thr Asn Asp Leu Leu Arg Thr Gln
            340                 345                 350

Thr Gly Ser Gly Gln Ala Thr Gly Val Ser Leu Arg Ile Lys Arg Glu
        355                 360                 365

Asn Gly Thr Glu Thr Val Lys Tyr Gly Ala Asp Ser Ala Gln Met Gly
    370                 375                 380

Asn Ala Gly Gln Phe Glu Leu Arg Lys Gln Pro Ser Pro Ala Gly Gly
385                 390                 395                 400

Asp Gln Tyr Ala Glu Glu Thr Phe Lys Val Tyr Val Lys Asp Ser
                405                 410                 415

Thr Arg Gly Thr Leu Ile Glu Gly Lys Val Lys Ala Ala Thr Phe
        420                 425                 430

Thr Met Ser Tyr Gln
        435

(2) INFORMATION FOR SEQ ID NO:10:

(i) SEQUENCE CHARACTERISTICS:
        (A) LENGTH: 316 amino acids
        (B) TYPE: amino acid
        (D) TOPOLOGY: linear (ii) MOLECULE TYPE: protein (xi) SEQUENCE DESCRIPTION: SEQ ID NO:10:

Met Leu Ala Lys Ala Lys Tyr Arg Lys Asp Tyr Lys Gln Pro Asp Phe

```
             1               5              10              15

Thr Val Thr Asp Ile Tyr Leu Asp Phe Gln Leu Asp Pro Lys Asn Thr
                         20              25              30

Val Val Thr Ala Thr Thr Lys Phe Gln Arg Leu Asn Asn Glu Ala Thr
                         35              40              45

Ser Leu Arg Leu Asp Gly His Ser Phe Gln Phe Ser Ser Ile Lys Phe
                 50              55              60

Asn Gly Glu Pro Phe Ser Asp Tyr Gln Gln Asp Gly Glu Ser Leu Thr
        65               70              75                           80

Leu Asp Leu Lys Asp Lys Ser Ala Asp Glu Phe Glu Leu Glu Ile Val
                         85              90              95

Thr Phe Leu Val Pro Ala Glu Asn Thr Ser Leu Gln Gly Leu Tyr Gln
                         100             105             110

Ser Gly Glu Gly Ile Cys Thr Gln Cys Glu Ala Glu Gly Phe Arg Gln
                     115             120             125

Ile Thr Tyr Met Leu Asp Arg Pro Asp Val Leu Ala Arg Tyr Ile Ile
                     130             135             140

Lys Ile Thr Ala Asp Lys Thr Lys Tyr Pro Phe Leu Leu Ser Asn Gly
        145                 150             155                     160

Asn Arg Ile Ala Ser Gly Glu Leu Glu Asp Gly Arg His Trp Val Glu
                         165             170             175

Trp Asn Asp Pro Phe Pro Lys Pro Ser Tyr Leu Phe Ala Leu Val Ala
                         180             185             190

Gly Asp Xaa Gly Leu Leu Gln Asp Xaa Phe Ile Thr Lys Ser Gly Arg
                         195             200             205

Glu Val Ala Leu Glu Leu Tyr Val Asp Arg Gly Asn Leu Asn Arg Ala
                         210             215             220

Thr Gly Ala Met Glu Ser Leu Lys Lys Ala Met Lys Trp Asp Glu Asp
        225                 230             235                     240

Arg Phe Ile Leu Glu Phe Tyr Leu Asp Ile Tyr Met Ile Ala Ala Ala
                         245             250             255

Asp Ser Ser Asn Met Gly Ala Met Glu Asn Lys Gly Leu Asn Ile Phe
                         260             265             270

Asn Ser Lys Leu Val Leu Ala Asn Pro Gln Thr Ala Thr Asp Glu Asp
                         275             280             285

Tyr Leu Val Ile Glu Ser Val Ile Ala His Glu Tyr Ser His Asn Trp
                         290             295             300

Thr Gly Asn Arg Val Thr Arg Arg Asp Gly Phe Asn
        305                 310             315

(2) INFORMATION FOR SEQ ID NO:11:

(i) SEQUENCE CHARACTERISTICS:
             (A) LENGTH: 670 amino acids
             (B) TYPE: amino acid
             (C) STRANDEDNESS: single
             (D) TOPOLOGY: linear (ii) MOLECULE TYPE: protein (xi) SEQUENCE DESCRIPTION: SEQ ID NO:11:

Lys Ile Glu Glu Gly Lys Leu Val Ile Trp Ile Asn Gly Asp Lys Gly
    1               5                   10                  15

Tyr Asn Gly Leu Ala Glu Val Gly Lys Lys Phe Glu Lys Asp Thr Gly
                     20                  25                  30

Ile Lys Val Thr Val Glu His Pro Asp Lys Leu Glu Glu Lys Phe Pro
                     35                  40                  45
```

-continued

```
Gln Val Ala Ala Thr Gly Asp Gly Pro Asp Ile Ile Phe Trp Ala His
     50                  55                  60
Asp Arg Phe Gly Gly Tyr Ala Gln Ser Gly Leu Leu Ala Glu Ile Thr
 65                  70                  75                  80
Pro Asp Lys Ala Phe Gln Asp Lys Leu Tyr Pro Phe Thr Trp Asp Ala
                 85                  90                  95
Val Arg Tyr Asn Gly Lys Leu Ile Ala Tyr Pro Ile Ala Val Glu Ala
            100                 105                 110
Leu Ser Leu Ile Tyr Asn Lys Asp Leu Leu Pro Asn Pro Pro Lys Thr
        115                 120                 125
Trp Glu Glu Ile Pro Ala Leu Asp Lys Glu Leu Lys Ala Lys Gly Lys
130                 135                 140
Ser Ala Leu Met Phe Asn Leu Gln Glu Pro Tyr Phe Thr Trp Pro Leu
145                 150                 155                 160
Ile Ala Ala Asp Gly Gly Tyr Ala Phe Lys Tyr Glu Asn Gly Lys Tyr
                165                 170                 175
Asp Lys Ile Lys Asp Val Gly Val Asp Asn Ala Gly Ala Lys Ala Gly
            180                 185                 190
Leu Thr Phe Leu Val Asp Leu Ile Lys Asn Lys His Met Asn Ala Asp
        195                 200                 205
Thr Asp Tyr Ser Ile Ala Glu Ala Ala Phe Asn Lys Gly Glu Thr Ala
210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
            260                 265                 270
Asn Lys Glu Leu Ala Lys Glu Phe Leu Glu Asn Tyr Leu Leu Thr Asp
        275                 280                 285
Glu Gly Leu Glu Ala Val Asn Lys Asp Lys Pro Leu Gly Ala Val Ala
290                 295                 300
Leu Lys Ser Tyr Glu Glu Glu Leu Ala Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
            340                 345                 350
Ser Gly Arg Gln Thr Val Asp Glu Ala Leu Lys Asp Ala Gln Thr Arg
        355                 360                 365
Ile Thr Lys Ile Glu Gly Arg Thr Leu Ser Ser Asn Pro Val Trp Ala
370                 375                 380
Asn Ile Lys Thr Val Gly Thr Thr Ser Gly Phe Pro Leu Leu Thr Arg
385                 390                 395                 400
Thr Phe Thr Glu Asn Gly Asn Leu Trp Asn Val Ser Ala Leu Pro Ala
                405                 410                 415
Tyr Ile Val Ser Ser Ala Arg Asp Asn Leu Asp Thr Val His Ile Gln
            420                 425                 430
Ser Ser Glu Ile Asn Ala Pro Thr Asn Ser Leu Ala Pro Glu Asn Asn
        435                 440                 445
Trp Ile Asn Thr Lys Ser Ala Val Glu Leu Gly Tyr Ser Phe Ala Gly
450                 455                 460
Ile Thr Cys Thr Ser Asn Pro Cys Pro Thr Met Lys Leu Pro Leu Leu
```

```
465                 470                475                480
Phe His Pro Leu Thr Asn Leu Thr Pro Pro Gly Lys Lys Asn Ser Asp
                    485                490                495
Gly Gly Glu Ile Phe Lys Leu His Asn Glu Ser Asn Leu Gly Val Ser
                500                505                510
Phe Gln Ile Gly Val Lys Thr Asn Thr Ser Leu Asp Trp Val Asn Ala
            515                520                525
Lys Asn Asn Phe Ser Ser Leu Lys Val Leu Met Val Pro Phe Asn Ser
530                 535                540
Ser Lys Ser Ile Ser Leu His Leu Arg Ala Lys Phe His Leu Leu Thr
545                 550                555                560
Asp Phe Ser Ser Leu Asn Asn Asp Ile Thr Ile Asp Pro Met Asn Thr
                565                570                575
Ser Ile Gly Lys Ile Asn Leu Glu Thr Trp Arg Gly Ser Thr Gly Asn
                580                585                590
Phe Ser Val Lys Tyr Val Gly Glu Asp Lys Gly Asp Ile Ser Ile Phe
                595                600                605
Phe Asn Thr Pro Lys Ile Ile Leu Lys Lys Gln Gln Arg Arg Cys Thr
                610                615                620
Leu Asn Asn Ala Pro Val Ser Pro Asn Pro Val Lys Leu Arg Ala Val
625                 630                635                640
Lys Lys Arg Glu Leu Glu Ala Gln Ser Glu Met Glu Gly Gly Thr Phe
                645                650                655
Leu Arg Val Asn Cys Asp Asn Thr Thr Tyr Asn Lys Ala Asn
                660                665                670

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:12:

GTGCTGGATC CGTTTCTCTT GCATTACATT AGG                    33

(2) INFORMATION FOR SEQ ID NO:13:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:13:

TTAGGAATTC GGAAGCGTTT TTTACTTTTT TTGG                   34

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

AACGAATTCT GCTGTTTATT AAGGCTTTAG                        30
```

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:15:

AGCTGGATCC TTGTAGGGTG GGCGTAAGCC                          30

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:16:

AGCTGGATCC TTGTAGGGTG GGCGTAAGCC                          30

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:17:

AACGGATTCG TTTGCTGTTT ATTAAGCCTT                          30

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:18:

AACGGATTCG TTTGCTGTTT ATTAAGCCTT                          30

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:19:

GGCAAATACG CACCGCTAAA T                                  21

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:20:

CGGACGAAGA TGGTACAACG A                                  21

(2) INFORMATION FOR SEQ ID NO:21:

-continued

```
    (i) SEQUENCE CHARACTERISTICS:
         (A) LENGTH: 34 base pairs
         (B) TYPE: nucleic acid
         (C) STRANDEDNESS: single
         (D) TOPOLOGY: linear (xi) SEQUENCE DESCRIPTION: SEQ ID NO:21:

CCAAGCTTGG CCCGACATTA TTATTGATAT GACA                                   34
```